(12) United States Patent
Szczepankiewicz et al.

(10) Patent No.: US 10,485,814 B2
(45) Date of Patent: Nov. 26, 2019

(54) NICOTINAMIDE RIBOSIDE ANALOGS AND PHARMACEUTICAL COMPOSITIONS AND USES THEREOF

(71) Applicant: GlaxoSmithKline Intellectual Property (No. 2) Limited, Brentford, Middlesex (GB)

(72) Inventors: Bruce G. Szczepankiewicz, Hopkinton, MA (US); Frank Preugschat, Research Triangle Park, NC (US); Karsten Koppetsch, Woburn, MA (US); Robert B. Perni, Marlborough, MA (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 15/315,160

(22) PCT Filed: Jun. 5, 2015

(86) PCT No.: PCT/IB2015/054281
§ 371 (c)(1),
(2) Date: Nov. 30, 2016

(87) PCT Pub. No.: WO2015/186114
PCT Pub. Date: Dec. 10, 2015

(65) Prior Publication Data
US 2017/0189433 A1    Jul. 6, 2017

Related U.S. Application Data

(60) Provisional application No. 62/008,707, filed on Jun. 6, 2014.

(51) Int. Cl.
*A01N 43/04* (2006.01)
*A61K 31/70* (2006.01)
(Continued)

(52) U.S. Cl.
CPC ............ *A61K 31/706* (2013.01); *A61K 8/675* (2013.01); *A61K 45/06* (2013.01); *A61Q 19/004* (2013.01);
(Continued)

(58) Field of Classification Search
None
See application file for complete search history.

(56) References Cited

U.S. PATENT DOCUMENTS 6,258,795 B1 * 7/2001 von Borstel ......... A61K 31/513
514/49
10,206,940 B2 2/2019 Sauve et al.
2006/0229265 A1 * 10/2006 Milburn ............ A61K 31/4436
514/43

FOREIGN PATENT DOCUMENTS

WO WO 2007/061798 A2 5/2007
WO WO 2012/094343 A1 7/2012
(Continued)

OTHER PUBLICATIONS

Franchetti et al. Bioorganic & Medicinal Chemistry Letters (2004), vol. 14, pp. 4655-4658.*
(Continued)

*Primary Examiner* — Patrick T Lewis
(74) *Attorney, Agent, or Firm* — Diane E. Furman; Joshua C. Sanders

(57) ABSTRACT

Provided herein are stereoisomerically pure ester and carbonate analogues of nicotinamide riboside and nicotinamide riboside hydride, and pharmaceutical compositions and uses thereof. The stereoisomerically pure ester and carbonate analogues of nicotinamide riboside and nicotinamide riboside hydride may be used to treat a disease or disorder that would benefit from increased NAD levels including a mitochondrial disease or disorder, insulin resistance, a metabolic syndrome, diabetes, obesity, for increasing insulin sensitivity in a subject, or to treat or prevent a skin condition.

The compounds have general formulas (I) or (II):

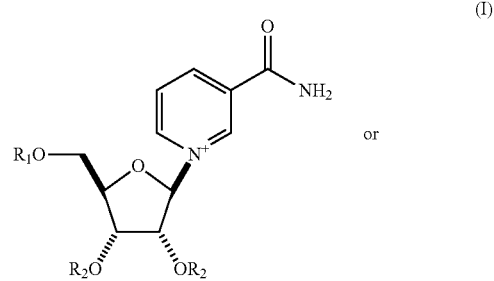

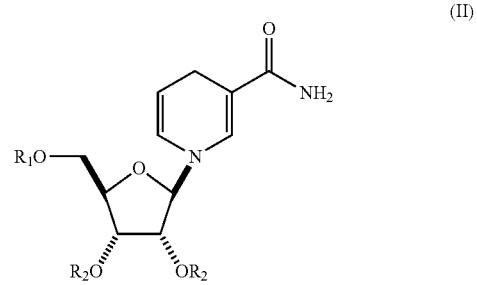

wherein $R_1$ is —C(=O)—X—($C_2$-$C_{18}$ straight chain or branched) alkyl or —C(=O)—X—($C_2$-$C_{18}$ straight chain or branched) alkenyl; each $R_2$ is independently selected from hydrogen, and a —C(O)—X—($C_1$-$C_{18}$ straight chain or branched) alkyl or a —C(O)—X—($C_2$-$C_{18}$ straight chain or branched) alkenyl; and X is a covalent bond or O.

18 Claims, 36 Drawing Sheets

(51) Int. Cl.
   *A61K 31/706*   (2006.01)
   *C07H 19/048*   (2006.01)
   *A61K 8/67*     (2006.01)
   *A61Q 19/00*    (2006.01)
   *A61Q 19/08*    (2006.01)
   *A61K 45/06*    (2006.01)

(52) U.S. Cl.
   CPC .......... *A61Q 19/08* (2013.01); *C07H 19/048* (2013.01); *A61K 2800/522* (2013.01)

(56) References Cited

FOREIGN PATENT DOCUMENTS

WO   WO 2015/014722 A1   2/2015
WO      2015066382 A1    5/2015

OTHER PUBLICATIONS

Hoong et al. J. Org. Chem. (1992), vol. 57, pp. 5563-5565.*
Chi et al. Curr. Opin. Clin. Nutr. Metab. Care (2013), vol. 16, pp. 657-661.*
Franchetti, et al. Bioorganic & Medicinal Chemistry Letters, 14(18): 4655-4658 (Sep. 20, 2004).
Jaemoon, et al. Chemical Communications, 8: 729-730 (Jan. 1, 1999).
Mikhailopulo, et al. Synthesis, 1981(05): 388-389 (Jan. 1, 1981).
Haykes, et al. Journal of the Chemical Society, p. 3727 (Jan. 1, 1957).
Jarman et al. J. Chem. Soc. (C) (1969), pp. 199-203.
Kam, et al. Carbohydrate Research, 77(1):275-280 (Jan. 1, 1979).
Khan et al. EMBO Molecular Medicine (2014), vol. 6, pp. 721-731.
Tanimori, Shinji, et al. "An Efficient Chemical Synthesis of Nicotinamide Riboside (NAR) and Analogues" Bioorganics & Medicinal Chemistry Letters, 12(8) 1135-1137 (Apr. 1, 2002).
Yang, Tianle, et al. "Syntheses of Nicotinamide Riboside and Derivatives: Effective Agents for Increasing Nicotinamide Adenine Dinucleotide Concentrations in Mammalian Cells", Journal of the American Chemical Society, American Chemical Society, US, 50(26):6458-6461 (Jan. 1, 2007).
Yu, et al. Advanced Drug Delivery Reviews, 48(1):27-42 (May 16, 2001).

* cited by examiner common numbering scheme

FIGURE 3 Compound Table and Plasma Stability

| No. | Compound Name | Structure | [M+H]+ /[M]+ | T=0 min (NR analyte) | T = 30 min | T = 60 min | Comments |
|---|---|---|---|---|---|---|---|
| 1 | NRH tri-acetate | 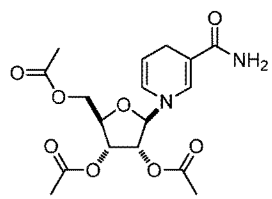 | 382 | 0 | 1910 | 8040 | clear solution |
| 2 | NRH tri-propionate | 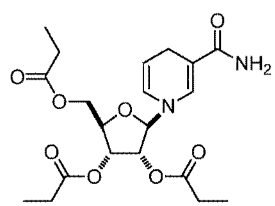 | 424 | 295 | 3400 | 10400 | light yellow |
| 3 | NRH tri-butyrate | 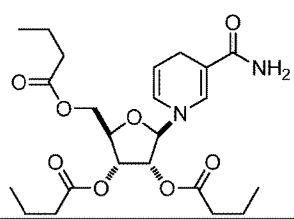 | 466 | 0 | 3650 | 13000 | yellow with floaters |

FIGURE 3 CONT.

| | | | | | | | |
|---|---|---|---|---|---|---|---|
| 4 | NRH tri-isobutyrate | [structure] | 466 | 0 | 1200 | 1210 | clear solution |
| 5 | NR+ tri-pentanoate | [structure] | 507 | 0 | 4810 | 2710 | clear solution |
| 6 | NR+ tri-hexanoate | [structure] | 549 | 0 | 9310 | 8370 | clear solution |

FIGURE 3 CONT.

| | | | | | | |
|---|---|---|---|---|---|---|
| 7 | NRH tri-ethyl-carbonate | [structure] | 472 | 974 | 14500 | 8150 | clear solution |
| 8 | NRH tri-benzoate | [structure] | 568 | 0 | 0 | 0 | clear floaters |
| 9 | NR+ mono-hexanoate | [structure] | 353 | 8920 | 23100 | 12900 | clear floaters |
| 10 | NRH mono-decanoate | [structure] | 410 | 12000 | 50300 | 46300 | clear floaters |

| | | | | | | |
|---|---|---|---|---|---|---|
| 11 | NRH mono-tetra-decanoate |  | 466 | 1410 | 4190 | 8440 | cloudy floaters |
| 12 | Nic mono-nucleotide (NMN) |  | 334 | 2060 | 3720 | 3110 | clear |
| 13 | NR+ mono-oleate |  | 491 | 6390 | 18000 | 8420 | cloudy floaters |
| 14 | NR+ mono-hexanoate |  | 353 | 1840 | 26900 | 7860 | clear |

| | | | | | | |
|---|---|---|---|---|---|---|
| 15 | NR+ mono-nonanoate |  | 395 | | 25200 | 5730 | clear |
| 16 | NR+ mono-dodecanoate |  | 437 | 0 | 11100 | 2180 | cloudy floaters |
| 17 | NR+ mono-pentanoate |  | 339 | 218 | 11900 | 3250 | clear |
| 18 | NR+ mono-undecanoate |  | 423 | 7630 | 49100 | 11100 | cloudy floaters |

FIGURE 9B

| Compound | chemical structure | description | MW | MF | description |
|---|---|---|---|---|---|
| A | 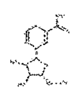 | NRH | 256.255 | C11H16N2O5 | NRH |
| B | 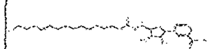 | NRH monoC16 | 494.664 | C27H46N2O6 | NR ester |
| C | 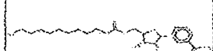 | NR tfa monoC12 | 550.565 | C23H37N2O6, C2F3O2 | NR ester |
| D | 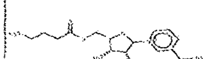 | NR tfa monoC5 | 452.379 | C16H23N2O6, C2F3O2 | NR ester |
| E | 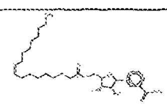 | NR tfa monooleate | 632.708 | C29H47N2O6, C2F3O2 | NR ester |
| F | 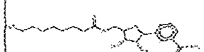 | NR tfa C9 monoester | 508.485 | C20H31N2O6, C2F3O2 | NR ester |

NICOTINAMIDE RIBOSIDE ANALOGS AND PHARMACEUTICAL COMPOSITIONS AND USES THEREOF

This application is a § 371 of International Application No. PCT/IB2015/054281, filed 05 Jun. 2015, which claims the benefit of U.S. Provisional Application No. 62/008,707, filed 06 Jun. 2014, which are incorporated herein in their entireties.

TECHNICAL FIELD

The invention relates to compositions of nicotinamide riboside analogs, including esters and carbonates, for use in elevating levels of nicotinamide adenine dinucleotide (NAD$^+$) in cells and tissues of an organism. The novel compositions include pharmaceuticals compositions and nutritional supplements, and related methods for treating or preventing a disease or condition in an organism by elevating NAD$^+$ levels.

BACKGROUND

In the early part of the 20$^{th}$ century, vitamin B$_3$ was identified as a component missing from the diet of pellagra patients. Supplementation with nicotinic acid, or niacin, ameliorated the symptoms of pellagra, and prevented the onset of this condition in areas where it was prevalent. The biochemical role of niacin was elucidated in the 1930s, when it was found to be critical for the biosynthesis of nicotinamide adenine dinucleotide (NAD+), a compound essential for cellular respiration (Preiss, J.; Handler, P. Biosynthesis of Diphosphopyridine Nucleotide I. Identification of Intermediates J. Biol. Chem. 1958 233, 488-492.; Preiss, J.; Handler, P. Biosynthesis of Diphosphopyridine Nucleotide II. Enzymatic Aspects J. Biol. Chem. 1958 233, 493-500). The precise role of NAD in cellular respiration is well understood. As glucose and fatty acids are oxidized, NAD can accept a hydride equivalent, which results in its reduction to NADH. NADH can donate a hydride equivalent, resulting in oxidation back to NAD. These reduction-oxidation cycles use NAD for the temporary storage of hydride ion, but they do not consume NAD. There are other enzymes that use NAD in a different manner, and for purposes not directly related to energy production. Poly-ADPribose polymerases (PARPs), ADPribose transferases (ARTs), and sirtuins all catalyze reactions that release nicotinamide from NAD. This reaction generates a significant amount of energy, similar to ATP hydrolysis. The reverse reaction does not occur readily, so NAD must be replenished by other mechanisms (Bogan, K. L.; Brenner, C. Nicotinic Acid, Nicotinamide, and Nicotinamide Riboside: A Molecular Evaluation of NAD$^+$ Precursor Vitamins in Human Nutrition Annu. Rev. Nutr. 2008, 28, 115-130).

Niacin (or nicotinic acid (pyridine-3-carboxylic acid)), and its amide niacinamide (or nicotinamide (pyridine-3-carboxamide)) are converted to NAD in vivo. Nicotinamide adenine dinucleotide (NAD$^+$) is a key coenzyme found in all living cells that functions as an electron carrier in oxidative and reductive biochemical reactions occurring throughout metabolism. In mammals, niacinamide, rather than niacin, may be the major NAD precursor. The set of biosynthetic transformations from niacinamide to NAD is shown in FIG. 1. The rate limiting step for this pathway is the formation of the bond between niacinamide and 5-phosphoribose-1-pyrophosphate (PRPP), and it is catalyzed by nicotinamide phosphoribosyl transferase (NAMPT) (Revollo, J. R.; Grimm, A. A.; Imai, S.-I. J. Biol. Chem. 2004, 279, 50754-50763). The NAMPT pathway is thought to be the most efficient route known for nicotinamide recycling. Niacin enters into a similar set of transformations, but in a final step, the carboxylic acid must be converted to a carboxamide to produce NAD. The biosynthesis of NAD from niacin follows the Preiss-Handler pathway (FIG. 1).

In 1982, nicotinamide riboside (NR) was investigated as a NAD precursor in prokaryotes (Liu, G.; Foster, J.; Manlapaz-Ramos, R.; Loivera, B. M. "Nucleoside Salvage Pathway for NAD Biosynthesis in Salmonella typhimurium" J. Bacteriol. 1982, 152, 1111-1116). In contrast to niacin, exogenously supplied NR is hypothesized to bypass the first and most energy-consuming part of both the Preiss-Handler pathway and the NAMPT pathway (FIG. 1). Although NR appears to be a natural precursor for NAD, it likely represents only a small amount, if any, of NAD biosynthesis owing to the apparent scarcity of NR in dietary sources. NR contains a high energy glycosidic bond that is spontaneously labile in aqueous solution, yielding nicotinamide and ribose decomposition products. This spontaneous reaction occurs over the course of hours or days depending on the exact ambient conditions, but it makes any naturally occurring NR difficult to keep in food sources, while nicotinic acid or nicotinamide are considerably more stable and easy to prepare and administer. NR has been reported to occur in milk (Bieganowski and Brenner (2004) Cell 117: 495-502) and beer, but the amounts typically present are probably too small to be nutritionally significant.

Currently, NR supplementation is limited by the available commercial supply. NR supplementation could represent a dietary alternative to niacin, with the advantage of being a more efficient NAD precursor. By taking advantage of a natural pathway to synthesize NAD while consuming less energy, NR could offer benefits for human health. Cells are constantly subject to damage by normal environmental factors, and they have evolved repair mechanisms to continuously reverse this damage. The repair mechanisms consume NAD by scission of the high energy glycosidic linkage to produce species such as poly-ADPribose and ADP-ribosylated proteins. In severely damaged cells, energy stores are not sufficient to produce the NAD necessary to maintain homeostasis, and the damage becomes irreversible. Therefore, an energy-rich NAD precursor such as NR may be able to address cell and tissue damage at the molecular level.

NR can be difficult to isolate from natural sources, so it is typically produced by chemical synthesis. The first chemical synthesis was accomplished by Todd and co-workers in 1957 (Haynes, L. J.; Hughes, N. A.; Kenner, G. W.; Todd, A. J. Chem. Soc. 1957, 3727-3732). This group produced NR chloride as a mixture of α and β anomers about the glycosidic linkage in an approximately 1:4 ratio. The product was described as a hygroscopic oil that could not be crystallized. Other investigators who isolated NR chloride from biochemical sources also described it as a hygroscopic oil (Schlenk, F. "Nicotinamide Nucleoside" Naturwiss. 1940, 28, 46-47; Gingrich, W.; Schlenk, F. "Codehydrogenase I and Other Pyridinium Compounds as V-Factor for Hemophilus Influenzae and H. Parainfluenzae" J. Bacteriol. 1944, 47, 535-550). Significantly, biochemical syntheses should have produced only the natural β-anomer, though the exact stereochemical arrangement was not determined. Later reports confirmed the hygroscopic, amorphous nature of NR chloride (Jarman, M.; Ross, W. C. J. J. Chem. Soc. C, 1969, 199-203; and Atkinson, M. R.; Morton, R. K.; Naylor, R. Synthesis of Glycosylpyridinium Compounds from Glycosylamines and from Glycosyl Halides *J. Chem Soc.* 1965, 610-615). Other groups investigated alternative NR anions. One synthesis described the anomerically pure NR bromide salt as crystalline, but the product was not adequately described to ascertain whether the material was truly crystalline or merely an amorphous solid (Lee, J.; Churchill, H.; Choi, W.-B.; Lynch, J. E.; Roberts, F. E.; Volante, R. P.; Reider, P. J. "A chemical synthesis of nicotinamide adenine dinucleotide (NAD+)" *Chem. Commun.* 1999, 729-730). Subsequently, other NR salts were prepared and solids were obtained, though they were never described as crystalline (Tanimori, S.; Ohta, T.; Kirihata, M. An Efficient Chemical Synthesis of Nicotinamide Riboside (NAR) and Analogues *Bioorg. Med. Chem. Lett.* 2002, 12, 1135-1137; Franchetti, P.; Pasqualini, M.; Petrelli, R.; Ricciutelli, M.; Vita, P.; Cappellacci, L. *Bioorg. Med. Chem. Lett.* 2004, 14, 4655-4658; Yang, T.; Chan, N. Y.-K.; Sauve, A. A. *J. Med. Chem.* 2007, 50, 6458-6461). In addition, methods of preparing nicotinamide riboside from enriched natural sources, such as a genetically engineered yeast strain, have been described (see, WO 2010/111111).

While nicotinamide riboside itself is useful as an efficient precursor of $NAD^+$ to elevate $NAD^+$ levels and improve cell and organismal health, its bioavailability under various modes of administration may be limited. Accordingly, nicotinamide riboside analogs with improved bioavailability and optimal tissue selectivity are desirable, however such compounds may also prove toxic to cells. For example, benzamide riboside is a well-known antitumor agent that is metabolized to the active NAD analogue benzamide adenine dinucleotide, which inhibits certain NAD-dependent dehydrogenases, such as malate dehydrogenase and glutamic acid dehydogenase, which may cause adverse effects. Accordingly, there is a need for $NAD^+$ elevating agents that are bioavailable, stable, effective at $NAD^+$ elevation in the desired tissue(s) and safe from adverse effects on $NAD^+$-dependent biological processes.

SUMMARY

The invention relates to stereoisomerically pure nicotinamide riboside (NR) analogues, including esters and carbonates, having Structural Formulas (I), which is the oxidized form of nicotinamide riboside (NR), or Structural Formula (II), which is the reduced form of nicotinamide riboside (NRH), as shown below:

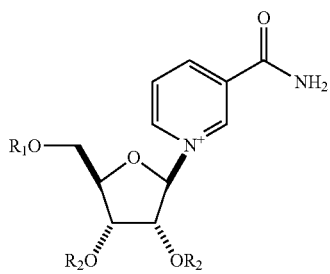

(I)

or

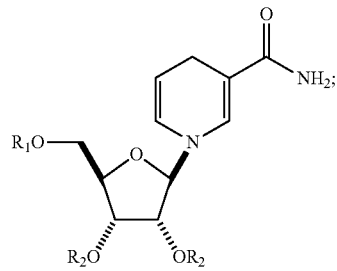

(II)

or a pharmaceutically acceptable salt thereof, where $R_1$ is —C(=O)—X—($C_1$-$C_{18}$ straight chain or branched) alkyl or a —C(O)—X—($C_2$-$C_{18}$ straight chain or branched) alkenyl, each $R_2$ is independently selected from hydrogen, and a —C(O)—X—($C_1$-$C_{18}$ straight chain or branched) alkyl or a —C(O)—X—($C_2$-$C_{18}$ straight chain or branched) alkenyl; and X is a covalent bond (in the case of esters) or O (in the case of carbonates). Structural Formula (I) corresponds to compounds comprising a reduced nicotinamide moiety, and Structural Formula (II) corresponds to compounds comprising an oxidized nicotinamide moiety. In certain embodiments, the invention provides, a stereoisomerically pure compound esters of Structural Formulas (I) and (II), wherein the compound is not nicotinamide riboside 2',3', 5'-triacetate:

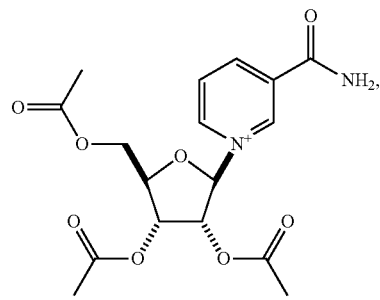 [SMILES: CC(=O)OC[C@H]1O[C@@H]([n+]2cccc(C(N)=O)c2)[C@H](OC(C)=O)[C@@H]1OC(C)=O]

and/or is not nicotinamide riboside 5'-monoacetate:

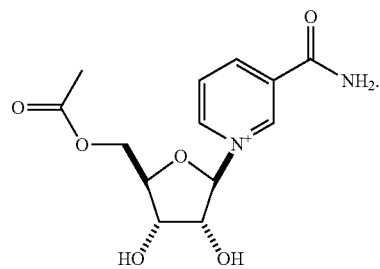 [SMILES: CC(=O)OC[C@H]1O[C@@H]([n+]2cccc(C(N)=O)c2)[C@H](O)[C@@H]1O]

In further embodiments, the invention provides the stereoisomerically pure compound esters of Structural Formulas (I) and (II), wherein the compound is not nicotinamide riboside hydride 2',3',5'-triacetate:

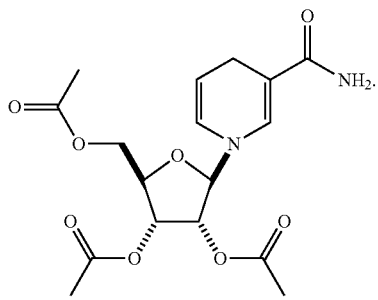 [SMILES: CC(=O)OC[C@H]1O[C@@H](N2C=CCC(C(N)=O)=C2)[C@H](OC(C)=O)[C@@H]1OC(C)=O]

In certain embodiments, the invention provides a compound represented by Structural Formula (I) (nicotinamide riboside esters and carbonates). In other embodiments, the invention provides a compound represented by structural Formula (II) nicotinamide riboside hydride analogs, e.g., nicotinamide riboside hydride 5' monoacetate, wherein $R_1$ is —C(=O)—$CH_3$ and each occurrence of $R_2$ is hydrogen.

In certain embodiments, the invention provides a stereoisomerically pure nicotinamide riboside ester compound as described above, wherein $R_1$ is —C(=O)—($C_1$-$C_3$ straight chain or branched) alkyl, and each $R_2$ is independently selected from hydrogen, and a —C(=O)—($C_1$-$C_3$ straight chain or branched) alkyl. In particular embodiments, the compound is nicotinamide riboside hydride 2',3',5'-triacetate, nicotinamide riboside hydride 2',3',5'-tripropionate, nicotinamide riboside hydride 2',3',5'-tri-n-butyrate, or nicotinamide riboside hydride 2',3',5'-triisobutyrate.

In another embodiment, the stereoisomerically pure compound of Structural Formulas (I) or (II) is not nicotinamide riboside hydride 2',3',5'-triacetate.

In certain further embodiments, the invention provides a stereoisomerically pure nicotinamide riboside 5'-monoester compound as described above, wherein $R_1$ is —C(=O)—($C_4$-$C_{18}$ straight chain or branched) alkyl or alkenyl, and each occurrence of $R_2$ is hydrogen. In particular embodiments, the stereoisomerically pure compound is nicotinamide riboside 5'-monopentanoate, nicotinamide riboside 5'-monohexanoate, nicotinamide riboside 5'-mononnonanoate, nicotinamide riboside 5'-monoundecanoate, nicotinamide riboside 5'-monododecanoate, or nicotinamide riboside 5'-monooleate. In other embodiments, the stereoisomerically pure compound is nicotinamide riboside hydride 5'-monohexanoate, nicotinamide riboside hydride 5'-monodecanoate, or nicotinamide riboside hydride 5'-monotetradecanoate.

In certain embodiments, the stereoisomerically pure compound of Structural Formula (I) or (II) comprises an $R_1$ and/or $R_2$ that is —C(=O)—X—($C_1$-$C_{10}$ straight chain or branched) alkyl or —C(=O)—X—($C_2$-$C_{10}$ straight chain or branched) alkenyl. In particular embodiments, the stereoisomerically pure compound comprises a straight chain or branched alkyl or alkenyl that is a $C_1$, $C_2$, $C_3$, $C_4$, $C_5$, $C_6$, $C_7$, $C_8$, $C_9$, or $C_{10}$ alkyl, or a $C_2$, $C_3$, $C_4$, $C_5$, $C_6$, $C_7$, $C_8$, $C_9$, or $C_{10}$ alkenyl.

In other embodiments, the stereoisomerically pure compound of Structural Formula (I) or (II) comprises an $R_1$ and/or $R_2$ that is —C(=O)—X—($C_{11}$-$C_{18}$ straight chain or branched) alkyl or alkenyl. In particular embodiments, the stereoisomerically pure compound comprises a straight chain or branched alkyl or alkenyl that is a $C_{11}$, $C_{12}$, $C_{13}$, $C_{14}$, $C_{15}$, $C_{16}$, $C_{17}$, or $C_{18}$ alkyl or alkenyl.

In another embodiment, the stereoisomerically pure compound of Structural Formula (I) or (II) is a carbonate compound, wherein X is O and $R_1$ and $R_2$ are each independently a —C(O)—O—($C_1$-$C_{18}$ straight chain or branched) alkyl or a —C(O)—O—($C_2$-$C_{18}$ straight chain or branched) alkylene. In a particular embodiment, the stereoisomerically pure compound is nicotinamide riboside hydride 2',3',5'-triethylcarbonate.

In another aspect, the invention provides a pharmaceutically acceptable salt of any of the above-described stereoisomerically pure compounds, which comprises an anion such as chloride, bromide, iodide, nitrate, sulfate, sulfite, phosphate, carbonate, bicarbonate, methanesulfonate (mesylate), ethanesulfonate, propanesulfonate, benzenesulfonate (bezylate), para-toluenesulfonate (tosylate), thiocyanate, and trifluoromethanesulfonate. In further embodiments, the pharmaceutically acceptable salt comprises an anion such as trifluoroacetate, formate, acetate, propionate, butyrate, isobutyrate, pentanoate (valerate), isopentanoate, hexanoate (caproate), isohexanoate, heptanoate (enanthate), isoheptanoate, octanoate (caprylate), isooctanoate, nonanoate (pelargonate), isononanoate, decanoate (caprate), laurate, oleate, palmitate, stearate, undecylenate, benzoate, nicotinate, lactate, glucuronate, tartrate, malate, succinate, fumarate, malonate, tartarate, hydroxysuccinate, 2-oxosuccinate, 2-oxoglutarate, acetonedicarboxylate, phthalate, oxalate, adipate, glutarate, sebacate, maleate, citrate, ethylenediamine tetraacetate, aspartate, and glutamate.

In certain advantageous embodiments, the invention provides a composition of the stereoisomerically pure β-anomeric compound having Structural Formula (I) or (II), which comprises less than 5% of the α-anomeric form of the compound. In particular embodiments, the invention provides a composition of the stereoisomerically pure β-anomeric compound having Structural Formula (I) or (II), which comprises less than 1% of the α-anomeric form of the compound. In other embodiments, the invention provides a composition comprising less than 10%, 9%, 8%, 7%, 6%, 4%, 3%, 2%, or 0.5% of an α-anomeric form of the compound.

In another aspect, the invention provides a pharmaceutical or cosmetic composition that includes one or more of the above-described stereoisomerically pure compounds of Structural Formula (I) or (II), in combination with a pharmaceutically or cosmetically acceptable carrier. In particular embodiments, the pharmaceutical or cosmetic composition is is hermetically sealed to exclude oxygen, e.g., by formulation of the composition into an airtight capsule. In particular embodiments, the pharmaceutical composition is formulated for oral administration. In other embodiments, the composition is a cosmetic composition formulated for topical or dermal administration. In further embodiments, the pharmaceutical composition includes an additional pharmaceutically active agent in addition to the nicotinamide riboside ester or carbonate of Structural Formula (I) or (II).

In another aspect, the invention provides a pharmaceutical composition that includes a stereoisomerically pure β-anomeric compound represented by Structural Formula (I) or (II):

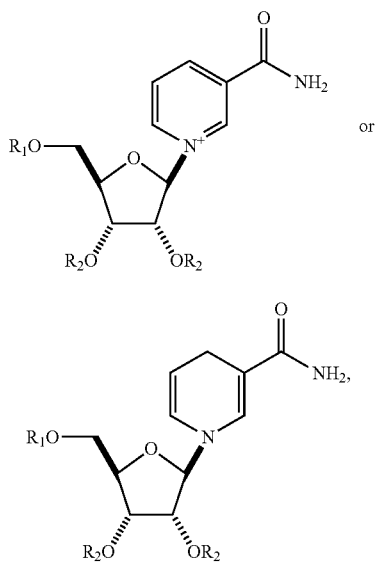

or a pharmaceutically acceptable salt thereof, wherein $R_1$ is a —C(=O)—($C_1$-$C_5$ straight chain or branched) alkyl or a —C(=O)—($C_2$-$C_5$ straight chain or branched) alkenyl, and each $R_2$ is independently selected from hydrogen, and a —C(O)—($C_1$-$C_5$ straight chain or branched) alkyl or alkylene. In particular embodiments, the pharmaceutical composition includes less than 5% of a corresponding α-anomeric compound. In other embodiments, the pharmaceutical composition includes less than 10%, 9%, 8%, 7%, 6%, 4%, 3%, 2%, or 0.5% of a corresponding α-anomeric compound. In certain embodiments, the pharmaceutical composition is pyrogen-free.

In a further aspect, the invention provides a method of treating a skin disorder or disease associated with or caused by inflammation, sun damage, or natural aging by administering a pharmaceutical composition formulated for topical administration of the invention (e.g., as described above) to the skin or mucosal tissue of a subject in need thereof. In certain embodiments, the skin disorder or disease to be treated is contact dermatitis, allergic eczema, actinic keratosis, eczema, pemphigus, exfoliative dermatitis, seborrheic dermatitis, erythema multiforme, erythema nodosum, sun damage, discoid lupus erythematosus, dermatomyositis, psoriasis, skin cancer, or the effects of natural aging. In particular embodiments, the invention provides methods of treating a wound or a burn by administering a pharmaceutical composition formulated for topical administration of the invention (e.g., as described above) to the skin or mucosal tissue of a subject in need thereof.

In a preferred aspect, the invention provides a method of elevating NAD levels in at least one tissue of a subject, by administering a pharmaceutical composition of the invention to the subject. In particular embodiments, the pharmaceutical composition is administered orally. In other embodiments, the pharmaceutical composition is administered intravenously, intraperitoneally, or intramuscularly. In further embodiments, the pharmaceutical composition is administered topically. In certain embodiments, the method of elevating NAD levels in at least one tissue of a subject involves administration of an additional agent in addition to one or more of the nicotinamide riboside esters or carbonates of Structural Formula (I) or (II), as described above.

In another aspect, the invention provides a method of treating a subject suffering from, or susceptible to, insulin resistance, a metabolic syndrome, diabetes, or complications thereof, or for increasing insulin sensitivity in a subject by administering to the subject a pharmaceutical composition comprising one or more of the nicotinamide riboside esters or carbonates of Structural Formula (I) or (II), as described above.

In a further aspect, the invention provides a method of treating a subject suffering from or susceptible to a mitochondrial disease or disorder by administering to the subject in need thereof a pharmaceutical composition that includes one or more of the nicotinamide riboside esters or carbonates of Structural Formula (I) or (II), as described above. In certain embodiments, the mitochondrial disease or disorder is Leber's hereditary optic neuropathy (LHON), mitochondrial encephalomyopathy lactic acidosis and stroke-like episodes (MELAS), myoclonic epilepsy and ragged-red fiber disease (MERRF), or Leigh syndrome (LS).

In another aspect, the invention provides a nicotinamide riboside esters or carbonates of Structural Formula (I) or (II), or pharmaceutically acceptable salts thereof, as described above, for use in therapy. In particular embodiments, the compound or pharmaceutically acceptable salt thereof is for use in the treatment of a skin disorder or disease associated with or caused by inflammation, sun damage, or natural aging; or the treatment of a wound or a burn; or elevating NAD levels in at least one tissue of a subject; or the treatment of insulin resistance, a metabolic syndrome, diabetes, or complications thereof; or for increasing insulin sensitivity; or the treatment of a mitochondrial disease or disorder. In a further embodiment, the nicotinamide riboside esters or carbonates of Structural Formula (I) or (II), or pharmaceutically acceptable salts thereof, as described above, is for use in the manufacture of a medicament for use in the treatment of a skin disorder or disease associated with or caused by inflammation, sun damage, or natural aging; or the treatment of a wound or a burn; or elevating NAD levels in at least one tissue of a subject; or the treatment of insulin resistance, a metabolic syndrome, diabetes, or complications thereof; or for increasing insulin sensitivity; or the treatment of a mitochondrial disease or disorder.

In a further aspect, the invention provides a compound represented by Structural Formula (I) or (II):

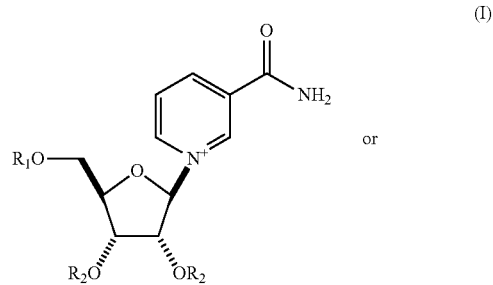

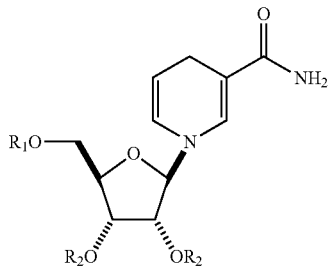

(II)

or a pharmaceutically acceptable salt thereof, where $R_1$ is —C(=O)—X—($C_1$-$C_{18}$ straight chain or branched) alkyl or —C(=O)—X—($C_2$-$C_{18}$ straight chain or branched) alkenyl; each $R_2$ is independently selected from hydrogen, and a —C(O)—X—($C_1$-$C_{18}$ straight chain or branched) alkyl or a —C(O)—X—($C_2$-$C_{18}$ straight chain or branched) alkenyl; and X is a covalent bond or O. In certain embodiments, the compound is not stereoisomerically pure. In particular embodiments, the invention provides compositions comprising these non-stereoisomerically pure compounds, particularly in a diastereomeric mixture of the compound of formula (I) or (II) (or salt thereof) and its stereoisomer. In certain embodiments, the non-stereoisomerically pure compound of Structural Formula (I) or (II) comprises an $R_1$ and/or $R_2$ that is —C(=O)—X—($C_1$-$C_{10}$ straight chain or branched) alkyl or —C(=O)—X—($C_2$-$C_{10}$ straight chain or branched) alkenyl. In particular embodiments, the non-stereoisomerically pure compound comprises a straight chain or branched alkyl or alkenyl that is a $C_1$, $C_2$, $C_3$, $C_4$, $C_5$, $C_6$, $C_7$, $C_8$, $C_9$, or $C_{10}$ alkyl, or a $C_2$, $C_3$, $C_4$, $C_5$, $C_6$, $C_7$, $C_8$, $C_9$, or $C_{10}$ alkenyl. In other embodiments, the non-stereoisomerically pure compound of Structural Formula (I) or (II) comprises an $R_1$ and/or $R_2$ that is —C(=O)—X—($C_{11}$-$C_{18}$ straight chain or branched) alkyl or alkenyl. In particular embodiments, the non-stereoisomerically pure compound comprises a straight chain or branched alkyl or alkenyl that is a $C_{11}$, $C_{12}$, $C_{13}$, $C_{14}$, $C_{15}$, $C_{16}$, $C_{17}$, or $C_{18}$ alkyl or alkenyl.

BRIEF DESCRIPTION OF THE FIGURES

FIG. 9B is a table summarizing the structures and other physical properties of the compounds used in the study shown in FIG. 9A.

DETAILED DESCRIPTION OF THE INVENTION

The present invention is directed to nicotinamide riboside ester and carbonate analogs, along with their uses, e.g., as prodrug forms of nicotinamide riboside for the elevation of $NAD^+$ in a subject.

NAD and its phosphorylated analog, NADP, are indispensable cofactors for numerous oxidoreductases in all living organisms (Moat and Foster, 1987). NAD and NADP also serve as cofactors for enzymes that do not appear to be involved in oxidation or reduction. For example, sirtuins, a conserved family of protein deacetylases that include Sir2 and Sir2-related enzymes, require NAD for their activity as transcriptional silencers. This NAD-dependent deacetylation activity is believed to cause alterations in gene expression, repression of ribosomal DNA recombination, and the health benefits and lifespan extension provided by calorie restriction. Accordingly, compounds that are capable of modulating sirtuin activity may be useful in a variety of medical conditions in mammals (e.g., mice and humans), such as those that are caused by or associated with changes in gene expression and age of the individual. These medical conditions include disorders related to aging or stress, diabetes, obesity, neurodegenerative diseases, cardiovascular disease, blood clotting disorders, inflammation, cataracts, flushing, cell death, cancer, appetite, and/or weight gain.

Figure 1:
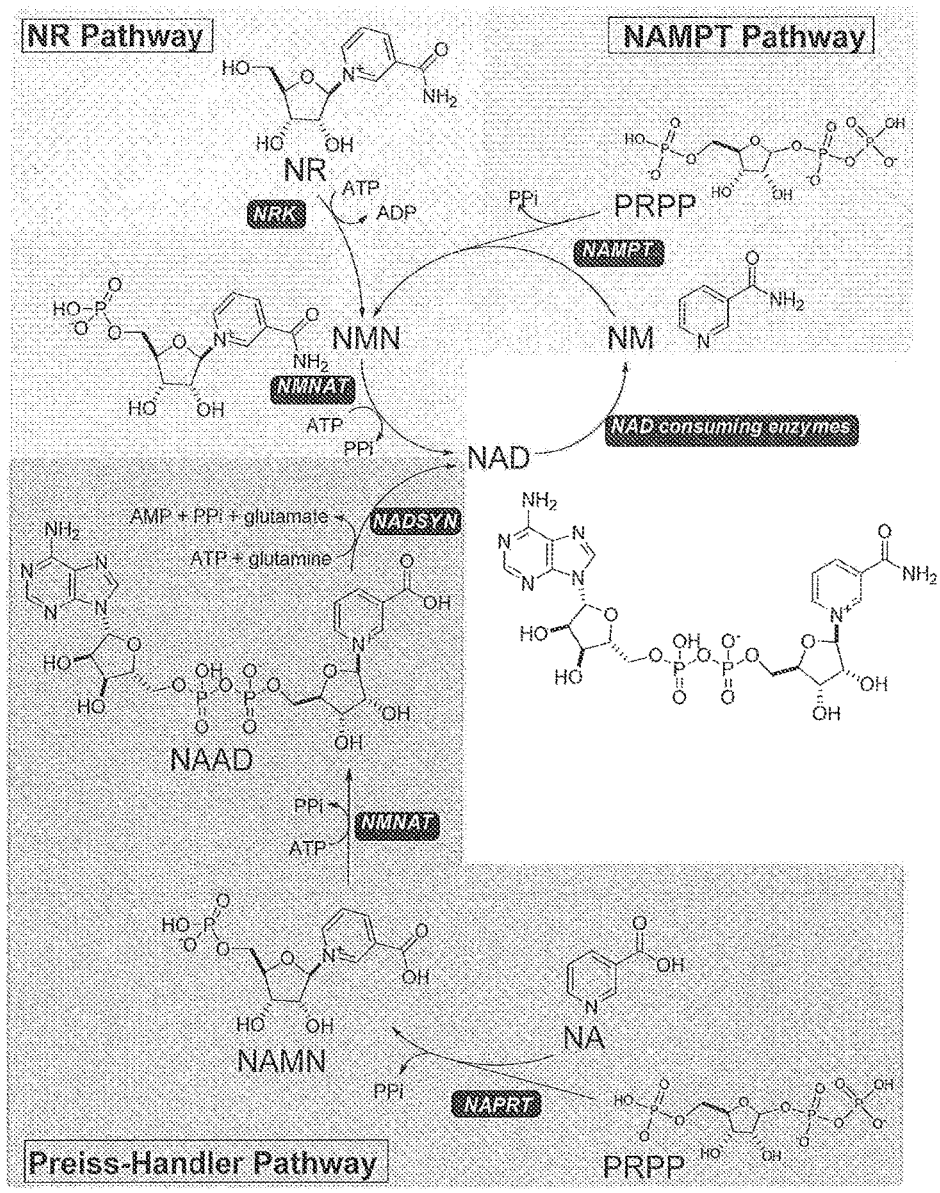
FIG. 1 depicts the NAD biosynthetic pathways affecting NAD metabolism including the Preiss-Handler pathway for niacin incorporation, the NR pathway utilizing exogenous NR, and the NAMPT pathway for nicotinic acid incorporation. The different biosynthetic pathways are shaded and labeled accordingly. Abbreviations of depicted compounds: ADP—adenosine diphosphate; ATP—adenosine triphosphate; NA—nicotinic acid; NAAD—nicotinic acid adenine dinucleotide; NAD—nicotinamide adenine dinucleotide; NAMN—nicotinic acid mononucleotide; NM—nicotinamide; NMN—nicotinamide mononucleotide NR—nicotinamide riboside; PRPP—5-phosphoribose-1-pyrophosphate; PPi—pyrophosphate. Enzyme Abbreviations: NAD consuming enzymes include ADPribosyl transferases, poly-ADPribosyl transferases, and sirtuins; NADSYN—NAD synthetase; NAPRT—nicotinic acid phosphoribosyl transferase; NAMPT—nicotinamide phosphoribosyltransferase; NMNAT—nicotinamide mononucleotide adenyl transferase.
Figure 2:
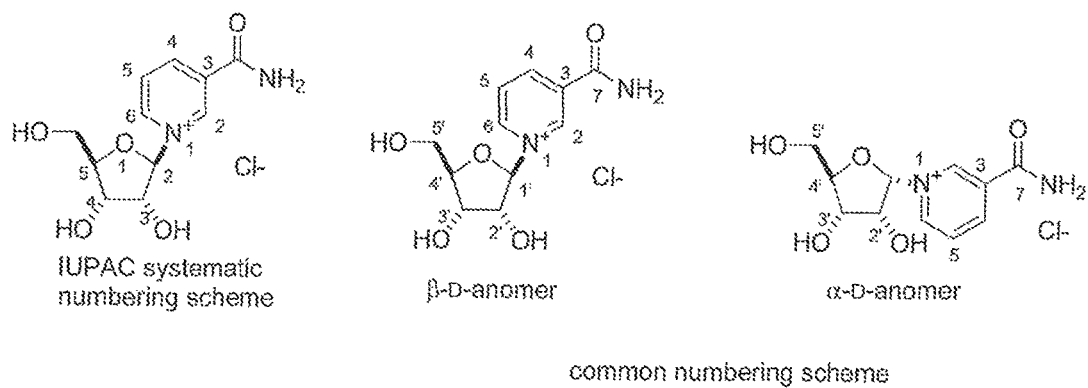
FIG. 2 depicts the chemical structure and numbering scheme of nicotinamide riboside.

NAD can be synthesized de novo from tryptophan via the kynurenine pathway (Krehl et al., 1945; Schutz and Feigelson, 1972) or by salvaging nicotinic acid that is imported extracellularly (see FIG. 1). Furthermore, nicotinic acid can be deamidated from nicotinamide in yeast (Panozzo et al., 2002; Anderson et al., 2003; Gallo et al., 2004), although this pathway does not appear to be conserved in humans. Instead, it is thought that humans utilize pre-B-cell colony enhancing factor (PBEF) to synthesize nicotinamide mononucleotide (NMN), which is a precursor to NAD. An alternate NAD biosynthetic pathway appears to be conserved in humans and yeast. In this pathway, nicotinamide riboside is phosphorylated to generate NMN, which in turn is used to generate NAD. The nicotinamide riboside ester and carbonate analogs of the invention are designed to provide bioavailable and stable prodrug forms of nicotinamide riboside that are effective at $NAD^+$ elevation in desired tissue(s) while avoiding major adverse effects on $NAD^+$-dependent biological processes.

1. Definitions

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

The term "bioavailable", when referring to a compound, is art-recognized and refers to a form of a compound that allows for all or a portion of the amount of compound administered to be absorbed by, incorporated into, or otherwise physiologically available to a subject or patient to whom it is administered.

"Biologically active portion of a sirtuin" refers to a portion of a sirtuin protein having a biological activity, such as the ability to deacetylate ("catalytically active"). Catalytically active portions of a sirtuin may contain, but are not limited to, the core domain of sirtuins. Catalytically active portions of SIRT1 having GenBank Accession No. NP_036370 that encompass the $NAD^+$ binding domain and the substrate binding domain, for example, may include without limitation, amino acids 240-664 or 240-505 of GenBank Accession No. NP_036370, which are encoded by the polynucleotide of GenBank Accession No. NM_012238. Therefore, this region is sometimes referred to as the core domain. Other catalytically active portions of SIRT1, also sometimes referred to as core domains, include about amino acids 242 to 493 of GenBank Accession No. NP_036370, which are encoded by nucleotides 777 to 1532 of GenBank Accession No. NM 012238, or about amino acids 240 to 505 of GenBank Accession No. NP_036370, which are encoded by the polynucleotide of GenBank Accession No. NM_012238. Another "biologically active" portion of SIRT1 is amino acids 183-225 of GenBank Accession No. NP_036370, which comprise a domain N-terminal to the core domain that is important to the compound binding site.

Catalytically active portions of SIRT2 having GenBank Accession No. NP_036369.2 that encompass the $NAD^+$ binding domain and the substrate binding domain, for example, may include without limitation, amino acids 57-356 of GenBank Accession No. NP_036369.2, which are encoded by the polynucleotide of GenBank Accession No. NM_012237.3. Therefore, this region is sometimes referred to as the core domain.

Catalytically active portions of SIRT3 having GenBank Accession No. NP_036371.1 that encompass the $NAD^+$ binding domain and the substrate binding domain, for example, may include without limitation, amino acids 118-399 of GenBank Accession No. NP_036371.1, which are encoded by the polynucleotide of GenBank Accession No. NM_012239.5. Therefore, this region is sometimes referred to as the core domain.

The term "mammal" is known in the art, and exemplary mammals include humans, primates, livestock animals (including bovines, porcines, etc.), companion animals (e.g., canines, felines, etc.) and rodents (e.g., mice and rats).

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

The term "$ED_{50}$" refers to the art-recognized measure of effective dose. In certain embodiments, $ED_{50}$ means the dose of a drug which produces 50% of its maximum response or effect, or alternatively, the dose which produces a predetermined response in 50% of test subjects or preparations, such as isolated tissue or cells. The term "$LD_{50}$" art-recognized measure of lethal dose. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "$IC_{50}$" is art-recognized and refers to the dose of a drug which produces 50% of its maximum response or effect. In other words, it is the half maximal inhibitory concentration of a drug.

The term "naturally occurring form" when referring to a compound means a compound that is in a form, e.g., a composition, in which it can be found naturally. For example, since nicotinamide riboside has been report to be found in milk, it is present in milk in a form that is naturally occurring. A compound is not in a form that is naturally occurring if, e.g., the compound has been chemically modified.

A "naturally occurring compound" refers to a compound that can be found in nature, i.e., a compound that has not been designed by man. A naturally occurring compound may have been made by man or by nature. For example, nicotinamide riboside has been reported to be present in milk, and is therefore a naturally occurring compound. A "non-naturally occurring compound" is a compound that is not known to exist in nature or that does not occur in nature.

A "patient", "subject", "individual" or "host" refers to either a human or a non-human animal.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephritic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

"Mitochondrial disease" refers to disorders to which deficits in mitochondrial respiratory chain activity contribute in the development of pathophysiology of such disorders in a mammal. This category includes 1) congenital genetic deficiencies in activity of one or more components of the mitochondrial respiratory chain; 2) acquired deficiencies in the activity of one or more components of the mitochondrial respiratory chain, wherein such deficiencies are caused by, inter alia, a) oxidative damage during aging; b) elevated intracellular calcium; c) exposure of affected cells to nitric oxide; d) hypoxia or ischemia; e) microtubule-associated deficits in axonal transport of mitochondria, or f) expression of mitochondrial uncoupling proteins. Diseases related to mitochondrial respiratory chain dysfunction can be divided into several categories based on the origin of mitochondrial defects. Congenital mitochondrial diseases are those related to hereditary mutations, deletions, or other defects in mitochondrial DNA or in nuclear genes regulating mitochondrial DNA integrity, or in nuclear genes encoding proteins that are critical for mitochondrial respiratory chain function. Acquired mitochondrial defects comprise primarily 1) damage to mitochondrial DNA due to oxidative processes or aging; 2) mitochondrial dysfunction due to excessive intracellular and intramitochondrial calcium accumulation; 3) inhibition of respiratory chain complexes with endogenous or exogenous respiratory chain inhibitors; 4) acute or chronic oxygen deficiency; and 5) impaired nuclear-mitochondrial interactions, e.g. impaired shuttling of mitochondria in long axons due to microtubule defects, and 6) expression of mitochondrial uncoupling proteins in response to lipids, oxidative damage or inflammation. A number of clinical syndromes have been linked to mutations or deletions in mitochondrial DNA. Mitochondrial DNA is inherited maternally, with virtually all of the mitochondria in the body derived from those provided by the oocyte. Some consistent symptom patterns have emerged in conjunction with identified mitochondrial DNA defects, and these comprise the classic "mitochondrial diseases", some of which are listed immediately below. Nonetheless, an important aspect of the subject invention is the recognition that the concept of mitochondrial disease and its treatment with compounds and compositions of the invention extends to many other disease conditions which are also disclosed herein. Some of the classical phenotypes of major mitochondrial diseases associated with mutations or deletions of mitochondrial DNA include: MELAS (Mitochondrial Encephalomyopathy Lactic Acidemia, and Stroke-like episodes); MERRF (Myoclonic Epilepsy with "Ragged Red" (muscle) Fibers); MNGIE (Mitochondrial neurogastrointestinal encephalomyopathy); NARP (Neurogenic muscle weakness, Ataxia and Retinitis Pigmentosa); LHON (Leber's Hereditary Optic Neuropathy); Leigh's Syndrome (Subacute Necrotizing Encephalomyopathy); PEO (Progressive External Opthalmoplegia); Kearns-Sayres Syndrome (PEO, pigmentary retinopathy, ataxia, and heart-block). Other common symptoms of mitochondrial diseases which may be present alone or in conjunction with these syndromes include cardiomyopathy, muscle weakness and atrophy, developmental delays (involving motor, language, cognitive or executive function), ataxia, epilepsy, renal tubular acidosis, peripheral neuropathy, optic neuropathy, autonomic neuropathy, neurogenic bowel dysfunction, sensorineural deafness, neurogenic bladder dysfunction, dilating cardiomyopathy, migraine, hepatic failure, lactic acidemia, and diabetes mellitus. Diagnosis of congenital mitochondrial disease is challenging, due to the heterogeneity of symptoms, even between patients affected with the same molecular defect. Deficits in cell and tissue function due to mitochondrial dysfunction can mimic tissue dysfunction caused by problems that do not directly involve mitochondrial defects. Several clinically useful and practical schemes for diagnosis of mitochondrial diseases are known in the art; they typically involve several major criteria (e.g. classical clinical phenotypes like MELAS, NARP or Leigh's Syndrome, extreme (>80%) depressions of respiratory chain complex activity in fresh tissue samples) with a good degree of certainty in establishing the role of respiratory chain dysfunction in disease pathogenesis, and a larger number of minor criteria (e.g. moderate biochemical abnormalities characteristic of respiratory chain defects, symptoms characteristic of mitochondrial diseases without full presentation of one of the classical phenotypes listed above) which individually are less compelling than single major criteria, but which cumulatively provide strong evidence for the contribution of respiratory chain deficits to a particular patient's clinical presentation, as described in Walker et al. (Eur Neurol., 36:260-7, 1996).

"Obese" individuals or individuals suffering from obesity are generally individuals having a body mass index (BMI) of at least 25 or greater. Obesity mayor may not be associated with insulin resistance.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Further suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by micronization, for instance in view to obtain them in the form of microspheres usually having a diameter of about 1 to 10 gm, namely for the manufacture of microcapsules for controlled or sustained release of the active ingredients.

The term "pharmaceutically acceptable salts" as used herein means the therapeutically active non-toxic salt forms which the carbohydrate binding compounds described herein are able to form. Therefore, the compounds of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing Li$^+$, Na$^+$, and K$^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the carbohydrate binding compounds described herein as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates. Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine. The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and NX4$^+$ (wherein X is C$_1$-C$_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as Na$^+$ and NX4$^+$ (wherein X typically is independently selected from H or a C$_1$-C$_4$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

The term "preventing" is art-recognized, and when used in relation to a condition, such as inflammation and associated pain, diabetes, metabolic disease and/or weight gain or any other medical condition, is well understood in the art, and includes administration of a composition which reduces the frequency of, or delays the onset of, symptoms of a medical condition in a subject relative to a subject which does not receive the composition. Thus, prevention of an inflammatory condition includes, for example, reducing the incidence of an inflammatory condition in a population of patients receiving a prophylactic treatment relative to an untreated control population, and/or delaying the appearance of the inflammatory condition in a treated population versus an untreated control population, e.g., by a statistically and/or clinically significant amount.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

"Sirtuin-modulating compound" refers to a compound that is either a sirtuin inhibitor compound or a sirtuin activator compound.

"Sirtuin-activating compound" or "sirtuin activator compound" refers to a compound that increases the level of a sirtuin protein and/or increases at least one activity of a sirtuin protein. In an exemplary embodiment, a sirtuin-activating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; mitotic regulation and controlling the segregation of oxidized proteins between mother and daughter cells.

"Sirtuin-inhibiting compound" or "sirtuin inhibitor compound" refers to a compound that decreases the level of a sirtuin protein and/or decreases at least one activity of a sirtuin protein. In an exemplary embodiment, a sirtuin-inhibiting compound may decrease at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

"Sirtuin protein" refers to a member of the sirtuin deacetylase protein family, or preferably to the sir2 family, which include yeast Sir2 (GenBank Accession No. P53685), *C. elegans* Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273).

"SIRT1 protein" refers to a member of the sir2 family of sirtuin deacetylases. In certain embodiments, a SIRT1 protein includes yeast Sir2 (GenBank Accession No. P53685), *C. elegans* Sir-2.1 (GenBank Accession No. NP_501912), human SIRT1 (GenBank Accession No. NM_012238 or NP_036370 (or AF083106)), mouse SIRT1 (GenBank Accession No. NM_019812 or NP_062786), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof.

Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein", "SIRT3 protein", "SIRT4 protein", SIRT5 protein", "SIRT6 protein", and "SIRT7 protein" refer to other mammalian, e.g. human, sirtuin deacetylase proteins that are homologous to SIRT1 protein, particularly in the approximately 275 amino acid conserved catalytic domain. For example, "SIRT3 protein" refers to a member of the sirtuin deacetylase protein family that is homologous to SIRT1 protein. In certain embodiments, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In certain embodiments, a SIRT4 protein includes human SIRT4 (GenBank Accession No. NM_012240 or NP_036372). In certain embodiments, a SIRT5 protein includes human SIRT5 (GenBank Accession No. NM_012241 or NP_036373). In certain embodiments, a SIRT6 protein includes human SIRT6 (GenBank Accession No. NM_016539 or NP_057623). In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In certain embodiments, a SIRT3 protein includes a fragment of SIRT3 protein that is produced by cleavage with a mitochondrial matrix processing peptidase (MPP) and/or a mitochondrial intermediate peptidase (MIP).

The terms "systemic administration" and "administered systemically," are art-recognized and refer to the administration of a subject composition, therapeutic or other material enterally or parenterally.

The term "therapeutic agent" is art-recognized and refers to any biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a beneficial local or systemic effect in animals, particularly mammals, and more particularly humans, caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of skill in the art. For example, certain compositions described herein may be administered in a sufficient amount to produce a desired effect at a reasonable benefit/risk ratio applicable to such treatment.

"Treating" a condition or disease refers to curing as well as ameliorating at least one symptom of the condition or disease.

An "alkyl" group or "alkane" is a straight chained or branched non-aromatic hydrocarbon which is completely saturated. Typically, a straight chained or branched alkyl group has from 1 to about 20 carbon atoms, with a "lower alkyl" having from 1 to about 10 unless otherwise defined, and a "higher alkyl" having from 11 to 18 carbon atoms, unless otherwise defined. Examples of $C_1$-$C_{18}$ straight chained or branched alkyl groups include methyl, ethyl, n-propyl, iso-propyl, n-butyl, sec-butyl, tert-butyl, pentyl, neopentyl, hexyl, isohexyl, isopentyl, octyl nonyl, decyl, undecyl, dodecyl, tridecyl, tetradecyl, pentadecyl, hexadecyl, heptadecyl, and octadecyl. A $C_1$-$C_4$ straight chained or branched alkyl group is also referred to as a "lowest alkyl" group.

The terms "alkenyl" ("alkene") and "alkynyl" ("alkyne") refer to unsaturated aliphatic groups analogous in length and possible substitution to the alkyl groups described above, but that contain at least one double or triple bond respectively.

A "cycloalkyl" group is a cyclic hydrocarbon which is completely saturated (non-aromatic). Typically, a cycloalkyl group has from 3 to about 10 carbon atoms, more typically 3 to 8 carbon atoms unless otherwise defined. A "cycloalkenyl" group is a cyclic hydrocarbon containing one or more double bonds.

A "halogen" designates F, Cl, Br or I.

A "halogen-substitution" or "halo" substitution designates replacement of one or more hydrogens with F, Cl, Br or I.

As used herein, "substituted" means substituting a hydrogen atom in a structure with an atom or molecule other than hydrogen. A substitutable atom such as a "substitutable nitrogen" is an atom that bears a hydrogen atom in at least one resonance form. The hydrogen atom may be substituted for another atom or group such as a $CH_3$ or an OH group.

For example, the nitrogen in a piperidine molecule is substitutable if the nitrogen is bound to a hydrogen atom. If, for example, the nitrogen of a piperidine is bound to an atom other than hydrogen, the nitrogen is not substitutable. An atom that is not capable of bearing a hydrogen atom in any resonance form is not substitutable.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

The compounds disclosed herein also include partially and fully deuterated variants.

In certain embodiments, deuterated variants may be used for kinetic studies. One of skill in the art can select the sites at which such deuterium atoms are present.

Also included in the present invention are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt.

Alternatively, compounds that are inherently charged, such as those with a quarternary nitrogen, can form a salt with an appropriate counterion (e.g., a halide such as bromide, chloride, or fluoride, particularly bromide).

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 95, 96, 97, 98, or 99%.

The term "isomers" as used herein means all possible isomeric forms, including tautomeric and sterochemical forms, which the carbohydrate binding compounds described herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the carbohydrate binding compounds described herein may have at least one chiral center) of the basic molecular structure, as well as the stereochemically pure or enriched compounds. More particularly, stereogenic centers may have either the R- or S-configuration, and multiple bonds may have either cis- or trans-configuration.

Certain compounds of the present invention may exist in particular geometric or stereoisomeric form, including cis- and trans-isomers, (R)- and (S)-enantiomers, diastereomers, (D)-isomers, (L)-isomers, the racemic mixtures thereof, and other mixtures thereof. Additional asymmetric carbon atoms may be present in a substituent such as an alkyl group. Such isomers, as well as mixtures thereof, are intended to be included in this invention.

The term "stereoisomer" as used herein is art-recognized and refers to any of two or more isomers that have the same molecular constitution and differ only in the three-dimensional arrangement of their atomic groupings in space. When used herein to describe a compounds or genus of compounds, stereoisomer includes any portion of the compound or the compound in its entirety. For example, diastereomers and enantiomers are stereoisomers.

The term "stereoisomerically pure" refers to the pure isomeric forms of the referenced compounds and are defined as isomers substantially free of other enantiomeric or diastereomeric forms of the same basic molecular structure. In particular, the term "stereoisomerically pure" or "chirally pure" relates to compounds having a stereoisomeric excess of at least about 90% (i.e. at least 90% of one isomer and at most 10% of the other possible isomers), preferably at least 95%, more preferably at least 97% and most preferably at least 99%. The terms "enantiomerically pure" and "stereomerically pure" should be understood in a similar way, having regard to the enantiomeric excess, respectively the diastereomeric excess, of the mixture in question. Separation of stereoisomers is accomplished by standard methods known to those in the art. One enantiomer of a carbohydrate binding compounds described herein can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched compounds of the invention. A method of determining optical purity involves making chiral esters, such as a menthyl ester or Mosher ester, alpha-methoxy-alpha-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylase derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The term "tautomer" as used herein is art-recognized and refers to any one of the possible alternative structures that may exist as a result of tautomerism, which refers to a form of constitutional isomerism in which a structure may exist in two or more constitutional arrangements, particularly with respect to the position of hydrogens bonded to oxygen.

When used herein to describe a compound or genus of compounds, it is further understood that a "tautomer" is readily interconvertible and exists in equilibrium. For example, keto and enol tautomers exist in proportions determined by the equilibrium position for any given condition, or set of conditions.

The term "substantially free" means that the volume of the object that the formulation is free from, e.g. surfactant, water, etc. in that phase or final formulation is less than 10% of the volume or total volume. In one embodiment the volume is less than 5% of volume or total volume. In another embodiment the volume is less than 1% of the volume of the phase or the total volume, as appropriate.

As used herein, the term "about" indicates a deviation of +/−10% of the given value, preferably +/−5% and most preferably +/−2% of the numeric values, when applicable.

As used herein the terms "active agent", "drug moiety" or "drug" are all used interchangeably. The terms "mold" and "mould" are also used interchangeably herein.

2. Compounds and Compositions

In one aspect, compounds of the present invention, or compositions comprising compounds of the present invention may be used for treating and/or preventing diseases and disorders including cancers, neurodegenerative diseases, and inflammatory disorders and conditions. Compounds disclosed herein may be suitable for use in pharmaceutical compositions and/or one or more methods disclosed herein.

The invention provides racemic and stereoisomerically pure nicotinamide riboside analogues, including esters and carbonates compounds having Structural Formulas (I) or Structural Formula (II), as well as a pharmaceutically acceptable salt thereof, as shown below:

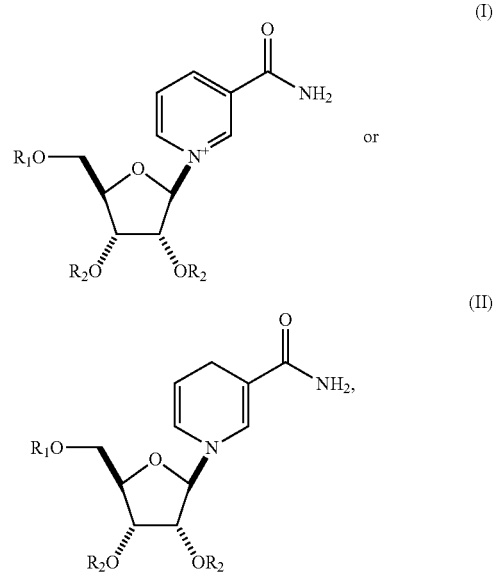

where $R_1$ is $-C(=O)-X-(C_1-C_{18}$ straight chain or branched) alkyl or $-C(=O)-X-(C_2-C_{18}$ straight chain or branched)alkenyl, each $R_2$ is independently selected from hydrogen, and a $-C(O)-X-(C_1-C_{18}$ straight chain or branched) alkyl or a $-C(O)-X-(C_2-C_{18}$ straight chain or branched) alkenyl; and X is a covalent bond (in the case of esters) or O (in the case of carbonates). Structural Formula (I) corresponds to compounds comprising a reduced nicotinamide moiety, and Structural Formula (II) corresponds to compounds comprising an oxidized nicotinamide moiety.

In certain embodiments, compounds having Structural Formula A are excluded from the compounds, pharmaceutical compositions and/or methods of the invention:

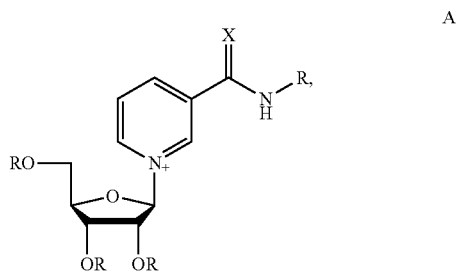

wherein R represents independently, for each occurrence, H, benzoyl, phosphate, sulfate, (alkyoxy)methyl, triarylmethyl, (trialkyl)silyl, (dialkyl)(aryl)-silyl,(alkyl)(diaryl)silyl, or (triaryl)silyl; and R on the amide nitrogen of the nicotinamide moiety represents R, acetyl, acyl, benzoyl, acyl, phosphate, sulfate, (alkyoxy)methyl, triarylmethyl, (trialkyl)silyl, (dialkyl)(aryl)silyl,(alkyl)(diaryl)silyl, or (triaryl)silyl; and X represents O or S. In other embodiments, the excluded compounds of Formula A include nicotinamide riboside analogs in which, independently for each occurrence, R is acyl, e.g. acetyl or other $C_{14}$ alklyl. In particular embodiments, the excluded compounds of Formula A include nicotinamide riboside analogs in which any of the three R groups, independently of their occurrence directly on the ribose ring, is acyl, e.g. acetyl or other $C_1$-4 alklyl.

While it is possible for nicotinamide riboside esters and analogs of the invention to be administered alone, it may also be presented as a pharmaceutical formulation. Accordingly, the present invention further provides a pharmaceutical formulation comprising nicotinamide riboside esters and analogs of the invention and a pharmaceutically acceptable carrier or excipient, and optionally one or more other therapeutic ingredients.

The term "active ingredient," as used hereafter, means one or more of the nicotinamide riboside ester and carbonate analogues of the invention, unless the context dictates otherwise.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Each capsule or cartridge may generally contain between 20 mg-10 g of the active ingredient optionally in combination with another therapeutically active ingredient.

Alternatively, the compound of the invention may be presented without excipients. Packaging of the formulation may be suitable for unit dose or multi-dose delivery.

Preferred unit dosage formulations are those containing an effective dose, as hereinbefore recited, or an appropriate fraction thereof, of the active ingredient.

It should be understood that in addition to the active ingredients particularly mentioned above, the formulations of this invention may include other agents conventional in the art having regard to the type of formulation in question, for example those suitable for oral administration may include flavoring agents.

The compound and pharmaceutical formulations according to the invention may be used in combination with or include one or more other therapeutic agents, for example selected from other NAD precursors, such as nicotinamide mononucleotide (NMN), nicotinamide riboside and/or niacin (nicotinic acid or vitamin B3). The invention provides, in a further aspect, a combination comprising a nicotinamide riboside ester or carbonate analog of the invention together with one or more other therapeutically active agents, for example selected from an anti-inflammatory agent (for example a corticosteroid or an NSAID).

In certain embodiments, the pharmaceutical or cosmetic composition is formulated for topical administration. For example, suitable pharmaceutical carriers for topical administration include water, alcohol, glycerin, mineral oil, silicone, petroleum jelly, lanolin, fatty acids, vegetable oil, paraben, wax, or polyethylene glycol (PEG), or a combination of these carriers. Suitable pharmaceutical carriers formulated for topical administration may be in the form of an ointment, a lotion, a cream, a microemulsion, a gel, an oil, or a solution.

The pharmaceutical or cosmetic composition for topical administration may optionally include an additional active agent selected from an anti-inflammatory agent, an analgesic agent, an antimicrobial agent, an antifungal agent, an antibiotic agent, a vitamin, an antioxidant agent, and a sunblock agent.

3. Pharmaceutical and Cosmetic Compositions

The compounds described herein may be formulated in a conventional manner using one or more physiologically or pharmaceutically acceptable carriers or excipients. For example, compounds and their pharmaceutically acceptable salts and solvates may be formulated for administration by, for example, oral, or injection (e.g. SubQ, IM, IP), inhalation or insufflation (either through the mouth or the nose), buccal, sublingual, transdermal, nasal, parenteral, rectal or topical administration. In certain embodiments, a compound may be administered locally, at the site where the target cells are present, i.e., in a specific tissue, organ, or fluid (e.g., skin, blood, cerebrospinal fluid, etc.).

The compounds can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-para-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, compounds may also be formulated as a depot preparation. Such long acting formulations may be administered by implantation (for example subcutaneously or intramuscularly) or by intramuscular injection.

Thus, for example, compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Liposomes are a further drug delivery system which is easily injectable. Accordingly, in the method of invention the active compounds can also be administered in the form of a liposome delivery system. Liposomes are well known by those skilled in the art. Liposomes can be formed from a variety of phospholipids, such as cholesterol, stearylamine of phosphatidylcholines. Liposomes usable for the method of invention encompass all types of liposomes including, but not limited to, small unilamellar vesicles, large unilamellar vesicles and multilamellar vesicles.

Another way to produce a formulation, particularly a solution, of a compound described herein, is through the use of cyclodextrin. By cyclodextrin is meant alpha-, beta-, or gamma-cyclodextrin. Cyclodextrins are described in detail in Pitha et al., U.S. Pat. No. 4,727,064, which is incorporated herein by reference. Cyclodextrins are cyclic oligomers of glucose; these compounds form inclusion complexes with any drug whose molecule can fit into the lipophile-seeking cavities of the cyclodextrin molecule.

Rapidly disintegrating or dissolving dosage forms are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets. Additionally, fast melt dosage forms circumvent drawbacks associated with, for example, chewable dosage forms, wherein the length of time an active agent remains in a patient's mouth plays an important role in determining the amount of taste masking and the extent to which a patient may object to throat grittiness of the active agent.

Pharmaceutical compositions (and also including cosmetic preparations) may comprise from about 0.00001 to 100% such as from 0.001 to 10% or from 0.1% to 5% by weight of one or more compounds described herein. In other embodiments, the pharmaceutical or cosmetic composition comprises: (i) 0.05 to 1000 mg of the compounds of the invention, or a pharmaceutically acceptable salt thereof, and (ii) 0.1 to 2 grams of one or more pharmaceutically acceptable excipients.

In some embodiments, a compound described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

In certain embodiments, the pharmaceutical or cosmetic composition is formulated for topical administration. For example, suitable pharmaceutical carriers for topical administration include water, alcohol, glycerin, mineral oil, silicone, petroleum jelly, lanolin, fatty acids, vegetable oil, paraben, wax, or polyethylene glycol (PEG), or a combination of these carriers. Suitable pharmaceutical carriers formulated for topical administration may be in the form of an ointment, a lotion, a cream, a foam, an emulsion (o/w) or (w/), and aqueous solution, a non-aqueous solution, an aqueous gel, or a non-aqueous gel.

"Pharmaceutically acceptable agents" includes, but is not limited to, drugs, proteins, peptides, nucleic acids, nutritional agents, as described herein. This term includes therapeutic active agents, bioactive agents, active agents, therapeutic agents, therapeutic proteins, diagnostic agents, or drug(s) as defined herein, and follows the guidelines from the European Union Guide to Good Manufacturing Practice (GMP). Such substances are intended to furnish pharmacological activity or other direct effect in the diagnosis, cure, mitigation, treatment, or prevention of a disease or to affect the structure and function of the body. The substances use may be in a mammal, or may be in a human. The pharmaceutical or cosmetic compositions described herein may optionally comprise one or more pharmaceutically acceptable active agents, bioactive agents, active agents, therapeutic agents, therapeutic proteins, diagnostic agents, or drug(s) or ingredients distributed within. Water solubility of an active agent is defined by the United States Pharmacoepia. Therefore, active agents which meet the criteria of very soluble, freely soluble, soluble and sparingly soluble as defined therein are encompassed this invention.

Suitable drug substances can be selected from a variety of known classes of drugs including, but not limited to, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, phosphodiesterase inhibitors, neurokinin inhibitors, CSBP/RK/p38 inhibitors, antipsychotics, vasodilators and xanthines.

Preferred drug substances include those intended for topical and oral administration. In one embodiment the drug substance is for use topically. A description of these classes of drugs and a listing of species within each class can be found in Martindale, The Extra Pharmacopoeia, Twenty-ninth Edition, The Pharmaceutical Press, London, 1989, the disclosure of which is hereby incorporated herein by reference. These drug substances are commercially available and/or can be prepared by techniques known in the art.

Combinations of active ingredients are also within the scope of the present invention.

Drug substances or pharmaceutically or cosmetically acceptable agents (as can be used interchangeably herein) can be highly potent and/or toxic compounds with small or narrow therapeutic windows. The drug or drugs will be present in an amount needed to generate a pharmacological effect in the targeted tissue, such as by application to the skin.

According to an embodiment of the invention, said drug is present in an amount of about 0.01 to about 30% by weight based on the total weight of the composition.

In one embodiment the drug substance is suitable for nutritional or cosmetic use.

In another embodiment the drug substance is an oil-soluble UV filter substance, a deodorant or antiperspirant, an antioxidant, an insect repellent, a vitamin, or an antimicrobial agent.

In one embodiment the drug substance is one or more cosmetically or pharmaceutically acceptable oil-soluble UV filter substances.

As used herein, the term "non-aqueous" and "water-free" solvent system means that no water is specifically added to a formulation as described herein. The terms "water-free" and "non-aqueous" do not exclude the presence of trace amounts of water present in the formulation, such as less than 5%, preferably less than 3% starting materials, and more preferably less than 1% w/w.

The pharmaceutical or cosmetic composition for topical administration may optionally include an additional active agent selected from an anti-inflammatory agent, an analgesic agent, an antimicrobial agent, an antifungal agent, an antibiotic agent, a vitamin, an antioxidant agent, and a sunblock agent.

The compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing.

The compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type.

The compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

The compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9).

The compounds may be incorporated into gel formulations, which generally are semisolid systems consisting of either suspensions made up of small inorganic particles (two-phase systems) or large organic molecules distributed substantially uniformly throughout a carrier liquid (single phase gels). Although gels commonly employ aqueous carrier liquid, alcohols and oils can be used as the carrier liquid as well.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Diseases and disorders of the skin including eczema, psoriasis, allergic dermatitis, neurodermatitis, pruritis and hypersensitivity reactions, as well as photoaging, discoloration or wrinkling of the skin can be treated or prevented by, e.g., topical administration of the pharmaceutical or cosmetic compositions of the invention. A topical pharmaceutical agent may have a nicotinamide riboside ester or carbonate compound that is between about 0.001% to about 10% by weight. Preferably, the active nicotinamide riboside agent is between about 0.01% and about 3% by weight. The pharmaceutical or cosmetic composition may further comprise an optional agent such as, for example, antioxidants, sunscreens, vitamins, a pH stabilizer, or a combination of these agents. The topical pharmaceutical agent may be formulated to provide an increase in NAD levels in the skin cells of a subject by at least about 50% over an untreated subject (e.g., increasing the intracellular NAD concentration by, for example, by 100% over an untreated subject. Skin cells include fibroblasts and/or keratinocytes. The administration may be applied topically, intradermally or subcutaneously.

Topical administration may be via dermal patch or slow release mechanism to the layer of skin of the mammal. In addition, the administration may be oral or parenteral. Transdermal delivery may also be used to administer the nicotinamide riboside ester or carbonate compounds of the invention.

Pharmaceutically acceptable carriers may be any carrier known in the field as suitable for pharmaceutical (i.e., topical, oral, and parenteral) application. Preferred pharmaceutical carriers for topical (transdermal, or transmucosal administration) include, for example, emollients, humectants, thickeners, silicones and water. Pharmaceutically acceptable excipients for introducing the nicotinamide riboside ester and carbonate compounds of the invention to the bloodstream by other than injection routes can be found in Remington's Pharmaceutical Sciences (19th ed.) (Genarro, ed. (1995) Mack Publishing Co., Easton, Pa.). Specific examples of carriers include hydrocarbon oils and waxes such as mineral oil, petrolatum, paraffin, ceresin, ozokerite, microcrystalline wax, polyethylene, and perhydrosqualene; triglyceride such as vegetable oil, animal fats, castor oil, cocoa butter, safflower oil, cottonseed oil, corn oil, olive oil, cod liver oil, almond oil, avocado oil, palm oil, sesame oil, squalene, and maleated soybean oil; acetoglycerides, such as acetylated monoglycerides; ethoxylated glycerides, such as ethoxylated glyceryl monostearate; alkyl esters of fatty acids such as methyl, isopropyl, and butyl, hexyllaurate, isohexyllaurate, isohexyl palmitate, isopropyl palmitate, decyl oleate, isodecyloleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate esters of fatty acid; alkenyl esters of fatty acids such as oleyl myristate, oleyl stearate, and oleyl oleate; fatty acids such as pelargonic, lauric, myristic, palmitic, stearic, isostearic, hydroxystearic, oleic, linoleic, ricinoleic, arachidic, behenic, and erucic acids; fatty alcohols such as lauryl, myristyl, cetyl, hexadecyl, stearyl isostearyl, hydroxystearyl, oleyl, ricinoleyl, behenyl, erucyl, and 2-octyl dodecanyl alcohols; fatty alcohol ethers such as lauryl, cetyl, stearyl, isostearyl, oleyl, and cholesterol alcohols, having attached thereto from 1 to 50 ethylene oxide groups or 1 to 50 propylene oxide groups; ether-esters such as fatty acid esters of ethoxylated fatty alcohols; lanolin and derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases; polyhydric alcohol esters such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid esters, sorbitan fatty acid esters, and polyoxyethylene sorbitan fatty acid esters are satisfactory polyhydric alcohol esters; waxes such as beeswax, spermaceti, myristyl myristate, stearyl stearatepolyoxyethylene sorbitol beeswax, carnauba and candelilla waxes; phospholipids such as lecithin and derivatives; sterols such as cholesterol and cholesterol fatty acid esters, amides such as fatty acid amides, ethoxylated fatty acid amides, and solid fatty acid alkanolamides.

In addition, the nicotinamide riboside esters and carbonates active agents and pharmaceutically acceptable carrier may be enclosed in a hard or soft shell gelatin capsule, compressed into tablets, or incorporated directly into the individual's diet. Specifically, the pharmaceutically active agent may be incorporated with excipients and used in the form of ingestible tablets, buccal tablets, troches, capsules, elixirs, suspensions, syrups, wafers, and the like. When the pharmaceutically active agent is administered orally, it may be mixed with other food forms and pharmaceutically acceptable flavor enhancers. When the pharmaceutically active agent is administered enterally, they may be introduced in a solid, semi-solid, suspension, or emulsion form and may be compounded with any number of well-known, pharmaceutically acceptable additives. Sustained release oral delivery systems and/or enteric coatings for orally administered dosage forms are known in the art and also contemplated. Transdermal delivery refers to the diffusion of an agent across the barrier of the skin. The skin (stratum corneum and epidermis) acts as a barrier and few pharmaceutical agents are able to penetrate intact skin. In contrast, the dermis is permeable to many solutes and absorption of drugs therefor occurs more readily through skin which is abraded or otherwise stripped of the epidermis to expose the dermis. Absorption through intact skin can be enhanced by placing the active agent in an oily vehicle before application to the skin (a process known as inunction). Passive topical administration may consist of applying the active agent directly to the treatment site in combination with emollients or penetration enhancers.

Conditions of the eye can be treated or prevented by, e.g., systemic, topical, intraocular injection of a compound, or by insertion of a sustained release device that releases a compound. A compound may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

The compounds described herein may be stored in oxygen free environment. For example, a composition can be prepared in an airtight capsule for oral administration, such as Capsugel from Pfizer, Inc. The pharmaceutical or cosmetic composition may further provide an oxygen-free environment, e.g., as with an hermetically-sealed composition or an air-tight capsule.

Cells, e.g., treated ex vivo with a compound as described herein, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of compounds can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity.

The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

4. Exemplary Uses

In certain aspects, the invention provides methods of treating or preventing a disease or disorder that would benefit from increased NAD levels, for example by increasing in vivo levels of NAD (e.g. intracellular NAD levels, levels of NAD in tissues or plasma, and/or overall NAD levels in an organism). Without wishing to be limited to a single mechanism, increased NAD levels serve to modulated the level and/or activity of one or more sirtuin proteins, e.g. by activating SIRT1 and or SIRT3.

Without limiting the invention to a particular mode of action, in certain embodiments, the invention provides methods for using the nicotinamide riboside ester and carbonate preparations and pharmaceutical or cosmetic compositions of the invention to elevate NAD levels and activate a sirtuin protein, e.g., increase activity of a sirtuin protein. Increased sirtuin protein activity and/or increased sirtuin levels may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc.

The methods comprise administering to a subject in need thereof a pharmaceutically effective amount of a nicotinamide riboside chloride salt preparation or pharmaceutical preparation.

In certain embodiments, the nicotinamide riboside ester and carbonate preparations and pharmaceutical or cosmetic compositions described herein may be taken alone or in combination with other agents. In one embodiment, the nicotinamide riboside ester and carbonate preparations and pharmaceutical or cosmetic compositions may be administered to a subject in need thereof in conjunction with a sirtuin-modulating compound (e.g., an allosteric SIRT1 activators described in, e.g. WO 2007/019346, WO 2007/019344, WO 2008/156866, WO2008/156869, WO2010/071853, WO2009/134973, WO2010/003048, WO2010/037127, WO2010/037129, WO2013/059587, WO2013/059589, WO2013/059594, and WO 2011/059839). In another embodiment, the nicotinamide riboside ester and carbonate preparations and pharmaceutical or cosmetic composition may be administered with one or more of the following compounds: resveratrol, butein, fisetin, piceatannol, or quercetin. In an exemplary embodiment, the nicotinamide riboside ester and carbonate preparations and pharmaceutical or cosmetic composition may be administered in combination with nicotinic acid (i.e., niacin).

In another embodiment, the nicotinamide riboside ester and carbonate preparations or pharmaceutical or cosmetic composition of the invention may be administered with one or more of the following compounds that decrease the level and/or activity of a sirtuin protein:nicotinamide (NAM), suramin; EX527 (6-Chloro-2,3,4,9-tetrahydro-1H-carbazole-1-carboxamide); NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin gallate (Hydroxy sites 5,7,3',4',5' and gallate ester on 3); cyanidin chloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; gossypetin (3,5,7,8,3',4'-hexahydroxyflavone), sirtinol; and splitomicin (see e.g., Howitz et al. (2003) Nature 425:191; Grozinger et al. (2001) J. Biol. Chem. 276:38837; Dedalov et al. (2001) PNAS 98:15113; and Hirao et al. (2003) J. Biol. Chem 278:52773). In yet another embodiment, the nicotinamide riboside ester and carbonate preparations or pharmaceutical or cosmetic composition of the invention may be administered with one or more therapeutic agents for the treatment or prevention of various diseases, including, for example, cancer, diabetes, neurodegenerative diseases, cardiovascular disease, blood clotting, inflammation, flushing, obesity, ageing, stress, etc. In various embodiments, combination therapies comprising the nicotinamide riboside ester and carbonate preparations or pharmaceutical or cosmetic composition of the invention may refer to (1) pharmaceutical or cosmetic compositions that comprise one or more of the nicotinamide riboside ester and carbonate preparations or pharmaceutical or cosmetic composition of the invention in combination with one or more therapeutic agents; and (2) co-administration of one or more of the nicotinamide riboside ester and carbonate preparations or pharmaceutical or cosmetic composition of the invention with one or more therapeutic agents wherein the nicotinamide riboside ester and carbonate preparations or pharmaceutical or cosmetic composition and the therapeutic agent have not been formulated in the same compositions. When using separate formulations, the of the nicotinamide riboside ester and carbonate preparations or pharmaceutical or cosmetic composition of the invention may be administered at the same, intermittent, staggered, prior to, subsequent to, or combinations thereof, with the administration of another therapeutic agent.

In certain embodiments, methods for reducing, preventing or treating diseases or disorders using of the nicotinamide riboside ester and carbonate preparations or pharmaceutical or cosmetic composition of the invention may also comprise increasing the protein level of a sirtuin, such as human SIRT1 or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370. The nucleic acid may be under the control of a promoter that regulates the expression of the SIRT1 nucleic acid. Alternatively, the nucleic acid may be introduced into the cell at a location in the genome that is downstream of a promoter. Methods for increasing the level of a protein using these methods are well known in the art.

A nucleic acid that is introduced into a cell to increase the protein level of a sirtuin may encode a protein that is at least about 80%, 85%, 90%, 95%, 98%, or 99% identical to the sequence of a sirtuin, e.g., GenBank Accession No. NP_036370. For example, the nucleic acid encoding the protein may be at least about 80%, 85%, 90%, 95%, 98%, or 99% identical to GenBank Accession No. NM_012238. The nucleic acid may also be a nucleic acid that hybridizes, preferably under stringent hybridization conditions, to a nucleic acid encoding a wild-type sirtuin, e.g., GenBank Accession No. NM_012238. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM 012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods for reducing, preventing or treating diseases or disorders using the nicotinamide riboside ester and carbonate preparations or pharmaceutical or cosmetic composition of the invention may also comprise decreasing the protein level of a sirtuin, such as human SIRT1 or homologs thereof. Decreasing a sirtuin protein level can be achieved according to methods known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods for modulating sirtuin protein levels also include methods for modulating the transcription of genes encoding sirtuins, methods for stabilizing/destabilizing the corresponding mRNAs, and other methods known in the art.

Aging/Stress

In one aspect of the invention, the disease or disorder that would benefit from increased NAD levels relates to aging and/or stress. Accordingly, in one embodiment the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with the nicotinamide riboside ester and carbonate preparations and pharmaceutical or cosmetic compositions of the invention.

For example, the methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a nicotinamide riboside ester or carbonate preparation to keep the cells, or progeny thereof, in culture for longer periods of time. Such cells can also be used for transplantation into a subject, e.g., after ex vivo modification.

In one embodiment, cells that are intended to be preserved for long periods of time may be treated with the nicotinamide riboside ester and carbonate preparations and pharmaceutical or cosmetic compositions of the invention that increases the in vivo levels of NAD (i.e., intracellular NAD levels). The cells may be in suspension (e.g., blood cells, serum, biological growth media, etc.) or in tissues or organs. For example, blood collected from an individual for purposes of transfusion may be treated with a nicotinamide riboside ester or carbonate preparation to preserve the blood cells for longer periods of time. Additionally, blood to be used for forensic purposes may also be preserved using the nicotinamide riboside ester and carbonate preparations and pharmaceutical or cosmetic compositions of the invention. Other cells that may be treated to extend their lifespan or protect against apoptosis include cells for consumption, e.g., cells from non-human mammals (such as meat) or plant cells (such as vegetables).

The nicotinamide riboside ester and carbonate preparations and pharmaceutical or cosmetic compositions of the invention that increase the level of NAD, and/or the activity of a sirtuin protein may also be applied during developmental and growth phases in mammals, plants, insects or microorganisms, in order to, e.g., alter, retard or accelerate the developmental and/or growth process.

In another embodiment, the nicotinamide riboside ester and carbonate preparations and pharmaceutical or cosmetic compositions of the invention that increase the level of NAD and/or the activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft.

The cells or tissue may be treated with the using the nicotinamide riboside ester and carbonate preparations and pharmaceutical or cosmetic compositions of the invention prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with the nicotinamide riboside ester and carbonate preparations or pharmaceutical or cosmetic compositions of the invention, or may have a subset of cells/tissue treated locally with the nicotinamide riboside ester and carbonate preparations and pharmaceutical or cosmetic compositions of the invention that increase the level of NAD and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with the nicotinamide riboside ester and carbonate preparations and pharmaceutical or cosmetic compositions of the invention that increases the level of NAD and/or the activity of a sirtuin protein in vivo, e.g., to increase their lifespan or prevent apoptosis. For example, skin can be protected from aging (e.g., developing wrinkles, loss of elasticity, etc.) by treating skin or epithelial cells with the nicotinamide riboside ester and carbonate preparations and pharmaceutical or cosmetic compositions of the invention that increases the level of NAD and/or the activity of a sirtuin protein. In an exemplary embodiment, skin is contacted with a pharmaceutical or cosmetic composition comprising a nicotinamide riboside ester and carbonate preparation or pharmaceutical or cosmetic composition of the invention that increases the level of NAD and/or activity of a sirtuin protein. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, the nicotinamide riboside ester and carbonate preparations and pharmaceutical or cosmetic compositions of the invention that increase the level of NAD and/or activity of a sirtuin protein may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

The nicotinamide riboside ester and carbonate preparations and pharmaceutical or cosmetic compositions of the invention may be delivered locally or systemically to a subject. In one embodiment, the nicotinamide riboside ester and carbonate preparations and pharmaceutical or cosmetic compositions of the invention is delivered locally to a tissue or organ of a subject by injection, topical formulation, et cetera.

In another embodiment, a nicotinamide riboside ester and carbonate preparation or pharmaceutical or cosmetic compositions of the invention that increases the level of NAD and/or the activity of a sirtuin protein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, the nicotinamide riboside ester and carbonate preparations and pharmaceutical or cosmetic compositions of the invention that increase the level of NAD and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

The nicotinamide riboside ester and carbonate preparations and pharmaceutical or cosmetic compositions of the invention that increase the level of NAD and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

The nicotinamide riboside ester and carbonate preparations and pharmaceutical or cosmetic compositions of the invention that increase the level of NAD and/or activity of a sirtuin protein can also be administered to a subject suffering from an acute disease, e.g., damage to an organ or tissue, e.g., a subject suffering from stroke or myocardial infarction or a subject suffering from a spinal cord injury. The nicotinamide riboside ester and carbonate preparations and pharmaceutical or cosmetic compositions of the invention that increase the level of NAD and/or activity of a sirtuin protein may also be used to repair an alcoholic's liver.

Mitochondrial Disease

In preferred embodiments, the invention provides methods for treating and/or preventing a mitochondrial disease or disorder by administering to a subject in need thereof a nicotinamide riboside ester and carbonate preparations or pharmaceutical or cosmetic compositions of the invention that increases the level of NAD. Suitable mitochondrial diseases or disorders include Leber's hereditary optic neuropathy (LHON), mitochondrial encephalomyopathy lactic acidosis and stroke-like episodes (MELAS), myoclonic epilepsy and ragged-red fiber disease (MERRF), and Leigh syndrome (LS), Charcot-Marie-Tooth disease, Type 2A2, Barth Syndrome, fatty acid oxidation disorders, inherited forms of deafness and blindness, metabolic abnormalities induced by toxic chemicals and/or drugs (e.g., cisplatin induced deafness, gentamycin induced deafness), and as otherwise described herein.

Mitochondrial disease includes multiple disorders caused by dysfunctional mitochondria, the organelles that generate energy for the cell. Mitochondria are found in every cell of the human body except red blood cells and convert the energy of food molecules into the ATP that powers most cell functions. Mitochondrial diseases are sometimes (about 15% of the time) caused by mutations in the mitochondrial DNA that affect mitochondrial function. Other causes of mitochondrial disease are mutations in genes of the nuclear DNA, whose gene products are imported into the mitochondria (mitochondrial proteins) as well as acquired mitochondrial conditions. Mitochondrial diseases take on unique characteristics both because of the way the diseases are often inherited and because mitochondria are so critical to cell function. The subclass of these diseases that have neuromuscular disease symptoms are often called a mitochondrial myopathy.

In addition to the mitochondrial myopathies, other examples include: Diabetes mellitus and deafness (DAD) because this combination at an early age can be due to mitochondrial disease and diabetes mellitus and deafness can also be found together for other reasons; Leber's hereditary optic neuropathy (LHON) is characterized by loss of vision beginning in young adulthood and is an eye disorder characterized by progressive loss of central vision due to degeneration of the optic nerves and retina; Wolff-Parkinson-White syndrome is a multiple sclerosis-type disease that affects 1 in 50,000 people in Finland; Leigh syndrome, a subacute sclerosing encephalopathy which usually begins late in the first year of life (although onset may occur in adulthood) and is characterized by a rapid decline in function that is marked by seizures, altered states of consciousness, dementia, ventilatory failure; Neuropathy, ataxia, retinitis pigmentosa, and ptosis (NARP) is characterized by progressive symptoms as described in the acronym and eventually may result in dementia; Myoneurogenic gastrointestinal encephalopathy (MNGIE) is characterized by gastrointestinal pseudo-obstruction and neuropathy; Myoclonic Epilepsy with Ragged Red Fibers (MERRF) is characterized by progressive myoclonic epilepsy and "Ragged Red Fibers" which are clumps of diseased mitochondria that accumulate in the subsarcolemmal region of the muscle fiber and appear as "Ragged Red Fibers" when muscle is stained with modified Gomori trichrome stain, as well as short stature, hearing loss, lactic acidosis, and exercise intolerance; Mitochondrial myopathy, encephalomyopathy, lactic acidosis, stroke-like symptoms (MELAS); and mtDNA depletion. Other mitochondrial conditions include Friedreich's ataxia, which can affect the mitochondria, but are not associated with mitochondrial proteins.

In general, symptoms of mitochondrial disease include poor growth, loss of muscle coordination, muscle weakness, visual problems, hearing problems, learning disabilities, heart disease, liver disease, kidney disease, gastrointestinal disorders, respiratory disorders, neurological problems, autonomic dysfunction and dementia. However, the effects of mitochondrial disease can be quite varied. Since the distribution of the defective mitochondrial DNA may vary from organ to organ within the body, and each mutation is modulated by other genome variants, the mutation that in one individual may cause liver disease might in another person cause a brain disorder. The severity of the specific defect may also be great or small. Some minor defects cause only "exercise intolerance", with no serious illness or disability. Defects often affect the operation of the mitochondria and multiple tissues more severely, leading to multisystem diseases. Mitochondrial diseases as a rule are worse when the defective mitochondria are present in the muscles, cerebrum, or nerves, because these cells use more energy than most other cells in the body.

Although mitochondrial diseases vary greatly in presentation from person to person, several major clinical categories of these conditions have been defined, based on the most common phenotypic features, symptoms, and signs associated with the particular mutations that tend to cause them. An outstanding question and area of research is whether ATP depletion or reactive oxygen species are in fact responsible for the observed phenotypic consequences.

In examining the energetic of mitochondrial disorders, the effective overall energy unit for the available body energy is referred to as the daily glycogen generation capacity, and is used to compare the mitochondrial output of healthy individuals to that of afflicted or chronically glycogen-depleted individuals. This value is slow to change in a given individual, as it takes between 18 and 24 months to complete a full cycle. Further, the glycogen generation capacity is entirely dependent on, and determined by, the operating levels of the mitochondria in all of the cells of the human body, however, the relation between the energy generated by the mitochondria and the glycogen capacity is very loose and is mediated by many biochemical pathways.

Mitochondrial disorders may be caused by mutations, acquired or inherited, in mitochondrial DNA (mtDNA) or in nuclear genes that code for mitochondrial components. They may also be the result of acquired mitochondrial dysfunction due to adverse effects of drugs, infections, or other environmental causes (see MeSH). Nuclear DNA has two copies per cell (except for sperm and egg cells), one copy being inherited from the father and the other from the mother. Mitochondrial DNA, however, is strictly inherited from the mother and each mitochondrial organelle typically contains multiple mtDNA copies. During cell division the mitochondrial DNA copies segregate randomly between the two new mitochondria, and then those new mitochondria make more copies. If only a few of the mtDNA copies inherited from the mother are defective, mitochondrial division may cause most of the defective copies to end up in just one of the new mitochondria. Mitochondrial disease may become clinically apparent once the number of affected mitochondria reaches a certain level; this phenomenon is called "threshold expression".

Mitochondrial DNA mutations occur frequently, due to the lack of the error checking capability that nuclear DNA has. This means that mitochondrial DNA disorders may occur spontaneously and relatively often. Defects in enzymes that control mitochondrial DNA replication (all of which are encoded for by genes in the nuclear DNA) may also cause mitochondrial DNA mutations.

Most mitochondrial function and biogenesis is controlled by nuclear DNA. Human mitochondrial DNA encodes only 13 proteins of the respiratory chain, while most of the estimated 1,500 proteins and components targeted to mitochondria are nuclear-encoded.

Defects in nuclear-encoded mitochondrial genes are associated with hundreds of clinical disease phenotypes including anemia, dementia, hypertension, lymphoma, retinopathy, seizures, and neurodevelopmental disorders.

There are few treatments for mitochondrial disease and disorders, however the invention includes the combination of existing methods of treatments with the compounds, pharmaceutical compositions and methods of treatment of the instant invention. For example, vitamins are frequently prescribed, though the evidence for their effectiveness is limited (see Marriage B, Clandinin M T, Glerum D M (2003) "Nutritional cofactor treatment in mitochondrial disorders" *J Am Diet Assoc* 103 (8): 1029-38). Membrane penetrating antioxidants have the most important role in improving mitochondrial dysfunction. Pyruvate has been proposed as a treatment option (Tanaka M, Nishigaki Y, Fuku N, Ibi T, Sahashi K, Koga Y (2007) "Therapeutic potential of pyruvate therapy for mitochondrial diseases" *Mitochondrion* 7 (6): 399-401). Spindle transfer, where the nuclear DNA is transferred to another healthy egg cell leaving the defective mitochondrial DNA behind, is a potential treatment procedure that has been successfully carried out on monkeys (Tachibana M, Sparman M, Sritanaudomchai H, Ma H, Clepper L, Woodward J, Li Y, Ramsey C, Kolotushkina O, Mitalipov S (September 2009) "Mitochondrial gene replacement in primate offspring and embryonic stem cells" *Nature* 461 (7262): 367-372). Using a similar pronuclear transfer technique, researchers at Newcastle University successfully transplanted healthy DNA in human eggs from women with mitochondrial disease into the eggs of women donors who were unaffected (Craven L, Tuppen H A, Greggains G D, Harbottle S J, Murphy J L, Cree L M, Murdoch A P, Chinnery P F, Taylor R W, Lightowlers R N, Herbert M, Turnbull D M (May 2010). "Pronuclear transfer in human embryos to prevent transmission of mitochondrial DNA disease" *Nature* 465 (7294): 82-85). Embryonic mitochondrial transplant and protofection have been proposed as a possible treatment for inherited mitochondrial disease, and allotopic expression of mitochondrial proteins as a radical treatment for mtDNA mutation load.

About 1 in 4,000 children in the United States will develop mitochondrial disease by the age of 10 years. Up to 4,000 children per year in the US are born with a type of mitochondrial disease. Because mitochondrial disorders contain many variations and subsets, some particular mitochondrial disorders are very rare. Many diseases of aging are caused by defects in mitochondrial function. Since the mitochondria are responsible for processing oxygen and converting substances from the foods we eat into energy for essential cellular functions, if there are problems with the mitochondria, it can lead to many defects for adults.

These include Type 2 diabetes, Parkinson's disease, atherosclerotic heart disease, stroke, Alzheimer's disease, and cancer. Many medicines can also injure the mitochondria.

Furthermore, the role of mitochondria in insulin resistance among the offspring of patients with type 2 diabetes has been examined (Petersen et al. (2004) "Impaired Mitochondrial Activity in the Insulin-Resistant Offspring of Patients with Type 2 Diabetes" New England Journal of Medicine).

"Mitochondrial disease" refers to any disorders in which deficits in mitochondrial respiratory chain activity contribute in the development of pathophysiology of such disorders in a mammal. This category includes 1) congenital genetic deficiencies in activity of one or more components of the mitochondrial respiratory chain; 2) acquired deficiencies in the activity of one or more components of the mitochondrial respiratory chain, wherein such deficiencies are caused by, inter alia, a) oxidative damage during aging; b) elevated intracellular calcium; c) exposure of affected cells to nitric oxide; d) hypoxia or ischemia; e) microtubule-associated deficits in axonal transport of mitochondria, or f) expression of mitochondrial uncoupling proteins.

The mitochondrial respiratory chain (also known as the electron transport chain) comprises 5 major complexes: Complex I NADH:ubiquinone reductase; Complex II Succinate:ubiquinone reductase; Complex III ubiquinol:cytochrome-c reductase; Complex IV cytochrome-c oxidase; and Complex V ATP synthase. Complexes I and II accomplish the transfer of electrons from metabolic fuels like glycolysis products and fatty acids to ubiquinone (Coenzyme Q), converting it to ubiquinol. Ubiquinol is converted back to ubiquinone by transfer of electrons to cytochrome c in Complex III. Cytochrome c is reoxidized at Complex IV by transfer of electrons to molecular oxygen,—producing water. Complex V utilizes potential energy from the proton gradient produced across the mitochondrial membrane by these electron transfers, converting ADP into ATP, which then provides energy to metabolic reactions in the cell.

Cardiovascular Disease

In another embodiment, the invention provides a method for treating and/or preventing a cardiovascular disease by administering to a subject in need thereof a nicotinamide riboside ester and carbonate preparations or pharmaceutical compositions of the invention that increases the level of NAD and/or the activity of a sirtuin protein.

Cardiovascular diseases that can be treated or prevented using the nicotinamide riboside ester and carbonate preparations and pharmaceutical compositions of the invention that increase the level of NAD and/or the activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The nicotinamide riboside ester and carbonate preparations and pharmaceutical compositions of the invention that increase the level of NAD and/or activity of a sirtuin protein may also be used for increasing HDL levels in plasma of an individual.

Yet other disorders that may be treated with sirtuin-modulating compounds that increase the level of NAD and/or the activity of a sirtuin protein include restenosis, e.g., following coronary intervention, and disorders relating to an abnormal level of high density and low density cholesterol.

In one embodiment, a nicotinamide riboside ester and carbonate preparation or pharmaceutical composition of the invention that increases the level of NAD and/or the activity of a sirtuin protein may be administered as part of a combination therapeutic with another cardiovascular agent including, for example, an anti-arrhythmic agent, an anti-hypertensive agent, a calcium channel blocker, a cardioplegic solution, a cardiotonic agent, a fibrinolytic agent, a sclerosing solution, a vasoconstrictor agent, a vasodilator agent, a nitric oxide donor, a potassium channel blocker, a sodium channel blocker, statins, or a naturiuretic agent.

In one embodiment, a nicotinamide riboside ester and carbonate preparations or pharmaceutical composition of the invention that increases the level and/or activity of NAD and/or the activity of a sirtuin protein may be administered as part of a combination therapeutic with an anti-arrhythmia agent. Anti-arrhythmia agents are often organized into four main groups according to their mechanism of action: type I, sodium channel blockade; type II, beta-adrenergic blockade; type III, repolarization prolongation; and type IV, calcium channel blockade. Type I anti-arrhythmic agents include lidocaine, moricizine, mexiletine, tocainide, procainamide, encainide, flecanide, tocainide, phenytoin, propafenone, quinidine, disopyramide, and flecainide. Type II anti-arrhythmic agents include propranolol and esmolol. Type III includes agents that act by prolonging the duration of the action potential, such as amiodarone, artilide, bretylium, clofilium, isobutilide, sotalol, azimilide, dofetilide, dronedarone, ersentilide, ibutilide, tedisamil, and trecetilide. Type IV anti-arrhythmic agents include verapamil, diltaizem, digitalis, adenosine, nickel chloride, and magnesium ions.

In another embodiment, a nicotinamide riboside ester or carbonate preparation or pharmaceutical composition of the invention that increases the level of NAD and/or the activity of a sirtuin protein may be administered as part of a combination therapeutic with another cardiovascular agent. Examples of cardiovascular agents include vasodilators, for example, hydralazine; angiotensin converting enzyme inhibitors, for example, captopril; antianginal agents, for example, isosorbide nitrate, glyceryl trinitrate and pentaerythritol tetranitrate; anti-arrhythmic agents, for example, quinidine, procainaltide and lignocaine; cardioglycosides, for example, digoxin and digitoxin; calcium antagonists, for example, verapamil and nifedipine; diuretics, such as thiazides and related compounds, for example, bendrofluazide, chlorothiazide, chlorothalidone, hydrochlorothiazide and other diuretics, for example, fursemide and triamterene, and sedatives, for example, nitrazepam, flurazepam and diazepam.

Other exemplary cardiovascular agents include, for example, a cyclooxygenase inhibitor such as aspirin or indomethacin, a platelet aggregation inhibitor such as clopidogrel, ticlopidene or aspirin, fibrinogen antagonists or a diuretic such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, angiotensin II antagonists such as losartan, irbesartan or valsartan, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or animal salivary gland plasminogen activators, calcium channel blocking agents such as verapamil, nifedipine or diltiazem, thromboxane receptor antagonists such as ifetroban, prostacyclin mimetics, or phosphodiesterase inhibitors. Such combination products if formulated as a fixed dose employ the compounds of this invention within the dose range described above and the other pharmaceutically active agent within its approved dose range.

Yet other exemplary cardiovascular agents include, for example, vasodilators, e.g., bencyclane, cinnarizine, citicoline, cyclandelate, cyclonicate, ebumamonine, phenoxezyl, flunarizine, ibudilast, ifenprodil, lomerizine, naphlole, nikamate, nosergoline, nimodipine, papaverine, pentifylline, nofedoline, vincamin, vinpocetine, vichizyl, pentoxifylline, prostacyclin derivatives (such as prostaglandin E1 and prostaglandin I2), an endothelin receptor blocking drug (such as bosentan), diltiazem, nicorandil, and nitroglycerin. Examples of the cerebral protecting drug include radical scavengers (such as edaravone, vitamin E, and vitamin C), glutamate antagonists, AMPA antagonists, kainate antagonists, NMDA antagonists, GABA agonists, growth factors, opioid antagonists, phosphatidylcholine precursors, serotonin agonists, Na+/Ca2+ channel inhibitory drugs, and K+ channel opening drugs. Examples of the brain metabolic stimulants include amantadine, tiapride, and gamma-aminobutyric acid. Examples of the anticoagulant include heparins (such as heparin sodium, heparin potassium, dalteparin sodium, dalteparin calcium, heparin calcium, parnaparin sodium, reviparin sodium, and danaparoid sodium), warfarin, enoxaparin, argatroban, batroxobin, and sodium citrate. Examples of the antiplatelet drug include ticlopidine hydrochloride, dipyridamole, cilostazol, ethyl icosapentate, sarpogrelate hydrochloride, dilazep hydrochloride, trapidil, a nonsteroidal antiinflammatory agent (such as aspirin), beraprostsodium, iloprost, and indobufene. Examples of the thrombolytic drug include urokinase, tissue-type plasminogen activators (such as alteplase, tisokinase, nateplase, pamiteplase, monteplase, and rateplase), and nasaruplase. Examples of the antihypertensive drug include angiotensin converting enzyme inhibitors (such as captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, and randolapril), angiotensin II antagonists (such as losartan, candesartan, valsartan, eprosartan, and irbesartan), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline), beta-adrenaline receptor blocking drugs (propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, xybenolol, and esmolol), alpha-receptor blocking drugs (such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine), sympathetic nerve inhibitors (such as clonidine, guanfacine, guanabenz, methyldopa, and reserpine), hydralazine, todralazine, budralazine, and cadralazine. Examples of the antianginal drug include nitrate drugs (such as amyl nitrite, nitroglycerin, and isosorbide), beta-adrenaline receptor blocking drugs (such as propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, andxybenolol), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendiline, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline) trimetazidine, dipyridamole, etafenone, dilazep, trapidil, nicorandil, enoxaparin, and aspirin. Examples of the diuretic include thiazide diuretics (such as hydrochlorothiazide, methyclothiazide, trichlormethiazide, benzylhydrochlorothiazide, and penflutizide), loop diuretics (such as furosemide, etacrynic acid, bumetanide, piretanide, azosemide, and torasemide), K+ sparing diuretics (spironolactone, triamterene, andpotassiumcanrenoate), osmotic diuretics (such as isosorbide, D-mannitol, and glycerin), nonthiazide diuretics (such as meticrane, tripamide, chlorthalidone, and mefruside), and acetazolamide. Examples of the cardiotonic include xdigitalis formulations (such as digitoxin, digoxin, methyldigoxin, deslanoside, vesnarinone, lanatoside C, and proscillaridin), xanthine formulations (such as aminophylline, choline theophylline, diprophylline, and proxyphylline), catecholamine formulations (such as dopamine, dobutamine, and docarpamine), PDE III inhibitors (such as amrinone, olprinone, and milrinone), denopamine, ubidecarenone, pimobendan, levosimendan, aminoethylsulfonic acid, vesnarinone, carperitide, and colforsin daropate. Examples of the antiarrhythmic drug include ajmaline, pirmenol, procainamide, cibenzoline, disopyramide, quinidine, aprindine, mexiletine, lidocaine, phenyloin, pilsicainide, propafenone, flecainide, atenolol, acebutolol, sotalol, propranolol, metoprolol, pindolol, amiodarone, nifekalant, diltiazem, bepridil, and verapamil. Examples of the antihyperlipidemic drug include atorvastatin, simvastatin, pravastatin sodium, fluvastatin sodium, clinofibrate, clofibrate, simfibrate, fenofibrate, bezafibrate, colestimide, and colestyramine. Examples of the immunosuppressant include azathioprine, mizoribine, cyclosporine, tacrolimus, gusperimus, and methotrexate.

Cell Death/Cancer

The nicotinamide riboside ester and carbonate preparations and pharmaceutical or cosmetic compositions of the invention that increase the level of NAD and/or activity of a sirtuin protein may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In another embodiment, the radiation or toxin exposure is received unintentionally, e.g., as a result of an industrial accident, habitation in a location of natural radiation, terrorist act, or act of war involving radioactive or toxic material. In such a case, the nicotinamide riboside ester and carbonate preparation or pharmaceutical or cosmetic composition of the invention is preferably administered as soon as possible after the exposure to inhibit apoptosis and the subsequent development of acute radiation syndrome.

The nicotinamide riboside ester and carbonate preparations and pharmaceutical or cosmetic compositions of the invention may also be used for treating and/or preventing cancer. In certain embodiments, the nicotinamide riboside ester and carbonate preparations and pharmaceutical or cosmetic compositions of the invention that increase the level of NAD and/or activity of a sirtuin protein may be used for treating and/or preventing cancer. Calorie restriction has been linked to a reduction in the incidence of age-related disorders including cancer (see e.g., Bordone and Guarente, Nat. Rev. Mol. Cell Biol. (2005 epub); Guarente and Picard, Cell 120: 473-82 (2005); Berrigan, et al., Carcinogenesis 23: 817-822 (2002); and Heilbronn and Ravussin, Am. J. Clin. Nutr. 78: 361-369 (2003)). Additionally, the Sir2 protein from yeast has been shown to be required for lifespan extension by glucose restriction (see e.g., Lin et al., Science 289: 2126-2128 (2000); Anderson et al., Nature 423: 181-185 (2003)), a yeast model for calorie restriction. Accordingly, an increase in the level of NAD and/or activity of a sirtuin protein may be useful for treating and/or preventing the incidence of age-related disorders, such as, for example, cancer.

In other embodiments, the nicotinamide riboside ester and carbonate preparations and pharmaceutical or cosmetic compositions of the invention may be used in conjunction with sirtuin-modulating compounds that decrease the level and/or activity of a sirtuin protein for the purpose of treating or preventing cancer. For example, inhibitory compounds may be used to stimulate acetylation of substrates such as p53 and thereby increase apoptosis, as well as to reduce the lifespan of cells and organisms, render them more sensitive to stress, and/or increase the radiosensitivity and/or chemosensitivity of a cell or organism. Thus, inhibitory compounds may be used, e.g., for treating cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth can also be treated, e.g., warts. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of nicotinamide riboside ester or carbonate preparations. Alternatively, cells can be obtained from a subject, treated ex vivo to remove certain undesirable cells, e.g., cancer cells, and administered back to the same or a different subject.

Furthermore, chemotherapeutic agents may be coadministered with the nicotinamide riboside ester and carbonate preparations and pharmaceutical or cosmetic compositions.

Chemotherapeutic agents described herein as having anticancer activity (e.g., compounds that induce apoptosis, compounds that reduce lifespan or compounds that render cells sensitive to stress) include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; chromatin disruptors.

These chemotherapeutic agents may be used by themselves with a sirtuin-modulating compound described herein as inducing cell death or reducing lifespan or increasing sensitivity to stress and/or in combination with other chemotherapeutics agents. Many combinatorial therapies have been developed, including but not limited to those listed in Table 1.

TABLE 1

Exemplary combinatorial therapies for the treatment of cancer.

| Name | Therapeutic agents |
| --- | --- |
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |

TABLE 1-continued

Exemplary combinatorial therapies for the treatment of cancer.

| Name | Therapeutic agents |
|---|---|
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/ Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |

TABLE 1-continued

Exemplary combinatorial therapies for the treatment of cancer.

| Name | Therapeutic agents |
|---|---|
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposide, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |

TABLE 1-continued

Exemplary combinatorial therapies for the treatment of cancer.

| Name | Therapeutic agents |
|---|---|
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In addition to conventional chemotherapeutics, the nicotinamide riboside ester and carbonate preparations and pharmaceutical or cosmetic compositions described herein as capable of inducing cell death or reducing lifespan can also be used with antisense RNA, RNAi or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

Combination therapies comprising the nicotinamide riboside ester and carbonate preparations and pharmaceutical or cosmetic compositions of the invention and a conventional chemotherapeutic agent may be advantageous over combination therapies known in the art because the combination allows the conventional chemotherapeutic agent to exert greater effect at lower dosage. In a preferred embodiment, the effective dose (ED50) for a chemotherapeutic agent, or combination of conventional chemotherapeutic agents, when used in combination with a sirtuin-modulating compound is at least 2 fold less than the ED50 for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with the nicotinamide riboside ester and carbonate preparations and pharmaceutical or cosmetic compositions of the invention can be at least 2 fold greater than the TI for conventional chemotherapeutic regimen alone, and even more preferably at 5 fold, 10 fold or even 25 fold greater.

Neuronal Diseases/Disorders

In certain aspects, the nicotinamide riboside ester and carbonate preparations and pharmaceutical compositions of the invention that increase the level of NAD and/or the activity of a sirtuin protein can be used to treat patients suffering from neurodegenerative diseases, and traumatic or mechanical injury to the central nervous system (CNS) or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases evolve gradually, after a long period of normal brain function, due to progressive degeneration (e.g., nerve cell dysfunction and death) of specific brain regions. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Nicotinamide riboside ester and carbonate preparations and pharmaceutical compositions of the invention that increase the level of NAD and/or activity of a sirtuin protein can be used to treat these disorders and others as described below.

AD is a chronic, incurable, and unstoppable CNS disorder that occurs gradually, resulting in memory loss, unusual behavior, personality changes, and a decline in thinking abilities. These losses are related to the death of specific types of brain cells and the breakdown of connections between them. AD has been described as childhood development in reverse. In most people with AD, symptoms appear after the age 60. The earliest symptoms include loss of recent memory, faulty judgment, and changes in personality. Later in the disease, those with AD may forget how to do simple tasks like washing their hands. Eventually people with AD lose all reasoning abilities and become dependent on other people for their everyday care. Finally, the disease becomes so debilitating that patients are bedridden and typically develop coexisting illnesses.

PD is a chronic, incurable, and unstoppable CNS disorder that occurs gradually and results in uncontrolled body movements, rigidity, tremor, and gait difficulties. These motor system problems are related to the death of brain cells in an area of the brain that produces dopamine, a chemical that helps control muscle activity. In most people with PD, symptoms appear after age 50. The initial symptoms of PD are a pronounced tremor affecting the extremities, notably in the hands or lips. Subsequent characteristic symptoms of PD are stiffness or slowness of movement, a shuffling walk, stooped posture, and impaired balance. There are wide ranging secondary symptoms such as memory loss, dementia, depression, emotional changes, swallowing difficulties, abnormal speech, sexual dysfunction, and bladder and bowel problems. These symptoms will begin to interfere with routine activities, such as holding a fork or reading a newspaper. Finally, people with PD become so profoundly disabled that they are bedridden.

ALS (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed.

The causes of these neurological diseases have remained largely unknown. They are conventionally defined as distinct diseases, yet clearly show extraordinary similarities in basic processes and commonly demonstrate overlapping symptoms far greater than would be expected by chance alone. Current disease definitions fail to properly deal with the issue of overlap and a new classification of the neurodegenerative disorders has been called for.

Huntigton's Disease is another neurodegenerative disease resulting from genetically programmed degeneration of neurons in certain areas of the brain. This degeneration causes uncontrolled movements, loss of intellectual faculties, and emotional disturbance. HD is a familial disease, passed from parent to child through a dominant mutation in the wild-type gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing.

Tay-Sachs disease and Sandhoff disease are glycolipid storage diseases caused by the lack of lysosomal β-hexosaminidase (Gravel et al., in The Metabolic Basis of Inherited Disease, eds. Scriver et al., McGraw-Hill, New York, pp. 2839-2879, 1995). In both disorders, GM2 ganglioside and related glycolipids substrates for β-hexosaminidase accumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age. Neuronal loss through an apoptotic mechanism has been demonstrated (Huang et al., Hum. Mol. Genet. 6: 1879-1885, 1997).

It is well-known that apoptosis plays a role in AIDS pathogenesis in the immune system. However, HIV-1 also induces neurological disease. Shi et al. (J. Clin. Invest. 98: 1979-1990, 1996) examined apoptosis induced by HIV-1 infection of the CNS in an in vitro model and in brain tissue from AIDS patients, and found that HIV-1 infection of primary brain cultures induced apoptosis in neurons and astrocytes in vitro. Apoptosis of neurons and astrocytes was also detected in brain tissue from 10/11 AIDS patients, including 5/5 patients with HIV-1 dementia and 4/5 nondemented patients.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a nicotinamide riboside ester or carbonate preparation or pharmaceutical compositions of the invention that increases the level of NAD and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. The most common cause of distal axonopathy is diabetes, and the most common distal axonopathy is diabetic neuropathy. The most distal portions of axons are usually the first to degenerate, and axonal atrophy advances slowly towards the nerve's cell body. If the noxious stimulus is removed, regeneration is possible, though prognosis decreases depending on the duration and severity of the stimulus. Those with distal axonopathies usually present with symmetrical stocking-glove sensorimotor disturbances. Deep tendon reflexes and autonomic nervous system (ANS) functions are also lost or diminished in affected areas.

Diabetic neuropathies are neuropathic disorders that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy. Clinical manifestations of diabetic neuropathy include, for example, sensorimotor polyneuropathy such as numbness, sensory loss, dysesthesia and nighttime pain; autonomic neuropathy such as delayed gastric emptying or gastroparesis; and cranial neuropathy such as oculomotor (3rd) neuropathies or Mononeuropathies of the thoracic or lumbar spinal nerves.

Peripheral neuropathy is the medical term for damage to nerves of the peripheral nervous system, which may be caused either by diseases of the nerve or from the side-effects of systemic illness. Peripheral neuropathies vary in their presentation and origin, and may affect the nerve or the neuromuscular junction. Major causes of peripheral neuropathy include seizures, nutritional deficiencies, and HIV, though diabetes is the most likely cause. Mechanical pressure from staying in one position for too long, a tumor, intraneural hemorrhage, exposing the body to extreme conditions such as radiation, cold temperatures, or toxic substances can also cause peripheral neuropathy.

In an exemplary embodiment, a nicotinamide riboside ester and carbonate preparation or pharmaceutical compositions of the invention that increases the level of NAD and/or activity of a sirtuin protein may be used to treat or prevent multiple sclerosis (MS), including relapsing MS and monosymptomatic MS, and other demyelinating conditions, such as, for example, chromic inflammatory demyelinating polyneuropathy (CIDP), or symptoms associated therewith.

Multiple Sclerosis is a chronic, often disabling disease of the central nervous system. Various and converging lines of evidence point to the possibility that the disease is caused by a disturbance in the immune function, although the cause of this disturbance has not been established. This disturbance permits cells of the immune system to "attack" myelin, the fat containing insulating sheath that surrounds the nerve axons located in the central nervous system ("CNS"). When myelin is damaged, electrical pulses cannot travel quickly or normally along nerve fiber pathways in the brain and spinal cord. This results in disruption of normal electrical conductivity within the axons, fatigue and disturbances of vision, strength, coordination, balance, sensation, and bladder and bowel function.

As such, MS is now a common and well-known neurological disorder that is characterized by episodic patches of inflammation and demyelination which can occur anywhere in the CNS. However, almost always without any involvement of the peripheral nerves associated therewith. Demyelination produces a situation analogous to that resulting from cracks or tears in an insulator surrounding an electrical cord. That is, when the insulating sheath is disrupted, the circuit is "short circuited" and the electrical apparatus associated therewith will function intermittently or nor at all. Such loss of myelin surrounding nerve fibers results in short circuits in nerves traversing the brain and the spinal cord that thereby result in symptoms of MS. It is further found that such demyelination occurs in patches, as opposed to along the entire CNS. In addition, such demyelination may be intermittent. Therefore, such occurrences are disseminated in both time and space.

It is believed that the pathogenesis involves a local disruption of the blood brain barrier which causes a localized immune and inflammatory response, with consequent damage to myelin and hence to neurons.

Clinically, MS exists in both sexes and can occur at any age. However, its most common presentation is in the relatively young adult, often with a single focal lesion such as a damage of the optic nerve, an area of anesthesia (loss of sensation), or paraesthesia (localize loss of feeling), or muscular weakness. In addition, vertigo, double vision, localized pain, incontinence, and pain in the arms and legs may occur upon flexation of the neck, as well as a large variety of less common symptoms.

An initial attack of MS is often transient, and it may be weeks, months, or years before a further attack occurs. Some individuals may enjoy a stable, relatively event free condition for a great number of years, while other less fortunate ones may experience a continual downhill course ending in complete paralysis. There is, most commonly, a series of remission and relapses, in which each relapse leaves a patient somewhat worse than before.

Relapses may be triggered by stressful events, viral infections or toxins. Therein, elevated body temperature, i.e., a fever, will make the condition worse, or as a reduction of temperature by, for example, a cold bath, may make the condition better.

In yet another embodiment, a nicotinamide riboside ester or carbonate preparation or pharmaceutical composition of the invention that increases the level of NAD and/or activity of a sirtuin protein may be used to treat trauma to the nerves, including, trauma due to disease, injury (including surgical intervention), or environmental trauma (e.g., neurotoxins, alcoholism, etc.).

Nicotinamide riboside ester and carbonate preparations and pharmaceutical compositions of the invention that increase the level of NAD and/or activity of a sirtuin protein may also be useful to prevent, treat, and alleviate symptoms of various PNS disorders, such as the ones described below. The PNS is composed of the nerves that lead to or branch off from the CNS. The peripheral nerves handle a diverse array of functions in the body, including sensory, motor, and autonomic functions. When an individual has a peripheral neuropathy, nerves of the PNS have been damaged. Nerve damage can arise from a number of causes, such as disease, physical injury, poisoning, or malnutrition. These agents may affect either afferent or efferent nerves. Depending on the cause of damage, the nerve cell axon, its protective myelin sheath, or both may be injured or destroyed.

The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

Peripheral neuropathy is a widespread disorder, and there are many underlying causes. Some of these causes are common, such as diabetes, and others are extremely rare, such as acrylamide poisoning and certain inherited disorders. The most common worldwide cause of peripheral neuropathy is leprosy. Leprosy is caused by the bacterium *Mycobacterium leprae*, which attacks the peripheral nerves of affected people.

Leprosy is extremely rare in the United States, where diabetes is the most commonly known cause of peripheral neuropathy. It has been estimated that more than 17 million people in the United States and Europe have diabetes-related polyneuropathy. Many neuropathies are idiopathic; no known cause can be found. The most common of the inherited peripheral neuropathies in the United States is Charcot-Marie-Tooth disease, which affects approximately 125,000 persons.

Another of the better known peripheral neuropathies is Guillain-Barre syndrome, which arises from complications associated with viral illnesses, such as cytomegalovirus, Epstein-Barr virus, and human immunodeficiency virus (HIV), or bacterial infection, including *Campylobacter jejuni* and Lyme disease. The worldwide incidence rate is approximately 1.7 cases per 100,000 people annually. Other well-known causes of peripheral neuropathies include chronic alcoholism, infection of the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, or inherited neurologic disorders. Such diseases may affect the PNS and the CNS, as well as other body tissues.

Other PNS diseases treatable with sirtuin-modulating compounds that increase the level and/or activity of a sirtuin protein include: Brachial Plexus Neuropathies (diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al., Principles of Neurology, 6th ed, pp 1351-2); Diabetic Neuropathies (peripheral, autonomic, and cranial nerve disorders that are associated with diabetes mellitus). These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy (see Adams et al., Principles of Neurology, 6th ed, p1325); mononeuropathies (disease or trauma involving a single peripheral nerve in isolation, or out of proportion to evidence of diffuse peripheral nerve dysfunction). Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions; Neuralgia (intense or aching pain that occurs along the course or distribution of a peripheral or cranial nerve); Peripheral Nervous System Neoplasms (neoplasms which arise from peripheral nerve tissue). This includes neurofibromas; Schwannomas; granular cell tumors; and malignant peripheral nerve sheath tumors. See DeVita Jr et al., Cancer: Principles and Practice of Oncology, 5th ed, pp 1750-1); and Nerve Compression Syndromes (mechanical compression of nerves or nerve roots from internal or external causes). These may result in a conduction block to nerve impulses, due to, for example, myelin sheath dysfunction, or axonal loss. The nerve and nerve sheath injuries may be caused by ischemia; inflammation; or a direct mechanical effect; Neuritis (a general term indicating inflammation of a peripheral or cranial nerve). Clinical manifestation may include pain; paresthesias; paresis; or hyperthesia; Polyneuropathies (diseases of multiple peripheral nerves). The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance.

In one embodiment, a combination drug regimen may include drugs or compounds for the treatment or prevention of neurodegenerative disorders or secondary conditions associated with these conditions. Thus, a combination drug regimen may include one or more nicotinamide riboside ester and carbonate preparation or pharmaceutical composition of the invention that increase the level of NAD and/or activity of a sirtuin protein and one or more anti-neurodegeneration agents. For example, one or more nicotinamide riboside ester and carbonate preparation or pharmaceutical composition of the invention can be combined with an effective amount of one or more of: L-DOPA; a dopamine agonist; an adenosine A2A receptor antagonists; a COMT inhibitor; a MAO inhibitor; an NOS inhibitor; a sodium channel antagonist; a selective N-methyl D-aspartate (NMDA) receptor antagonists; an AMPA/kainate receptor antagonist; a calcium channel antagonist; a GABA-A receptor agonist; an acetyl-choline esterase inhibitor; a matrix metalloprotease inhibitor; an inhibitor of p38 MAP kinase or c-jun-N-terminal kinases; TPA; NDA antagonists; beta-interferons; growth factors; glutamate inhibitors; and/or as part of a cell therapy.

Exemplary N-NOS inhibitors include 4-(6-amino-pyridin-2-yl)-3-methoxyphenol 6-[4-(2-dimethylamino-ethoxy)-2-methoxy-phenyl]-pyridin-2-yl-amine, 6-[4-(2-dimethylamino-ethoxy)-2,3-dimethyl-phenyl]-pyridin-2-yl-amine, 6-[4-(2-pyrrolidinyl-ethoxy)-2,3-dimethyl-phenyl]-pyridin-2-yl-amine, 6-[4-(4-(n-methyl)piperidinyloxy)-2,3-dimethyl-phenyl]-pyridin-2-yl-amine, 6-[4-(2-dimethylamino-ethoxy)-3-methoxy-phenyl]-pyridin-2-yl-amine, 6-[4-(2-pyrrolidinyl-ethoxy)-3-methoxy-phenyl]-pyridin-2-yl-amine, 6-{4-[2-(6,7-dimethoxy-3,4-dihydro-1h-isoquinolin-2-yl)-ethoxy]-3-methoxy-phenyl}-pyridin-2-yl-amine, 6-{3-methoxy-4-[2-(4-phenethyl-piperazin-1-yl)-ethoxy]-phenyl}-pyridin-2-yl-amine, 6-{3-methoxy-4-[2-(4-methyl-piperazin-1-yl)-ethoxy]-phenyl}-pyridin-2-yl-amine, 6-{4-[2-(4-dimethylamino-piperidin-1-yl)-ethoxy]-3-methoxy-phenyl}-pyridin-2-yl-amine, 6-[4-(2-dimethylamino-ethoxy)-3-ethoxy-phenyl]-pyridin-2-yl-amine, 6-[4-(2-pyrrolidinyl-ethoxy)-3-ethoxy-phenyl]-pyridin-2-yl-amine, 6-[4-(2-dimethylamino-ethoxy)-2-isopropyl-phenyl]-pyridin-2-yl-amine, 4-(6-amino-pyridin-yl)-3-cyclopropyl-phenol 6-[2-cyclopropyl-4-(2-dimethylamino-ethoxy)-phenyl]-pyridin-2-yl-amine, 6-[2-cyclopropyl-4-(2-pyrrolidin-1-yl-ethoxy)-phenyl]-pyridin-2-yl-amine, 3-[3-(6-amino-pyridin-2yl)-4-cyclopropyl-phenoxy]-pyrrolidine-1-carboxylic acid tert-butyl ester 6-[2-cyclopropyl-4-(1-methyl-pyrrolidin-3-yl-oxy)-phenyl]-pyridin-2-yl-amine, 4-(6-amino-pyridin-2-yl)-3-cyclobutyl-phenol 6-[2-cyclobutyl-4-(2-dimethylamino-ethoxy)-phenyl]-pyridin-2-yl-amine, 6-[2-cyclobutyl-4-(2-pyrrolidin-1-yl-ethoxy)-phenyl]-pyridin-2-yl-amine, 6-[2-cyclobutyl-4-(1-methyl-pyrrolidin-3-yl-oxy)-phenyl]-pyridin-2-yl-amine, 4-(6-amino-pyridin-2-yl)-3-cyclopentyl-phenol 6-[2-cyclopentyl-4-(2-dimethylamino-ethoxy)-phenyl]-pyridin-2-yl-amine, 6-[2-cyclopentyl-4-(2-pyrrolidin-1 yl-ethoxy)-phenyl]-pyridin-2-yl-amine, 3-[4-(6-amino-pyridin-2yl)-3-methoxy-phenoxy]-pyrrolidine-1-carboxylic acid tert butyl ester 6-[4-(1-methyl-pyrrolidin-3-yl-oxy)-2-methoxy-phenyl]-pyridin-2-yl-amine, 4-[4-(6-amino-pyridin-2yl)-3-methoxy-phenoxy-]-piperidine-1-carboxylic acid tert butyl ester 6-[2-methoxy-4-(1-methyl-piperidin-4-yl-oxy)-phenyl]-pyridin-2-yl-amine, 6-[4-(allyloxy)-2-methoxy-phenyl]-pyridin-2-yl-amine, 4-(6-amino-pyridin-2-yl)-3-methoxy-6-allyl-phenol 12 and 4-(6-amino-pyridin-2-yl)-3-methoxy-2-allyl-phenol 13 4-(6-amino-pyridin-2-yl)-3-methoxy-6-propyl-phenol 6-[4-(2-dimethylamino-ethoxy)-2-methoxy-5-propyl-phenyl]-pyridin-yl-amine, 6-[2-isopropyl-4-(pyrrolidin-3-yl-oxy)-phenyl]-pyridin-2-yl-amine, 6-[2-isopropyl-4-(piperidin-3-yl-oxy)-phenyl]-pyridin-2-yl-amine, 6-[2-isopropyl-4-(1-methyl-azetidin-3-yl-oxy)-phenyl]-pyridin-2-yl-amine, 6-[2-isopropyl-4-(1-methyl-piperidin-4-yl-oxy)-phenyl]-pyridin-2-yl-amine, 6-[2-isopropyl-4-(1-methyl-pyrrolidin-3-yl-oxy)-phenyl]-pyridin-2-yl-amine 6-[2-isopropyl-4-(1-methyl-pyrrolidin-3-yl-oxy)-phenyl]-pyridin-2-yl-amine, 6-[2-isopropyl-4-(2-methyl-2-aza-bicyclo[2.2.1]hept-5-yl-oxy)-phenyl]-pyridin-2-yl-amine, 6-[4-(2-dimethylamino-ethoxy)-2-methoxy-phenyl]-pyridin-2-yl-amine, 6-{4-[2-(benzyl-methyl-amino)-ethoxy]-2-methoxy-phenyl}-pyridin-2-yl-amine, 6-[2-methoxy-4-(2-pyrrolidin-1-yl-ethoxy)-phenyl]-pyridin-2-yl-amine, 2-(6-amino-pyridin-2-yl)-5-(2-dimethylamino-ethoxy)-phenol 2-[4-(6-amino-pyridin-2-yl)-3-methoxy-phenoxy]-acetamide 6-[4-(2-amino-ethoxy)-2-methoxy-phenyl]-pyridin-2-yl-amine, 6-{4-[2-(3,4-dihydro-1 h-isoquinolin-2-yl)-ethoxy]-2-methoxy-phenyl}-pyridin-2-yl-amine, 2-[4-(6-amino-pyridin-2-yl)-3-methoxy-phenoxy]-ethanol 6-{2-methoxy-4-[2-(2,2,6,6-tetramethyl-piperidin-1-yl)-ethoxy]-phenyl}-pyridin-2-yl-amine, 6-{4-[2-(2,5-dimethyl-pyrrolidin-1-yl)-ethoxy]-2-methoxy-phenyl}-pyridin-2-yl-amine, 6-{4-[2-(2,5-dimethyl-pyrrolidin-1-yl)-ethoxy]-2-methoxy-phenyl}-pyridin-2-yl-amine, 2-[4-(6-amino-pyridin-2-yl)-3-methoxy-phenoxy]-1-(2,2,6,6-tetramethyl-piperidin-1-yl)-ethanone 6-[2-methoxy-4-(1-methyl-pyrrolidin-2-yl-methoxy)-phenyl]-pyridin-2-yl-amine, 6-[4-(2-dimethylamino-ethoxy)-2-propoxy-phenyl]-pyridin-2-yl-amine, 6-{4-[2-(benzyl-methyl-amino)-ethoxy]-2-propoxy-phenyl}-pyridin-2-yl-amine 6-[4-(2-ethoxy-ethoxy)-2-methoxy-phenyl]-pyridin-2-yl-amine, 6-[4-(2-dimethylamino-ethoxy)-2-isopropoxy-phenyl]-pyridin-2-yl-amine, 6-[4-(2-ethoxy-ethoxy)-2-isopropoxy-phenyl]-pyridin-2-yl-amine, 6-[2-methoxy-4-(3-methyl-butoxy)-phenyl]-pyridin-2-yl-amine, 6-[4-(2-dimethylamino-ethoxy)-2-ethoxy-phenyl]-pyridin-2-yl-amine, 6-{4-[2-(benzyl-methyl-amino)-ethoxy]-2-ethoxy-phenyl}-pyridin-2-yl-amine, 6-[2-ethoxy-4-(3-methyl-butoxy)-phenyl]- pyridin-2-yl-amine, 1-(6-amino-3-aza-bicyclo[3.1.0]hex-3-yl)-2-[4-(6-amino-pyridin-2-yl)-3-ethoxy-phenoxy]-ethanone 6-[2-ethoxy-4-(2-pyrrolidin-1-yl-ethoxy)-phenyl]-pyridin-2-yl-amine, 3-{2-[4-(6-amino-pyridin-2-yl)-3-ethoxy-phenoxy]-ethyl}-3-aza-bicyclo[3.1.0]hex-6-yl-amine, 1-(6-amino-3-aza-bicyclo[3.1.0]hex-3-yl)-2-[4-(6-amino-pyridin-2-yl)-3-methoxy-phenoxy]-ethanone 3-{2-[4-(6-amino-pyridin-2-yl)-3-methoxy-phenoxy]-ethyl}-3-aza-bicyclo[3.-1.0]hex-6-yl-amine, 6-[2-isopropoxy-4-(2-pyrrolidin-1-yl-ethoxy)-phenyl]-pyridin-2-yl-amine, 6-{4-[2-(benzyl-methyl-amino)-ethoxy]-2-isopropoxy-phenyl-}-pyridin-2-yl-amine, 6-[4-(2-dimethylamino-ethoxy)-2-methoxy-5-propyl-phenyl]-pyridin-2-yl-amine, 6-[5-allyl-4-(2-dimethylamino-ethoxy)-2-methoxy-phenyl]-pyridin-2-yl-amine, 6-[5-allyl-2-methoxy-4-(2-pyrrolidin-1-yl-ethoxy)-phenyl]-pyridin-2-yl-amine, 6-[3-allyl-4-(2-dimethylamino-ethoxy)-2-methoxy-phenyl]-pyridin-2-yl-amine, 6-[2-methoxy-4-(pyrrolidin-3-yl-oxy)-phenyl]-pyridin-2-yl-amine, 6-[2-methoxy-4-(1-methyl-pyrrolidin-3-yl-oxy)-phenyl]-pyridin-2-yl-amine, 6-[2-ethoxy-4-(pyrrolidin-3-yl-oxy)-phenyl]-pyridin-2-yl-amine, 6-[2-isopropoxy-4-(pyrrolidin-3-yl-oxy)-phenyl]-pyridin-2-yl-amine, 6-[2-methoxy-4-(piperidin-4-yl-oxy)-phenyl]-pyridin-2-yl-amine, 6-[2-methoxy-4-(2,2,6,6-tetramethyl-piperidin-4-yl-oxy)-phenyl]-pyridin-2-yl-amine, 6-[2-isopropoxy-4-(pyrrolidin-3-yl-oxy)-phenyl]-pyridin-2-yl-amine, 3-[4-(6-amino-pyridin-2-yl)-3-methoxy-phenoxy]-azetidine-1-carboxylic acid tert-butyl ester 6-[4-(azetidin-3-yl-oxy)-2-methoxy-phenyl]-pyridin-2-yl-amine, 6-[2-methoxy-4-(1-methyl-azetidin-3-yl-oxy)-phenyl]-pyridin-2-yl-amine, 6-[2-isopropoxy-4-(pyrrolidin-3-yl-oxy)-phenyl]-pyridin-2-yl-amine, 6-[2-isopropoxy-4-(pyrrolidin-3-yl-oxy)-phenyl]-pyridin-2-yl-amine, 6-[2-methoxy-4-(pyrrolidin-3-yl-oxy)-phenyl]-pyridin-2-yl-amine, 6-[2-methoxy-4-(1-methyl-pyrrolidin-3-yl-oxy)-phenyl]-pyridin-2-yl-amine, 6-[2-methoxy-4-(1-methyl-pyrrolidin-3-yl-oxy)-phenyl]-pyridin-2-yl-amine, 6-[2-methoxy-4-(2-methyl-2-aza-bicyclo[2.2.1]hept-5-yl-oxy)-phenyl]-pyridin-2-yl-amine, 6-[2-methoxy-4-(1-methyl-piperidin-4-yl-oxy)-phenyl]-pyridin-2-yl-amine, 6-[4-(1-ethyl-piperidin-4-yl-oxy)-2-methoxy-phenyl]-pyridin-2-yl-amine, 6-[5-allyl-2-methoxy-4-(1-methyl-pyrrolidin-3-yl-oxy)-phenyl]-pyridin-2-yl-amine, 6-[4-(2-dimethylamino-ethoxy)-2,6-dimethyl-phenyl]-pyridin-2-yl-amine, 6-[2,6-dimethyl-4-(3-piperidin-1-yl-propoxy)-phenyl]-pyridin-2-yl-amine, 6-[2,6-dimethyl-4-(2-pyrrolidin-1-yl-ethoxy)-phenyl]-pyridin-2-yl-amine, 6-{2,6-dimethyl-4-[3-(4-methyl-piperazin-1-yl)-propoxy]-phenyl}-pyridin-2-yl-amine, 6-[2,6-dimethyl-4-(2-morpholin-4-yl-ethoxy)-phenyl]-pyridin-2-yl-amine, 6-{4-[2-(benzyl-methyl-amino)-ethoxy]-2,6-dimethyl-phenyl}-pyridin-2-yl-amine, 2-[4-(6-amino-pyridin-2-yl)-3,5-dimethyl-phenoxy]-acetamide 6-[4-(2-amino-ethoxy)-2,6-dimethyl-phenyl]-pyridin-2-yl-amine, 6-[2-isopropyl-4-(2-pyrrolidin-1-yl-ethoxy)-phenyl]-pyridin-2-yl-amine, 2-(2,5-dimethyl-pyrrolidin-1-yl)-6-[2-isopropyl-4-(2-pyrrolidin-1-yl-ethoxy)-phenyl]-pyridine 6-{4-[2-(3,5-dimethyl-piperidin-1-yl)-ethoxy]-2-isopropyl-phenyl}-pyridin-2-yl-amine, 6-[4-(2-dimethylamino-ethoxy)-2-isopropyl-phenyl]-pyridin-2-yl-amine, 6-[2-tert-butyl-4-(2-dimethylamino-ethoxy)-phenyl]-pyridin-2-yl-amine, 6-[2-tert-butyl-4-(2-pyrrolidin-1-yl-ethoxy)-phenyl-]-pyridin-2-yl-amine, 6-[4-(2-pyrrolidinyl-ethoxy)-2, 5-dimethyl-phenyl]-pyridin-2-yl-amine, 6-[4-(2-dimethylamino-ethoxy)-2, 5-dimethyl-phenyl]-pyridin-2-yl-amine, 6-[4-(2-(4-phenethylpiperazin-1-yl)-ethoxy)-2,5-dimethyl-phenyl]-pyridin-2-yl-amine, 6-[2-cyclopropyl-4-(2-dimethylamino-1-methyl-ethoxy)-phenyl]-pyridin-2-yl-amine, 6-[cyclobutyl-4-(2-dimethylamino-1-methyl-ethoxy)-phenyl]-pyridin-2-yl-amine, 6-[4-(allyloxy)-2-cyclobutyl-phenyl]-pyridin-2ylamine, 2-allyl-4-(6-amino-pyridin-2-yl)-3-cyclobutyl-phenol and 2-allyl-4-(6-amino-pyridin-2-yl)-5-cyclobutyl-phenol 4-(6-amino-pyridin-2yl)-5-cyclobutyl-2-propyl-phenol 4-(6-amino-pyridin-2yl)-3-cyclobutyl-2-propyl-phenol 6-[2-cyclobutyl-4-(2-dimethylamino-1-methyl-ethoxy)-5-propyl-phenyl]-pyridin-2-yl-amine, 6-[2-cyclobutyl-4-(2-dimethylamino-1-methyl-ethoxy)-3-propy-1-phenyl]-pyridin-2-yl-amine, 6-[2-cyclobutyl-4-(2-dimethylamino-ethoxy)-5-propyl-phenyl]-pyridin-2-yl-amine, 6-[2-cyclobutyl-4-(2-dimethylamino-ethoxy)-3-propyl-phenyl]-pyridin-2-yl-amine, 6-[2-cyclobutyl-4-(1-methyl-pyrrolidin-3-yl-oxy)-5-propyl-phenyl]-pyridin-2-yl-amine, 6-[cyclobutyl-4-(1-methy-1-pyrrolidin-3-yl-oxy)-3-propyl-phenyl]-pyridin-2-yl-amine, 2-(4-benzyloxy-5-hydroxy-2-methoxy-phenyl)-6-(2, 5-dimethyl-pyrrol-1-yl)-pyridine 6-[4-(2-dimethylamino-ethoxy)-5-ethoxy-2-methoxy-phenyl]-pyridin-2-yl-amine, 6-[5-ethyl-2-methoxy-4-(1-methyl-piperidin-4-yl-oxy)-phenyl]-pyridin-2-yl-amine, 6-[5-ethyl-2-methoxy-4-(piperidin-4-yl-oxy)-phenyl]-pyridin-2-yl-amine, 6-[2,5-dimethoxy-4-(1-methyl-pyrrolidin-3-yl-oxy)-phenyl]-pyridin-2-yl-amine, 6-[4-(2-dimethylamino-ethoxy)-5-ethyl-2-methoxy-phenyl]-pyridin-2-yl-amine.

Exemplary NMDA receptor antagonist include (+)-(1S, 2S)-1-(4-hydroxy-phenyl)-2-(4-hydroxy-4-phenylpiperidino)-1-propanol, (1S,2S)-1-(4-hydroxy-3-methoxyphenyl)-2-(4-hydroxy-4-phenylpiperidino)-1-propanol, (3R, 4S)-3-(4-(4-fluorophenyl)-4-hydroxypiperidin-1-yl-)-chroman-4,7-diol, (1R*,2R*)-1-(4-hydroxy-3-methylphenyl)-2-(4-(4-fluoro-phenyl)-4-hydroxypiperidin-1-yl)-propan-1-ol-mesylate or a pharmaceutically acceptable acid addition salt thereof.

Exemplary dopamine agonists include ropininole; L-dopa decarboxylase inhibitors such as carbidopa or benserazide, bromocriptine, dihydroergocryptine, etisulergine, AF-14, alaptide, pergolide, piribedil; dopamine D1 receptor agonists such as A-68939, A-77636, dihydrexine, and SKF-38393; dopamine D2 receptor agonists such as carbergoline, lisuride, N-0434, naxagolide, PD-118440, pramipexole, quinpirole and ropinirole; dopamine/beta-adrenegeric receptor agonists such as DPDMS and dopexamine; dopamine/5-HT uptake inhibitor/5-HT-1A agonists such as roxindole; dopamine/opiate receptor agonists such as NIH-10494; alpha2-adrenergic antagonist/dopamine agonists such as terguride; alpha2-adrenergic antagonist/dopamine D2 agonists such as ergolines and talipexole; dopamine uptake inhibitors such as GBR-12909, GBR-13069, GYKI-52895, and NS-2141; monoamine oxidase-B inhibitors such as selegiline, N-(2-butyl)-N-methylpropargylamine, N-methyl-N-(2-pentyl)propargylamine, AGN-1133, ergot derivatives, lazabemide, LU-53439, MD-280040 and mofegiline; and COMT inhibitors such as CGP-28014.

Exemplary acetyl cholinesterase inhibitors include donepizil, 1-(2-methyl-1H-benzimidazol-5-yl)-3-[1-(phenylmethyl)-4-piperidinyl]-1-propanone; 1-(2-phenyl-1H-benzimidazol-5-yl)-3-[1-(phenylmethyl)-4-piperidinyl]-1-propanone; 1-(1-ethyl-2-methyl-1H-benzimidazol-5-yl)-3-[1-(phenylmethyl)-4-piperidinyl]-1-propanone; 1-(2-methyl-6-benzothiazolyl)-3-[1-(phenylmethyl)-4-piperidinyl]-1-propanone; 1-(2-methyl-6-benzothiazolyl)-3-[1-[(2-methyl-4-thiazolyl)methyl]-4-piperidinyl]-1-propanone; 1-(5-methyl-benzo[b]thien-2-yl)-3-[1-(phenylmethyl)4-piperidinyl]-1-propanone; 1-(6-methyl-benzo[b]thien-2-yl)-3-[1-(phenylmethyl)-4-piperidinyl]-1-propanone; 1-(3,5-dimethyl-benzo[b]thien-2-yl)-3-[1-

(phenylmethyl)-4-piperidin-yl]-1-propanone; 1-(benzo[b]thien-2-yl)-3-[1-(phenylmethyl)-4-piperidinyl]-1-propanone; 1-(benzofuran-2-yl)-3-[1-(phenylmethyl)-4-piperidinyl]-1-propanone; 1-(1-phenylsulfonyl-6-methyl-indol-2-yl)-3-[1-(phenylmethyl)-4-piperidinyl]-1-propanone; 1-(6-methyl-indol-2-yl)-3-[1-(phenylmethyl)-4-piperidinyl]-1-propanone; 1-(1-phenylsulfonyl-5-amino-indol-2-yl)-3-[1-(phenylmethyl)-4-piperidinyl]-1-propanone; 1-(5-amino-indol-2-yl)-3-[1-(phenylmethyl)-4-piperidinyl]-1-propanone; and 1-(5-acetylamino-indol-2-yl)-3-[1-(phenylmethyl)-4-piperidinyl]-1-propanone; 1-(6-quinolyl)-3-[1-(phenylmethyl)-4-piperidinyl]-1-propanone; 1-(5-indolyl)-3-[1-(phenylmethyl)-4-piperidinyl]-1-propanone; 1-(5-benzthienyl)-3-[1-(phenylmethyl)-4-piperidinyl]-1-propanone; 1-(6-quinazolyl)-3-[1-(phenylmethyl)-4-piperidinyl]-1-propanone; 1-(6-benzoxazolyl)-3-[1-(phenylmethyl)-4-piperidinyl]-1-propanone; 1-(5-benzofuranyl)-3-[1-(phenylmethyl)-4-piperidinyl]-1-propanone; 1-(5-methyl-benzimidazol-2-yl)-3-[1-(phenylmethyl)-4-piperidinyl]-1-propa-none; 1-(6-methyl-benzimidazol-2-yl)-3-[1-(phenylmethyl)-4-piperidinyl]-1-propanone; 1-(5-chloro-benzo[b]thien-2-yl)-3-[1-(phenylmethyl)-4-piperidin-yl]-1-propanone; 1-(5-azaindol-2-yl)-3-[1-(phenylmethyl)4-piperidinyl]-1-propanone; 1-(6-azabenzo[b]thien-2-yl)-3-[1-(phenylmethyl)-4-piperidinyl]-1-propanone; 1-(1H-2-oxo-pyrrolo[2',3',5,6]benzo[b]thieno-2-yl)-3-[1-(phenylmethyl)-4-piperidinyl]-1-propanone; 1-(6-methyl-benzothiazol-2-yl)-3-[1-(phenylmethyl)-4-piperidinyl]-1-propanone; 1-(6-methoxy-indol-2-yl)-3-[1-(phenylmethyl)-4-piperidinyl]-1-propanone; 1-(6-methoxy-benzo[b]thien-2-yl)-3-[1-(phenylmethyl)-4-piperidinyl]-1-propanone; 1-(6-acetylamino-benzo[b]thien-2-yl)-3-[1-(phenylmethyl)-4-piperidinyl]-1-propanone; 1-(5-acetylamino-benzo[b]thien-2-yl)-3-[1-(phenylmethyl-)-4-piperidinyl]-1-propanone; 6-hydroxy-3-[2-[1-(phenylmethyl)-4-piperidin-yl]ethyl]-1,2-benzisoxazole; 5-methyl-3-[2-[1-(phenylmethyl)-4-piperidinyl-]ethyl]-1,2-benzisoxazole; 6-methoxy-3 [2-[1 (phenylmethyl)-4-piperidinyl]ethyl]-1,2-benzisoxazole; 6-acetamide-3-[2-[1-(phenylmethyl)-4-piperidinyl]-ethyl]-1,2-benzisoxazole; 6-amino-3-[2-[1-(phenymethyl)-4-piperidinyl]ethyl]-1,2-benzisoxazole; 6-(4-morpholinyl)-3-[2-[1-(phenylmethyl)-4-piperidin-yl]ethyl]-1,2-benzisoxazole; 5,7-dihydro-3-[2-[1-(phenylmethyl)-4-piperidinyl]ethyl]-6H-pyrrolo[4,5-f]-1,2-benzisoxazol-6-one; 3-[2-[1-(phenyl-methyl)-4-piperidinyl]ethyl]-1,2-benzisothiazole; 3-[2-[1-(phenylmethyl)-4-piperidinyl]ethenyl]-1,2-benzisoxazole; 6-phenylamino-3-[2-[1-(phenylmethyl)-4-piperidinyl]ethyl]-1,2,-benzisoxazole; 6-(2-thiazoly)-3-[2-[1-(phenylm-ethyl)-4-piperidinyl]ethyl]-1,2-benzisoxazole; 6-(2-oxazolyl)-3-[2-[1-(phenylmethyl)-4-piperidinyl]ethyl]-1,2-benzisoxazole; 6-pyrrolidinyl-3-[2-[1-(phenylmethyl)-4-piperidinyl]ethyl]-1,-2-benzisoxazole; 5,7-dihydro-5,5-dimethyl-3-[2-[1-(phenylmethyl)-4-piperidinyl]ethyl]-6H-pyrrolo[4, 5-f]-1,2-benzisoxazole-6-one; 6,8-dihydro-3-[2-[1-(phenylmethyl)-4-piperidinyl]ethyl]-7H-pyrrolo[5,4-g]-1,2-benzisoxazole-7-one; 3-[2-[1-(phenylmethyl)-4-piperidinyl]ethyl]-5,6,-8-trihydro-7H-isoxazolo[4,5-g]-quinolin-7-one; 1-benzyl-4-((5,6-dimethoxy-1-indanon)-2-yl)methylpiperidine, 1-benzyl-4-((5,6-dimethoxy-1-indanon)-2-ylidenyl)methylpiperidine, 1-benzyl-4-((5-methoxy-1-indanon)-2-yl)methylpiperidine, 1-benzyl-4-((5, 6-diethoxy-1-indanon)-2-yl)methylpiperidine, 1-benzyl-4-((5,6-methnylenedioxy-1-indanon)-2-yl)methylpiperidine, 1-(m-nitrobenzyl)-4-((5,6-dimethoxy-1-indanon)-2-yl) methylpiperidine, 1-cyclohexymethyl-4-((5,6-dimethoxy-1-indanon)-2-yl)methylpiperidine, 1-(m-florobenzyl)-4-((5,6-dimethoxy-1-indanon)-2-yl)methylpiperidine, 1-benzyl-4-((5,6-dimethoxy-1-indanon)-2-yl)propylpiperidine, and 1-benzyl-4-((5-isopropoxy-6-methoxy-1-indanon)-2-yl) methylpiperidine.

Exemplary calcium channel antagonists include diltiazem, omega-conotoxin GVIA, methoxyverapamil, amlodipine, felodipine, lacidipine, and mibefradil.

Exemplary GABA-A receptor modulators include clomethiazole; IDDB; gaboxadol (4,5,6,7-tetrahydroisoxazolo[5,4-c]pyridin-3-ol); ganaxolone (3-alpha-hydroxy-3-beta-methyl-5-alpha-pregnan-20-one); fengabine (2-[(butylimino)-(2-chlorophenyl)methyl]-4-chlorophenol); 2-(4-methoxyphenyl)-2,5,6,7,8,9-hexahydro-pyrazolo[4,3-c]cinnolin-3-one; 7-cyclobutyl-6-(2-methyl-2H-1,2,4-triazol-3-ylmethoxy)-3-phenyl-1,2,4-triazolo[4,3-b] pyridazine; (3-fluoro-4-methylphenyl)-N-({-1-[(2-methylphenyl)methyl]-benzimidazol-2-yl}methyl)-N-pentylcarboxamide; and 3-(aminomethyl)-5-methylhexanoic acid.

Exemplary potassium channel openers include diazoxide, flupirtine, pinacidil, levcromakalim, rilmakalim, chromakalim, PCO-400 and SKP-450 (2-[2"(1",3"-dioxolone)-2-methyl]-4-(2'-oxo-1'-pyrrolidinyl)-6-nitro-2H-1-benzopyran).

Exemplary AMPA/kainate receptor antagonists include 6-cyano-7-nitroquinoxalin-2,3-di-one (CNQX); 6-nitro-7-sulphamoylbenzo[f]quinoxaline-2,3-dione (NBQX); 6,7-dinitroquinoxaline-2,3-dione (DNQX); 1-(4-aminophenyl)-4-methyl-7,8-methylenedioxy-5H-2,3-benzodiazepine hydrochloride; and 2,3-dihydroxy-6-nitro-7-sulfamoyl-benzo-[f]quinoxaline.

Exemplary sodium channel antagonists include ajmaline, procainamide, flecainide and riluzole.

Exemplary matrix-metalloprotease inhibitors include 4-[4-(4-fluorophenoxy)-benzenesulfonylamino]tetrahydro-pyran-4-carboxylic acid hydroxyamide; 5-methyl-5-(4-(4'-fluorophenoxy)-phenoxy)-pyrimidine-2,4,6-trione; 5-n-butyl-5-(4-(4'-fluorophenoxy)-phenoxy)-pyrimidine-2,4,6-trione and prinomistat.

Exemplary inhibitors of p38 MAP kinase and c-jun-N-terminal kinases include pyridyl imidazoles, such as PD 169316, isomeric PD 169316, SB 203580, SB 202190, SB 220026, and RWJ 67657. Others are described in U.S. Pat. No. 6,288,089, and incorporated by reference herein.

In an exemplary embodiment, a combination therapy for treating or preventing MS comprises a therapeutically effective amount of a nicotinamide riboside ester and carbonate preparation or pharmaceutical composition of the invention that increase the level of NAD and/or activity of a sirtuin protein and one or more of Avonex® (interferon beta-1a), Tysabri® (natalizumab), or Fumaderm® (BG-12/Oral Fumarate).

In another embodiment, a combination therapy for treating or preventing diabetic neuropathy or conditions associated therewith comprises a therapeutically effective amount of a nicotinamide riboside ester and carbonate preparation or pharmaceutical composition of the invention that increase the level of NAD and/or activity of a sirtuin protein and one or more of tricyclic antidepressants (TCAs) (including, for example, imipramine, amytriptyline, desipramine and nortriptyline), selective serotonin reuptake inhibitors (SSRIs) (including, for example, fluoxetine, paroxetine, sertralene, and citalopram) and antiepileptic drugs (AEDs) (including, for example, gabapentin, carbamazepine, and topimirate).

Blood Coagulation Disorders

In other aspects, nicotinamide riboside ester and carbonate preparations and pharmaceutical compositions of the invention that increase the level of NAD and/or activity of a sirtuin protein can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. After initiation of clotting, blood coagulation proceeds through the sequential activation of certain plasma proenzymes to their enzyme forms (see, for example, Coleman, R. W. et al. (eds.) Hemostasis and Thrombosis, Second Edition, (1987)). These plasma glycoproteins, including Factor XII, Factor XI, Factor IX, Factor X, Factor VII, and prothrombin, are zymogens of serine proteases. Most of these blood clotting enzymes are effective on a physiological scale only when assembled in complexes on membrane surfaces with protein cofactors such as Factor VIII and Factor V. Other blood factors modulate and localize clot formation, or dissolve blood clots. Activated protein C is a specific enzyme that inactivates procoagulant components. Calcium ions are involved in many of the component reactions. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place. It involves a cascade of complicated and regulated biochemical reactions between circulating blood proteins (coagulation factors), blood cells (in particular platelets), and elements of an injured vessel wall.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering a nicotinamide riboside ester or carbonate preparation or pharmaceutical composition of the invention that increases the level of NAD and/or activity of a sirtuin protein. The compositions and methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites. Examples of thrombotic disorders include, but are not limited to, thromboembolism, deep vein thrombosis, pulmonary embolism, stroke, myocardial infarction, miscarriage, thrombophilia associated with antithrombin III deficiency, protein C deficiency, protein S deficiency, resistance to activated protein C, dysfibrinogenemia, fibrinolytic disorders, homocystinuria, pregnancy, inflammatory disorders, myeloproliferative disorders, arteriosclerosis, angina, e.g., unstable angina, disseminated intravascular coagulation, thrombotic thrombocytopenic purpura, cancer metastasis, sickle cell disease, glomerular nephritis, and drug induced thrombocytopenia (including, for example, heparin induced thrombocytopenia). In addition, nicotinamide riboside ester and carbonate preparations and pharmaceutical compositions of the invention that increase the level of NAD and/or activity of a sirtuin protein may be administered to prevent thrombotic events or to prevent re-occlusion during or after therapeutic clot lysis or procedures such as angioplasty or surgery.

In another embodiment, a combination drug regimen may include drugs or compounds for the treatment or prevention of blood coagulation disorders or secondary conditions associated with these conditions. Thus, a combination drug regimen may include a nicotinamide riboside ester and carbonate preparation or pharmaceutical composition of the invention that increases the level of NAD and/or activity of a sirtuin protein and one or more anti-coagulation or anti-thrombosis agents. For example, one or more nicotinamide riboside ester and carbonate preparations or pharmaceutical compositions can be combined with an effective amount of one or more of: aspirin, heparin, and oral Warfarin that inhibits Vit K-dependent factors, low molecular weight heparins that inhibit factors X and II, thrombin inhibitors, inhibitors of platelet GP IIbIIIa receptors, inhibitors of tissue factor (TF), inhibitors of human von Willebrand factor, inhibitors of one or more factors involved in hemostasis (in particular in the coagulation cascade). In addition, nicotinamide riboside ester and carbonate preparations or pharmaceutical compositions of the invention that increase the level of NAD and/or activity of a sirtuin protein can be combined with thrombolytic agents, such as t-PA, streptokinase, reptilase, TNK-t-PA, and staphylokinase.

Weight Control

In another aspect, nicotinamide riboside ester and carbonate preparations and pharmaceutical compositions of the invention that increase the level of NAD and/or the activity of a sirtuin protein may be used for treating or preventing weight gain or obesity in a subject. For example, nicotinamide riboside ester and carbonate preparations and pharmaceutical compositions of the invention that increase the level of NAD and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, nicotinamide riboside ester and carbonate preparations and pharmaceutical compositions of the invention that increase the level of NAD and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem). Stunkard A J, Wadden T A. (Editors) Obesity: theory and therapy, Second Edition. New York: Raven Press, 1993. Finally, patients with AIDS can develop lipodystrophy or insulin resistance in response to combination therapies for AIDS.

In another embodiment, nicotinamide riboside ester and carbonate preparations and pharmaceutical compositions of the invention that increase the level of NAD and/or activity of a sirtuin protein may be used for inhibiting adipogenesis or fat cell differentiation, whether in vitro or in vivo. In particular, high circulating levels of insulin and/or insulin like growth factor (IGF) 1 will be prevented from recruiting preadipocytes to differentiate into adipocytes. Such methods may be used for treating or preventing obesity.

In other embodiments, nicotinamide riboside ester and carbonate preparations and pharmaceutical compositions of the invention that increase the level of NAD and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In other embodiments, nicotinamide riboside ester and carbonate preparations and pharmaceutical compositions of the invention may be used to treat a subject who has cachexia or may be likely to develop cachexia. A combination of agents may also be administered. A method may further comprise monitoring in the subject the state of the disease or the level of NAD and/or the activation of sirtuins, for example, in adipose tissue. Methods for promoting appetite and/or weight gain may include, for example, prior identifying a subject as being in need of decreased fat or lipid metabolism, e.g., by weighing the subject, determining the BMI of the subject, or evaluating fat content of the subject or sirtuin activity in cells of the subject. The method may also include monitoring the subject, e.g., during and/or after administration of the nicotinamide riboside ester and carbonate preparations and pharmaceutical compositions of the invention. The administering can include one or more dosages, e.g., delivered in boluses or continuously. Monitoring can include evaluating a hormone or a metabolite. Exemplary hormones include leptin, adiponectin, resistin, and insulin. Exemplary metabolites include triglyercides, cholesterol, and fatty acids.

A method for modulating weight may further comprise monitoring the weight of the subject and/or the level of NAD (e.g. intracellular NAD levels, levels of NAD in tissues or plasma, and/or overall NAD levels in an organism) and/or modulation of sirtuins, for example, in adipose tissue.

In an exemplary embodiment, a nicotinamide riboside ester or carbonate preparation or pharmaceutical composition of the invention that increased the level of NAD and/or the activity of a sirtuin protein may be administered as a combination therapy for treating or preventing weight gain or obesity. For example, one or more nicotinamide riboside ester and carbonate preparations or pharmaceutical compositions of the invention that increase the level of NAD and/or activity of a sirtuin protein may be administered in combination with one or more anti-obesity agents. Exemplary anti-obesity agents include, for example, phenylpropanolamine, ephedrine, pseudoephedrine, phentermine, a cholecystokinin-A agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (leptin), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

In another embodiment, nicotinamide riboside ester and carbonate preparations and pharmaceutical compositions of the invention that increase the level of NAD and/or activity of a sirtuin protein may be administered to reduce drug-induced weight gain. For example, a nicotinamide riboside ester or carbonate preparation or a pharmaceutical composition of the invention that increases the level of NAD and/or activity of a sirtuin protein may be administered as a combination therapy with medications that may stimulate appetite or cause weight gain, in particular, weight gain due to factors other than water retention. Examples of medications that may cause weight gain, include for example, diabetes treatments, including, for example, sulfonylureas (such as glipizide and glyburide), thiazolidinediones (such as pioglitazone and rosiglitazone), meglitinides, nateglinide, repaglinide, sulphonylurea medicines, and insulin; anti-depressants, including, for example, tricyclic antidepressants (such as amitriptyline and imipramine), irreversible monoamine oxidase inhibitors (MAOIs), selective serotonin reuptake inhibitors (SSRIs), bupropion, paroxetine, and mirtazapine; steroids, such as, for example, prednisone; hormone therapy; lithium carbonate; valproic acid; carbamazepine; chlorpromazine; thiothixene; beta blockers (such as propranolo); alpha blockers (such as clonidine, prazosin and terazosin); and contraceptives including oral contraceptives (birth control pills) or other contraceptives containing estrogen and/or progesterone (Depo-Provera, Norplant, Ortho), testosterone or Megestrol. In another exemplary embodiment, nicotinamide riboside ester or carbonate preparations and pharmaceutical compositions of the invention that increase the level of NAD and/or the activity of a sirtuin protein may be administered as part of a smoking cessation program to prevent weight gain or reduce weight already gained.

Metabolic Disorders/Diabetes

In another aspect, nicotinamide riboside ester and carbonate preparations and pharmaceutical compositions of the invention that increase the level of NAD and/or activity of a sirtuin protein may be used for treating or preventing a metabolic disorder, such as insulin-resistance, a pre-diabetic state, type II diabetes, and/or complications thereof. Administration of a nicotinamide riboside ester and carbonate preparation or pharmaceutical composition of the invention that increases the level of NAD and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, nicotinamide riboside ester and carbonate preparations and pharmaceutical compositions of the invention that increase the level of NAD and/or activity of a sirtuin protein may be administered as a combination therapy for treating or preventing a metabolic disorder. For example, one or more nicotinamide riboside ester or carbonate preparationa or a pharmaceutical composition of the invention that increases the level of NAD and/or activity of a sirtuin protein may be administered in combination with one or more anti-diabetic agents. Exemplary anti-diabetic agents include, for example, an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a peroxisome proliferator-activated receptor-γ (PPAR-γ) ligand such as troglitazone, rosaglitazone, pioglitazone or GW-1929, a sulfonylurea, glipazide, glyburide, or chlorpropamide wherein the amounts of the first and second compounds result in a therapeutic effect. Other anti-diabetic agents include a glucosidase inhibitor, a glucagon-like peptide-1 (GLP-1), insulin, a PPAR α/γ dual agonist, a meglitimide and an αP2 inhibitor. In an exemplary embodiment, an anti-diabetic agent may be a dipeptidyl peptidase IV (DP-IV or DPP-IV) inhibitor, such as, for example LAF237 from Novartis (NVP DPP728; 1-[[[2-[(5-cyanopyridin-2-yl)amino] ethyl]amino]acetyl]-2-cyano-(S)-pyrrolidine) or MK-04301 from Merck (see e.g., Hughes et al., Biochemistry 38: 11597-603 (1999)).

Inflammatory Diseases

In other aspects, nicotinamide riboside ester and carbonate preparations and pharmaceutical compositions of the invention that increase the level of NAD and/or activity of a sirtuin protein can be used to treat or prevent a disease or disorder associated with inflammation. Nicotinamide riboside ester and carbonate preparations and pharmaceutical compositions of the invention that increase the level of NAD and/or activity of a sirtuin protein may be administered prior to the onset of, at, or after the initiation of inflammation. When used prophylactically, the compositions are preferably provided in advance of any inflammatory response or symptom. Administration of the compositions may prevent or attenuate inflammatory responses or symptoms.

Exemplary inflammatory conditions include, for example, multiple sclerosis, rheumatoid arthritis, psoriatic arthritis, degenerative joint disease, spondouloarthropathies, gouty arthritis, systemic lupus erythematosus, juvenile arthritis, rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, nicotinamide riboside ester and carbonate preparations and pharmaceutical compositions of the invention that increase the level of NAD and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, nicotinamide riboside ester and carbonate preparations and pharmaceutical compositions of the invention that increase the level of NAD and/or the activity of a sirtuin protein may be used to treat autoimmune diseases and/or inflammation associated with autoimmune diseases such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In certain embodiments, one or more nicotinamide riboside ester and carbonate preparations or a pharmaceutical composition of the invention that increases the level of NAD and/or the activity of a sirtuin protein may be taken alone or in combination with other compounds useful for treating or preventing inflammation. Exemplary anti-inflammatory agents include, for example, steroids (e.g., cortisol, cortisone, fludrocortisone, prednisone, 6-alpha-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

Further examples of anti-inflammatory agents include, for example, aceclofenac, acemetacin, 6-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, .alpha.-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, carprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocortolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydrocortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In an exemplary embodiment, a nicotinamide riboside ester or carbonate preparation or pharmaceutical composition of the invention that increases the level of NAD and/or the activity of a sirtuin protein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, lumiracoxib, 2-(3,5-difluorophenyl)-3-[4-(methylsulfonyl)phenyl]-2-cyclopenten-1-one, (S)-6,8-dichloro-2-(trifluoromethyl)-2H-1-benzopyran-3-carboxylic acid, 2-(3,4-difluorophenyl)-4-(3-hydroxy-3-methyl-1-butoxy)-5-[4-(methylsulfonyl)phenyl]-3-(2H)-pyridazinone, 4-[5-(4-fluorophenyl)-3-(trifluoromethyl)-1H-pyrazol-1-yl]benzenesulfonamide, tert-butyl 1 benzyl-4-[(4-oxopiperidin-1-yl}sulfonyl]piperidine-4-carboxylate, 4-[5-(phenyl)-3-(trifluoromethyl)-1H-pyrazol-1-yl]benzenesulfonamide, salts and prodrugs thereof.

Other Uses

Nicotinamide riboside ester and carbonate preparations and pharmaceutical or cosmetic compositions of the invention that increase the level of NAD and/or the activity of a sirtuin protein may be used for treating or preventing viral infections (such as infections by influenza, herpes or papilloma virus) or as antifungal agents. In certain embodiments, nicotinamide riboside ester and carbonate preparations and pharmaceutical or cosmetic compositions of the invention that increase the level of NAD and/or the activity of a sirtuin protein may be administered as part of a combination drug therapy with another therapeutic agent for the treatment of viral diseases, including, for example, acyclovir, ganciclovir and zidovudine. In another embodiment, nicotinamide riboside ester and carbonate preparations and pharmaceutical or cosmetic compositions of the invention that increase the level of NAD and/or the activity of a sirtuin protein may be administered as part of a combination drug therapy with another anti-fungal agent including, for example, topical anti-fungals such as ciclopirox, clotrimazole, econazole, miconazole, nystatin, oxiconazole, terconazole, and tolnaftate, or systemic anti-fungal such as fluconazole (Diflucan), itraconazole (Sporanox), ketoconazole (Nizoral), and miconazole (Monistat I.V.).

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, nicotinamide riboside ester and carbonate preparations and pharmaceutical or cosmetic compositions of the invention may be administered to farm animals to improve their ability to withstand farming conditions longer.

Nicotinamide riboside ester and carbonate preparations and pharmaceutical or cosmetic compositions of the invention that increase the level of NAD and/or the activity of a sirtuin protein may also be used to increase lifespan, stress resistance, and resistance to apoptosis in plants. In one embodiment, a nicotinamide riboside ester and carbonate preparation or composition of the invention is applied to plants, e.g., on a periodic basis, or to fungi. In another embodiment, plants are genetically modified to produce a compound. In another embodiment, plants and fruits are treated with a nicotinamide riboside ester and carbonate preparation or composition of the invention prior to picking and shipping to increase resistance to damage during shipping. Plant seeds may also be contacted with a nicotinamide riboside ester and carbonate preparation or composition described herein, e.g., to preserve them.

In other embodiments, a nicotinamide riboside ester or carbonate preparation or composition of the invention that increase the level of NAD and/or the activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Nicotinamide riboside ester and carbonate preparations or compositions of the invention that increase the level of NAD and/or activity of a sirtuin protein may also be used to increase lifespan, stress resistance and resistance to apoptosis in insects. In this embodiment, a nicotinamide riboside ester and carbonate preparation or composition of the invention would be applied to useful insects, e.g., bees and other insects that are involved in pollination of plants. In a specific embodiment, a nicotinamide riboside ester and carbonate preparation or composition of the invention would be applied to bees involved in the production of honey. Generally, the methods described herein may be applied to any organism, e.g., eukaryote, that may have commercial importance. For example, they can be applied to fish (aquaculture) and birds (e.g., chicken and fowl).

Higher doses of a nicotinamide riboside ester and carbonate preparation or composition of the invention that increase the level of NAD and/or the activity of a sirtuin protein may also be used as a pesticide by interfering with the regulation of silenced genes and the regulation of apoptosis during development. In this embodiment, a nicotinamide riboside ester and carbonate preparation or composition of the invention may be applied to plants using a method known in the art that ensures the compound is bio-available to insect larvae, and not to plants.

At least in view of the link between reproduction and longevity (Longo and Finch, Science, 2002), nicotinamide riboside ester and carbonate preparations and compositions of the invention that increase the level of NAD and/or the activity of a sirtuin protein can be applied to affect the reproduction of organisms such as insects, animals and microorganisms.

EXEMPLIFICATION

The invention now being generally described, it will be more readily understood by reference to the following examples which are included merely for purposes of illustration of certain aspects and embodiments of the present invention, and are not intended to limit the invention in any way.

Example 1

Synthesis of NRH Triacetate

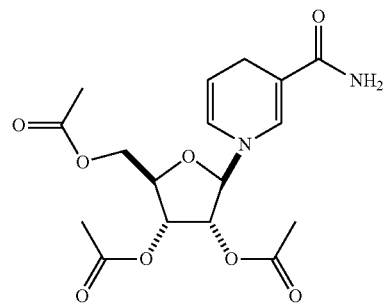 [SMILES: CC(=O)OC[C@H]1O[C@@H](N2C=CCC(C(N)=O)=C2)[C@H](OC(C)=O)[C@@H]1OC(C)=O]

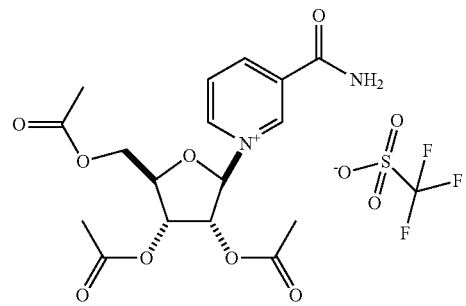

Step 1. 3-carbamoyl-1-((2R,3R,4R,5R)-3,4-diacetoxy-5-(acetoxymethyl)tetrahydrofuran-2-yl)pyridin-1-ium trifluoromethanesulfonate (NR Triacetate Triflate). To a suspension of 27.98 g (229 mmol) of nicotinamide in 350 mL of $CH_3CN$ at ambient temperature was added 73 mL (403 mmol) of trimethylsilyl trifluoromethanesulfonate (TM-SOTf), in one portion. The nicotinamide dissolved completely within 5 min. A solution of α/β-D-ribofuranose-1,2,3,5-tetra-O-acetate 24.31 g (76.39 mmol) in 30 mL of $CH_3CN$ was prepared separately, then added to the nicotinamide solution, all in one portion. The last traces of the ribose ester were taken up in 10 mL of $CH_3CN$, and this was also added to the reaction. The solution was stirred at ambient temperature for 30 min, then the excess TMSOTf was quenched by the addition of 1 mL of 1.2 M $NaHCO_{3(aq.)}$, followed by 20 g of solid $NaHCO_3$, in small portions, to control the evolution of $CO_2$. The suspension was stirred at ambient temperature for 30 min, then concentrated in vacuo to a thick, yellow paste. This was suspended in 30 mL of methanol, ensuring that the mixture was of a uniform consistency, then 300 mL of $CH_2Cl_2$ was added. This suspension was stirred for 15 min, then the solids were filtered and washed with 100 mL of $CH_2Cl_2$. The yellow filtrate was concentrated in vacuo to a bright yellow thick oil which was used without further purification in the next step. MS (ESI) (electrospray ionization mass spectrometry (also, ESI-MS)) calcd for $C_{17}H_{21}N_2O_8$: 381.1; found: 381.2 (M)⁺.

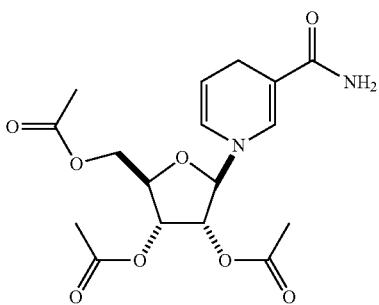

Step 2. (2R,3R,4R,5R)-2-(acetoxymethyl)-5-(3-carbamoylpyridin-1(4H)-yl)tetrahydrofuran-3,4-diyl diacetate (NRH-triacetate). To a flask containing crude NR triacetate triflate from the above procedure was added 250 mL of 1.2 M NaHCO$_{3(aq.)}$. The mixture was stirred at ambient temperature under N$_2$ until all of the thick, yellow, oily starting material had dissolved. To this solution was added 26.64 g (153.0 mmol) of sodium dithionite, in small portions to control the evolution of gas. After all of the Na$_2$S$_2$O$_4$ had been added, the yellow solution was stirred under N$_2$ at ambient temperature. After 5 h, the opaque mixture was extracted with CH$_2$Cl$_2$ (3×130 mL). The combined CH$_2$Cl$_2$ layers were back extracted with water (3×100 mL), then brine (1×100 mL), dried over MgSO$_4$, filtered, and concentrated in vacuo to 23.62 g (81%, 2 steps) of a yellow foam. If desired, the product could be purified via silica gel chromatography, eluting with 95:5 CH$_2$Cl$_2$: MeOH to give a yellow foam. MS (ESI) calcd for C$_{17}$H$_{22}$N$_2$O$_8$: 382.1; found: 383.2 (M+H)$^+$.

Example 2

Synthesis of NRH Tripropionate

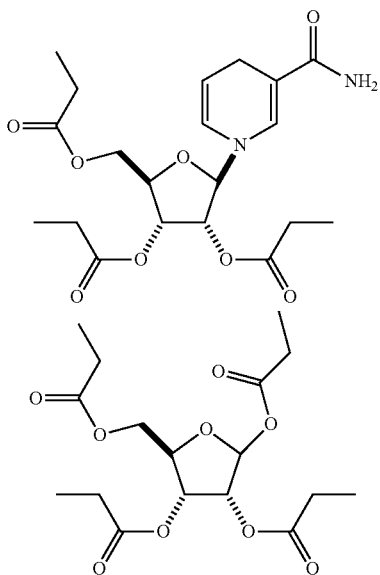

Step 1. α/β-D-Ribofuranose-1,2,3,5-tetra-O-propionate. To 1.11 g (6.76 mmol) of 1-O-methyl-α/β-D-ribofuranose was added 20 mL (150 mmol) of propionic anhydride, and 1.0 mL (13 mmol) of propionic acid. The mixture was stirred and heated at 100° C. for 1.5 h, then it was stored at −20° C. overnight (18 h). In the morning, the reaction mixture was warmed to 25° C., then 0.2 mL of H$_2$SO$_4$ was added, and the reaction was stirred at ambient temperature for 2 h. The solution was poured into 100 mL of cold 1.2 M NaHCO$_3$ solution, and the mixture was extracted with CH$_2$Cl$_2$ (2×100 mL). The combined CH$_2$Cl$_2$ layers were back extracted with 1.2 M NaHCO$_{3(aq.)}$ (1×100 mL) and brine (1×100 mL), filtering if necessary to break any emulsions. The organic layer was dried over Na$_2$SO$_4$, filtered, and concentrated in vacuo. The residue was purified via silica gel chromatography (40 g column), eluting with 40 mL pentane, a gradient of 0 to 10% ethyl acetate:pentane over 120 mL, 120 mL of 10% ethyl acetate:pentane, a gradient of 10 to 25% ethyl acetate:pentane over 120 mL, 120 mL of 25% ethyl acetate:pentane, then a gradient of 25 to 50% ethyl acetate:pentane over 120 mL. The product was in the 25% ethyl acetate:pentane fractions. (TLC 25% ethyl acetate:pentane, stained with phosphomolybdic acid, both anomers visible). The product containing fractions (both anomers) were concentrated in vacuo to give 2.01 g (79%) of a colorless oil. MS (ESI) calcd for C$_{17}$H$_{26}$O$_9$: 374.2; found: 301.2 (M-C$_3$H$_5$O$_2$)$^+$.

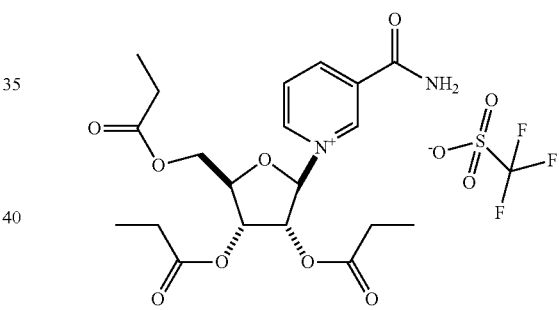

Step 2. 1-((2R,3R,4R,5R)-3,4-bis(propionyloxy)-5-((propionyloxy)methyl)tetrahydrofuran-2-yl)-3-carbamoylpyridin-1-ium trifluoromethanesulfonate. To a suspension of 1.97 g (16.1 mmol) of nicotinamide in 30 mL of CH$_3$CN was added 5.3 mL (29.5 mmol) of TMSOTf. The mixture was stirred at ambient temperature until all of the nicotinamide had dissolved, then a solution of 2.01 g (5.37 mmol) of α/β-D-Ribofuranose-1,2,3,5-tetra-O-propionate in 5 mL of CH$_3$CN was added. The reaction was stirred at ambient temperature for 30 min, then 0.2 mL of 1.2 M NaHCO$_{3(aq.)}$ was added, followed by 1.64 g of NaHCO$_3$. The reaction was stirred at ambient temperature for 15 min, then the solids were filtered and washed with CH$_3$CN. The combined filtrate and washings was concentrated in vacuo. The residue was taken up in 20 mL of CH$_2$Cl$_2$, then the insoluble salts were filtered, and washed with CH$_2$Cl$_2$. The combined filtrate and washings was concentrated to a yellow residue which was used without further purification. MS (ESI) calcd for C$_{20}$H$_{27}$N$_2$O$_8$: 423.2; found: 423.2 (M)$^+$.

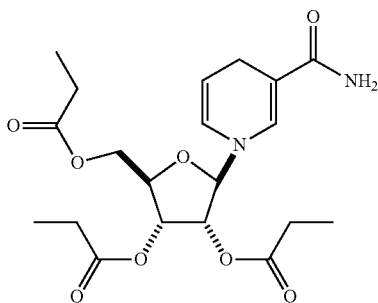 [SMILES: CCC(=O)OC[C@H]1O[C@@H](N2C=CCC(C(N)=O)=C2)[C@H](OC(=O)CC)[C@@H]1OC(=O)CC]

Step 3. (2R,3R,4R,5R)-2-(3-carbamoylpyridin-1(4H)-yl)-5-((propionyloxy)methyl) tetrahydrofuran-3,4-diyl dipropionate. To the yellow residue from step 2 was added 20 mL of CH$_2$Cl$_2$, and 20 mL of 1.2 M NaHCO$_{3(aq.)}$. To the stirred biphasic mixture was added 3.2 g (18 mmol) of sodium dithionite, and 5 g of NaHCO$_3$. The reaction was stirred under N$_2$ at ambient temperature for 18 h. The reaction was diluted with 30 mL of CH$_2$Cl$_2$ and 30 mL of H$_2$O, the layers were stirred, then separated. The aqueous layer was extracted with additional CH$_2$Cl$_2$ (1×50 mL), then the combined organic layers were extracted with 1.2 M NaHCO$_{3(aq.)}$ (1×50 mL), and brine (1×50 mL), dried over Na$_2$SO$_4$, filtered, and concentrated in vacuo. The residue was purified via silica gel chromatography, (40 g column), eluting with 40 mL of pentane, then a gradient of 100% pentane to 100% ethyl acetate over 200 mL, and finally 400 mL of ethyl acetate. The product was recovered from the ethyl acetate fractions. The solvent was removed in vacuo, the residue was taken up in CH$_3$CN and concentrated to remove the rest of the ethyl acetate, then the product was dissolved in water with enough CH$_3$CN to ensure dissolution. The mixture was frozen and lyophilized to give 1.27 g (56%) of a yellow powder. MS (ESI) calcd for C$_{20}$H$_{28}$N$_2$O$_8$: 424.2; found: 425.2 (M+H)$^+$.

Example 3

Synthesis of NRH Tri-n-butyrate

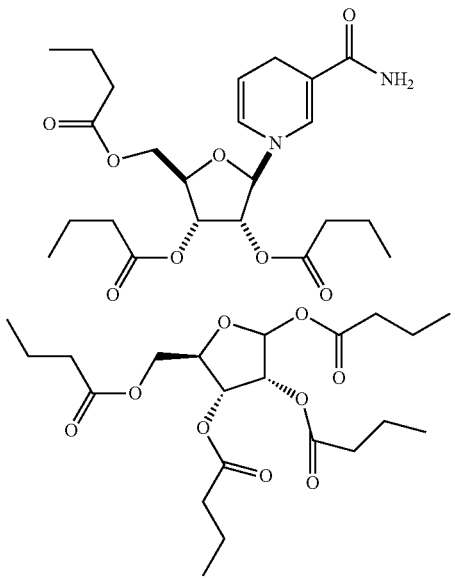

Step 1. α/β-D-Ribofuranose-1,2,3,5-tetra-O-n-butyrate. To 1.00 g (6.09 mmol) of 1-O-methyl-α/β-D-ribofuranose was added 20 mL (120 mmol) of butyric anhydride, and 1.0 mL (11 mmol) of butyric acid. The stirred reaction was heated at 100° C. for 1.5 h, then cooled to ambient temperature. Next, 0.30 mL (5.6 mmol) of 98% H$_2$SO$_4$ was added, then the reaction was stirred at ambient temperature for 1 h. LCMS (also, LC-MS or Liquid Chromatography Mass Spectrometry) indicated that the reaction was complete after this time. The solution was poured into 100 mL of cold 1.2 M NaHCO$_3$ solution, and the mixture was extracted with CH$_2$Cl$_2$ (2×100 mL). The combined CH$_2$Cl$_2$ layers were back extracted with 1.2 M NaHCO$_{3(aq.)}$ (1×100 mL) and brine (1×100 mL), filtering if necessary to break any emulsions. The organic layer was dried over Na$_2$SO$_4$, filtered, and concentrated in vacuo. The residue was purified via silica gel chromatography (40 g column), eluting with 40 mL of pentane, then 0 to 10% ethyl acetate in pentane over 120 mL, 120 mL of 10% ethyl acetate in pentane. The α and β anomers separated and were recovered from the 10% ethyl acetate fractions. They were combined for use in the next step. Concentration of the product containing fractions gave 2.04 g (78%) of a clear, colorless oil. TLC (10% ethyl acetate: 90% pentane, stain with phosphomolybdic acid). MS (ESI) calcd for C$_{21}$H$_{34}$O$_9$: 430.2; found: 343.2 (M-C$_4$H$_7$O$_2$)$^+$, 453.3 (M+Na)$^+$.

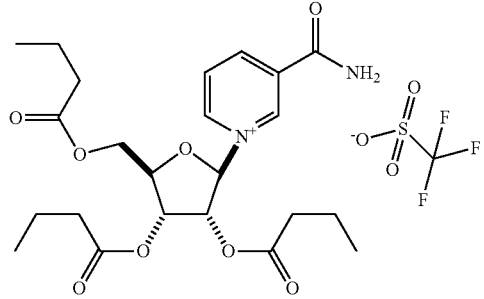

Step 2. 1-((2R,3R,4R,5R)-3,4-bis(butyryloxy)-5-((butyryloxy)methyl)tetrahydrofuran-2-yl)-3-carbamoylpyridin-1-ium trifluoromethanesulfonate (NR tributyrate triflate). To a suspension of 1.64 g (13.5 mmol) of nicotinamide in 30 mL of CH$_3$CN was added 4.46 mL (25 mmol) of trimethylsilyl trifluoromethanesulfonate. The suspension was stirred at ambient temperature until all of the nicotinamide had dissolved, then a solution of 1.93 g (4.48 mmol) of α/β-D-Ribofuranose-1,2,3,5-tetra-O-n-butyrate in 5 mL of CH$_3$CN was added. The reaction was stirred at ambient temperature for 30 min, then 0.2 mL of 1.2 M NaHCO$_{3(aq.)}$ was added, followed by 1.64 g (19.5 mmol) of NaHCO$_3$. The suspension was stirred for 15 min, then the solids were filtered and washed with CH$_3$CN. The combined filtrate and washings solution was concentrated to about 8 mL residual volume, then 40 mL of CH$_2$Cl$_2$ was added. The precipitate was filtered and washed with additional CH$_2$Cl$_2$, then the combined filtrate and washings solution was concentrated in vacuo to a yellow oil. This was used without further purification in the next step. MS (ESI) calcd for C$_{23}$H$_{33}$N$_2$O$_8$: 465.2; found: 465.3 (M)$^+$.

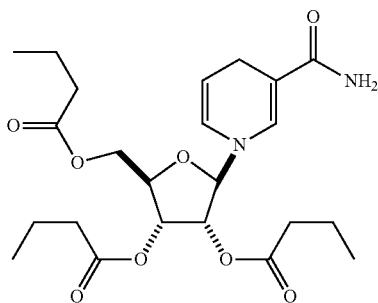 [SMILES: CCCC(=O)OC[C@H]1O[C@@H](N2C=CCC(C(N)=O)=C2)[C@H](OC(=O)CCC)[C@@H]1OC(=O)CCC]

Step 3. (2R,3R,4R,5R)-2-((butyryloxy)methyl)-5-(3-carbamoylpyridin-1(4H)-yl)tetrahydrofuran-3,4-diyl dibutyrate (NRH-tri-n-butyrate). To the crude product from step 2 was added 20 mL of 1.2 M NaHCO$_{3(aq.)}$, and 20 mL of CH$_2$Cl$_2$. To the biphasic mixture was added 3.18 g (18.2 mmol) of sodium dithionite, then 2.0 g (24 mmol) of NaHCO$_3$. The reaction was stirred under N$_2$ and at ambient temperature for 18 h. The layers were separated, then the aqueous layer was extracted with CH$_2$Cl$_2$ (1×20 mL). The combined CH$_2$Cl$_2$ layers were extracted with 1.2 M NaHCO$_{3(aq.)}$, then brine, dried over Na$_2$SO$_4$, filtered, and concentrated in vacuo to an oil. The product was purified via silica gel chromatography, (40 g column), eluting with 40 mL of pentane, then a 120 mL gradient of 0 to 100% pentane in ethyl acetate, and finally 240 mL of ethyl acetate. The ethyl acetate fractions contained the product. The product containing fractions were combined and concentrated in vacuo to give an oil. This was taken up in CH$_3$CN and evaporated to remove the ethyl acetate. The residue was taken up in water and CH$_3$CN was added to give a solution. The solution was frozen and lyophilized to give 1.23 g (59%) of the product as an orange oil. MS (ESI) calcd for C$_{23}$H$_{34}$N$_2$O$_8$: 466.2; found: 467.3 (M)$^+$.

Example 4

Synthesis of NRH-triisobutyrate

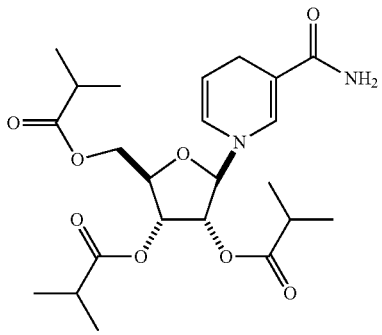

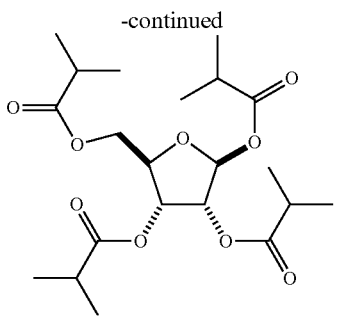

(2R,3R,4R,5R)-2-(3-carbamoylpyridin-1 (4H)-yl)-5-((isobutyryloxy)methyl)tetrahydrofuran-3,4-diyl bis(2-methylpropanoate) (NRH-triisobutyrate)

Step 1. α/β-D-Ribofuranose-1,2,3,5-tetra-O-isobutyrate. To 1.24 g (6.09 mmol) of 1-O-methyl-α/β-D-ribofuranose was added 25 mL (150 mmol) of isobutyric anhydride, and 1.0 mL (11 mmol) of isobutyric acid. The reaction was heated at 100° C. for 2 h, then it was cooled to ambient temperature. Next, 0.3 mL (5.6 mmol) of 98% H$_2$SO$_4$ was added, and the solution was stirred at ambient temperature for 2 h. The reaction was complete after this time as determined by $^1$H NMR spectroscopy on an aliquot. The entire mixture was poured into 50 mL of ice-cold 1.2 M NaHCO$_{3(aq.)}$, the mixture extracted with CH$_2$Cl$_2$ (2×50 mL), then the combined CH$_2$Cl$_2$ layers were back extracted with H$_2$O. The extractions were filtered as necessary to break any emulsions. The organic layer was dried over Na$_2$SO$_4$, filtered, and concentrated in vacuo to an oil. This was purified via silica gel chromatography (80 g column), eluting with 80 mL of pentane, 240 mL of a 0% to 10% ethyl acetate in pentane gradient, 240 mL of a 10% to 25% ethyl acetate in pentane gradient and 240 mL of 25% ethyl acetate in pentane. The product containing fractions were identified by TLC (10% ethyl acetate/pentane), pooled, and concentrated to an oil. The α and β anomers were not kept separate, and were pooled together to give an anomeric product mixture. To remove the last traces of isobutyric acid, the oily product mixture was taken up in ethyl acetate, then extracted with 1.2 M NaHCO$_{3(aq.)}$, and brine. The organic layer was dried over Na$_2$SO$_4$, filtered, and concentrated in vacuo to an oil. This was dried under high vacuum (<1 mm Hg, ambient temperature) for 3 days, to give 2.40 g (74%) of the product as a very pale yellow oil.

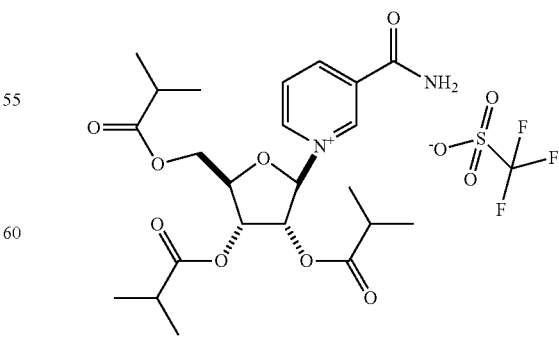

Step 2. 1-((2R,3R,4R,5R)-3,4-bis(isobutyryloxy)-5-((isobutyryloxy)methyl)tetrahydrofuran-2-yl)-3-carbamoylpyridin-1-ium trifluoromethanesulfonate (NR triisobutyrate triflate). To a suspension of 2.04 g (16.73 mmol) of nicotinamide in 50 mL of CH$_3$CN was added 5.55 mL (30.7 mmol) of trimethylsilyl trifluoromethanesulfonate. The mixture was stirred until all of the nicotinamide had dissolved, then a solution of 2.40 g (5.58 mmol) of α/β-D-Ribofuranose-1,2,3,5-tetra-O-isobutyrate in 10 mL of CH$_3$CN was added to the reaction. The last traces of the ribose ester were rinsed in with an additional 5 mL of CH$_3$CN. The mixture was stirred at ambient temperature for 30 min, then the reaction was quenched by the addition of 0.2 mL of 1.2 M NaHCO$_3$ and 1.64 g (19.5 mmol) of NaHCO$_3$. The suspension was stirred for 15 min, then the solids were filtered and washed with 5 mL of CH$_3$CN. The filtrate and washings solution was concentrated in vacuo, then the residue was taken up in 50 mL of CH$_2$Cl$_2$. The solids were filtered and washed with 10 mL of CH$_2$Cl$_2$, then the combined filtrate and washings solution was concentrated in vacuo to a yellow oil. This was used without further purification in the next reaction. MS (ESI) calcd for C$_{23}$H$_{33}$N$_2$O$_8$: 465.2; found: 465.3 (M)$^+$.

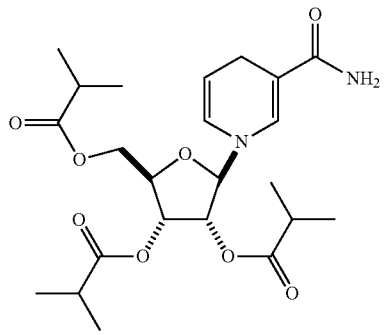 [SMILES: CC(C)C(=O)OC[C@H]1O[C@@H](N2C=CCC(C(N)=O)=C2)[C@H](OC(=O)C(C)C)[C@@H]1OC(=O)C(C)C]

Step 3. (2R,3R,4R,5R)-2-(3-carbamoylpyridin-1(4H)-yl)-5-((isobutyryloxy)methyl)-tetrahydrofuran-3,4-diyl bis(2-methylpropanoate) (NRH triisobutyrate). To a solution of the crude product from step 2 in 20 mL of CH$_2$Cl$_2$ was added 20 mL of 1.2 M NaHCO$_3$, then 2.91 g (16.7 mmol) of sodium dithionite, and 5.0 g (60 mmol) of NaHCO$_3$. The reaction was stirred at ambient temperature under N$_2$ for 18 h, then the layers were separated. The aqueous layer was extracted with additional CH$_2$Cl$_2$ (1×20 mL), then the combined organic layers were back extracted with 1.2 M NaHCO$_3$ (1×20 mL), and brine (1×20 mL), dried over Na$_2$SO$_4$, filtered, and concentrated in vacuo. The product was purified via silica gel chromatography (80 g column), eluting with 80 mL of pentane, 400 mL of 0% to 100% ethyl acetate in pentane, and finally 800 mL of ethyl acetate. The product eluted in the 100% ethyl acetate fractions. The product containing fractions were concentrated to an oil. This was taken up in CH$_3$CN, then concentrated to remove the ethyl acetate. The residue was taken up in a minimal amount of CH$_3$CN, then water was added until the solution was saturated with the product. The solution was frozen and lyophilized to give 1.50 g (58%, 2 steps) of the product as a yellow foam. MS (ESI) calcd for C$_{23}$H$_{34}$N$_2$O$_8$: 466.2; found: 467.3 (M)$^+$.

Example 5

Synthesis of NRH Tribenzoate

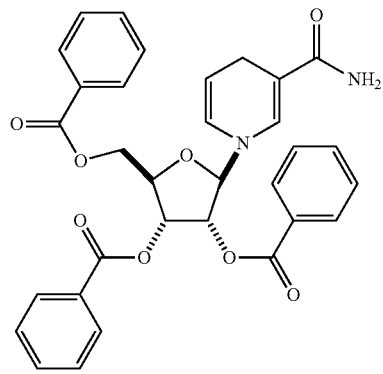 [SMILES: NC(=O)C1=CN([C@@H]2O[C@H](COC(=O)c3ccccc3)[C@@H](OC(=O)c3ccccc3)[C@H]2OC(=O)c2ccccc2)C=CC1]

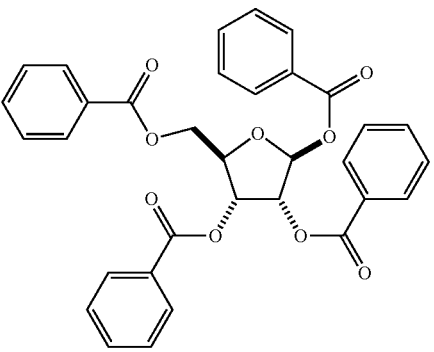 [SMILES: O=C(OC[C@H]1O[C@@H](OC(=O)c2ccccc2)[C@H](OC(=O)c2ccccc2)[C@@H]1OC(=O)c1ccccc1)c1ccccc1]

(2R,3R,4R,5R)-2-((benzoyloxy)methyl)-5-(3-carbamoylpyridin-1 (4H)-yl)tetrahydrofuran-3,4-diyl dibenzoate (NRH tribenzoate)

Step 1. α/β-D-Ribofuranose-1,2,3,5-tetra-O-benzoate. To 2.11 g (12.85 mmol) of 1-O-methyl-α/β-D-ribofuranose was added 58 g (257 mmol) of benzoic anhydride. The reaction was stirred and heated at 100° C., which melted the anhydride and slowly dissolved the starting material. After 1.5 h, the reaction was cooled to ambient temperature, but it still remained liquid. To the solution was added 0.30 mL (5.6 mmol) of 98% H$_2$SO$_4$, then the reaction was stirred at ambient temperature for 18 h. During this time, the reaction solidified. The solid mixture was dissolved in 100 mL of CH$_2$Cl$_2$, then extracted with 1.2 M NaHCO$_3$ (1×100 mL). The aqueous layer was back extracted with CH$_2$Cl$_2$ (1×100 mL), then the combined organic layers were washed with 1.2 M NaHCO$_3$ (1×100 mL), and brine (1×100 mL), and concentrated in vacuo. The crude mixture was purified via silica gel chromatography (220 g column), eluting with 220 mL of pentane, then 660 mL of a gradient of 0% to 10% ethyl acetate in pentane, 660 mL of ethyl acetate, then 660 mL of a gradient of 10% to 25% ethyl acetate in pentane, and 660 mL of 25% ethyl acetate in pentane. The product eluted in 25% ethyl acetate:pentane. Some product also eluted at the solvent front, along with benzoic anhydride. The product-benzoic anhydride mixture was purified via a second silica gel column, then all of the product containing fractions were combined and concentrated. Another silica gel column (80 g) was run using the same elution sequence, to give 3.54 g (49%) of the product as a colorless oil.

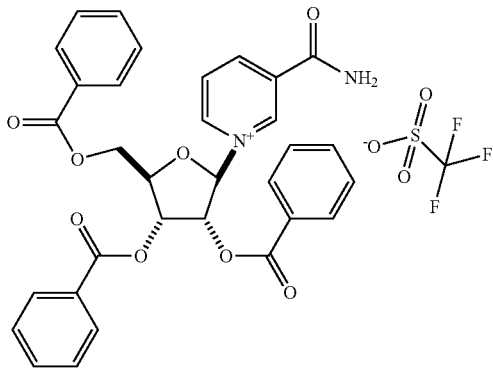

Step 2. 1-((2R,3R,4R,5R)-3,4-bis(benzoyloxy)-5-((benzoyloxy)methyl)tetrahydrofuran-2-yl)-3-carbamoylpyridin-1-ium trifluoromethanesulfonate (NR tribenzoate triflate). To a suspension of 2.29 g (18.8 mmol) of nicotinamide in 50 mL of $CH_3CN$ was added 6.2 mL (34 mmol) of trimethylsilyltrifluoromethanesulfonate. The reaction was stirred at ambient temperature until all of the nicotinamide had dissolved, then a solution of 3.54 g (6.25 mmol) of α/β-D-ribofuranose-1,2,3,5-tetra-O-benzoate in 10 mL of $CH_3CN$ was added. The last traces of the ribose ester were rinsed in with 5 mL of $CH_3CN$. The reaction was stirred at ambient temperature for 30 min, then 0.2 mL of 1.2 M $NaHCO_{3(aq.)}$ was added, followed by 1.64 g (19.5 mmol) of $NaHCO_3$. The suspension was stirred at ambient temperature for 15 min, then the solids were filtered and washed with 10 mL of $CH_3CN$. The combined filtrate and washings solution was concentrated in vacuo to a yellow residue. This was taken up in 50 mL of $CH_2Cl_2$ and filtered. The precipitate was washed with 10 mL of $CH_2Cl_2$, then the combined filtrate and washings solution was concentrated in vacuo to a yellow residue. MS (ESI) calcd for $C_{32}H_{27}N_2O_8$: 567.2; found: 567.3 $(M)^+$.

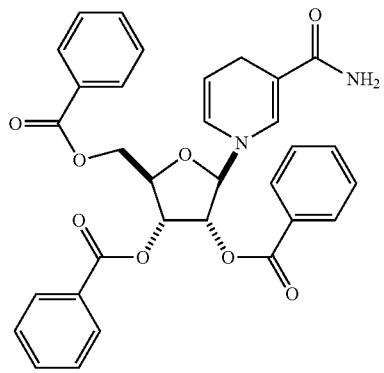 [SMILES: NC(=O)C1=CN([C@@H]2O[C@H](COC(=O)c3ccccc3)[C@@H](OC(=O)c3ccccc3)[C@H]2OC(=O)c2ccccc2)C=CC1]

Step 3. (2R,3R,4R,5R)-2-((benzoyloxy)methyl)-5-(3-carbamoylpyridin-1(4H)-yl)tetrahydrofuran-3,4-diyl dibenzoate (NRH tribenzoate). The product from step 2 was taken up in 20 mL of $CH_2Cl_2$, then 20 mL of 1.2 M $NaHCO_3$ was added, followed by 3.26 g (19 mmol) of sodium dithionite, and 5.0 g (60 mmol) of $NaHCO_3$. The reaction was stirred at ambient temperature under $N_2$ for 18 h. The layers were separated, then the organic layer was washed with 1.2 M $NaHCO_{3(aq.)}$ (1×20 mL), and brine (1×20 mL), dried over $Na_2SO_4$, filtered, and concentrated to an oil. The product was purified via silica gel chromatography (80 g column), eluting with 80 mL of pentane, then 240 mL of a gradient of 0 to 50% ethyl acetate in pentane, 240 mL of 50% ethyl acetate in pentane, then 240 mL of a gradient of 50 to 100% ethyl acetate in pentane, and finally 640 mL of 100% ethyl acetate. The ethyl acetate fractions contained the product. This was concentrated to 3.2 g of a waxy residue. A second 40 g silica gel column, eluting with 40 mL of pentane, 200 mL of 0 to 100% ethyl acetate in pentane, and finally 400 mL of ethyl acetate gave the product in the ethyl acetate fractions. The product containing fractions were concentrated in vacuo, then the residue was taken up in water with enough $CH_3CN$ to give a solution. The solution was frozen and lyophilized to give 1.72 g (48%) of a yellow solid. MS (ESI) calcd for $C_{32}H_{28}N_2O_8$: 568.2; found: 569.3 $(M+H)^+$.

Example 6

Synthesis of NRH Triethylcarbonate

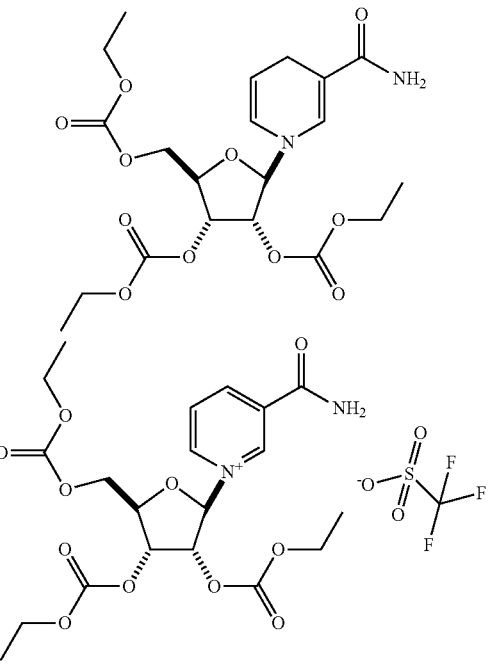

((2R,3R,4R,5R)-5-(3-carbamoylpyridin-1(4H)-yl)-3,4-bis((ethoxycarbonyl)oxy)-tetrahydrofuran-2-yl) methyl ethylcarbonate (NRH triethylcarbonate)

Step 1. 1-((2R,3R,4R,5R)-3,4-bis((ethoxycarbonyl)oxy)-5-(((ethoxycarbonyl)oxy)-methyl)tetrahydrofuran-2-yl)-3-carbamoylpyridin-1-ium trifluoromethanesulfonate (NR triethylcarbonate triflate). To a solution of nicotinamide riboside (NR) chloride in 12 mL of DMF was added 5.0 mL (62 mmol) of pyridine. The mixture was cooled with an ice bath, then 3.95 mL (41.3 mmol) of ethyl chloroformate was added, dropwise, with stirring. The ice bath was removed, and the reaction was stirred at ambient temperature for 18 h. An additional 2.5 mL (31 mmol) of pyridine was added, then the reaction was cooled with an ice bath. Another 2.0 mL (21 mmol) of ethyl chloroformate was added, dropwise, then the ice bath was removed. The reaction was stirred at ambient temperature for an additional 4 h, then 5 mL of methanol was added. The mixture was concentrated in vacuo until most of the DMF had evaporated. The residue was purified via silica gel chromatography (80 g column), eluting with $CH_2Cl_2$ (80 mL), then a gradient of 0 to 10% methanol in $CH_2Cl_2$ (240 mL), 240 mL of 10% methanol in $CH_2Cl_2$, 240 mL of 10 to 25% methanol in $CH_2Cl_2$, and finally 400 mL of 25% methanol in $CH_2Cl_2$. The product containing fractions were identified by LCMS, then pooled, and concentrated to an oil. The product mixture contained some pyridinium hydrochloride. The material was further purified with a second silica gel column (40 g column), using the same elution sequence as for the first column, but reducing the volumes by ½. The product still contained some pyridinium hydrochloride. MS (ESI) calcd for $C_{20}H_{27}N_2O_{11}$: 471.2; found: 471.2 $(M)^+$.

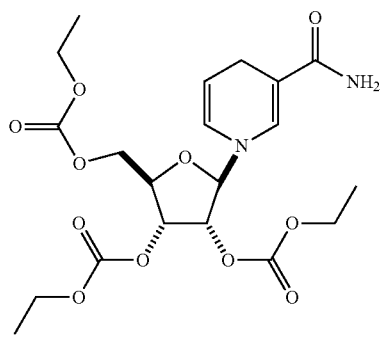 [SMILES: CCOC(=O)OC[C@H]1O[C@@H](N2C=CCC(C(N)=O)=C2)[C@H](OC(=O)OCC)[C@@H]1OC(=O)OCC]

Step 2. ((2R,3R,4R,5R)-5-(3-carbamoylpyridin-1(4H)-yl)-3,4-bis((ethoxycarbonyl)oxy)-tetrahydrofuran-2-yl) methyl ethylcarbonate (NRH triethylcarbonate). To the crude product from step 1 was added 25 mL of 1.2 M $NaHCO_{3(aq.)}$. The solution was concentrated in vacuo to remove traces of pyridine. The residue was taken up in 40 mL of 1.2 M $NaHCO_3$, then 40 mL of $CH_2Cl_2$ was added. Next, 3.6 g of sodium dithionite was added, then the mixture was stirred under $N_2$ for 72 h. The reaction was diluted with an additional 40 mL of water and 40 mL of $CH_2Cl_2$ to aid separation, then the layers were separated. The organic layer was back extracted with 1.2 M $NaHCO_{3(aq.)}$ (1×40 mL), and brine (1×40 mL), dried over $Na_2SO_4$, filtered, and concentrated. The residue was purified via silica gel chromatography (40 g column), eluting with 40 mL of pentane, then 120 mL of a gradient of 0 to 100% ethyl acetate, and finally 240 mL of ethyl acetate. The product was present in the ethyl acetate fractions. The product containing fractions were concentrated to a foam. This was dissolved in water, and $CH_3CN$ was added to give a solution. The solution was frozen, then lyophilized to give 413 mg (13%) of the product as a yellow solid. MS (ESI) calcd for $C_{20}H_{28}N_2O_{11}$: 472.2; found: 473.2 $(M)^+$.

Example 7

Synthesis of NRH Tripivalate

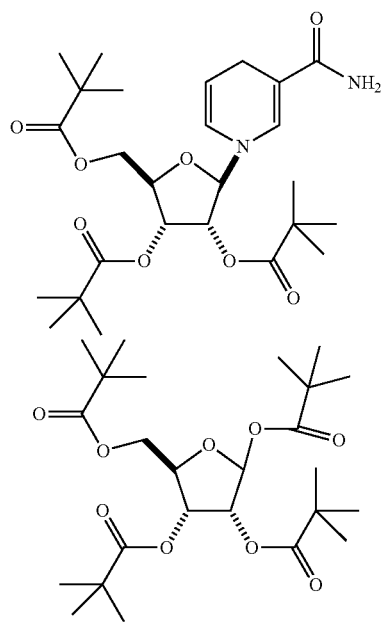

(2R,3R,4R,5R)-2-(3-carbamoylpyridin-1(4H)-yl)-5-((pivaloyloxy)methyl)tetrahydrofuran-3,4-diyl bis(2,2-dimethylpropanoate) (NRH tris(trimethyl)acetate; NRH tripivalate)

Step 1. α/β-D-Ribofuranose-1,2,3,5-tetra-O-trimethylacetate. To 4.97 g (30.3 mmol) of 1-O-methyl-α/β-D-ribofuranose was added 125 mL (606 mmol) of trimethylacetic anhydride. The mixture was stirred and heated at 100° C. for 2 h, then cooled to ambient temperature. Next, 1.0 mL (18 mmol) of 98% $H_2SO_4$ was added, then the reaction was stirred at ambient temperature for 72 h. The reaction mixture was poured into 150 mL of ice cold 1.2 M $NaHCO_{3(aq.)}$, and 150 mL of ethyl acetate was added. The mixture was stirred for 10 min, then the layers were separated. The organic layer was dried over $Na_2SO_4$, filtered, and concentrated in vacuo (50° C., <1 mm Hg) to remove most of the remaining trimethylacetic anhydride and trimethylacetic acid. The residue was purified via silica gel chromatography (220 g column), eluting with 220 mL of pentane, 660 mL of a gradient of 0 to 10% ethyl acetate in pentane, 1100 mL of 10% ethyl acetate in pentane. The product was present in the 10% ethyl acetate layers. The product containing fractions were pooled, then concentrated in vacuo to an oil that still contained some trimethylacetic acid. The oil was taken up in ethyl acetate (250 mL), then extracted with 1.2 M $NaHCO_{3(aq.)}$ (2×250 mL). The organic layer was dried over $Na_2SO_4$, filtered, and concentrated in vacuo to give 8.37 g (57%) of a nearly colorless oil.

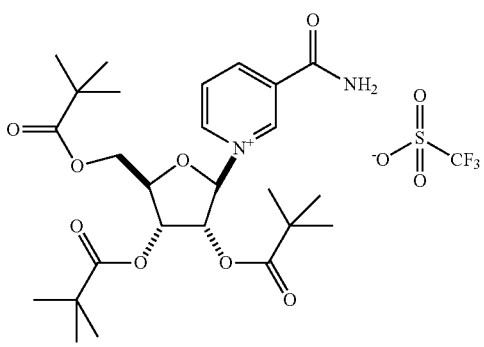

1-((2R,3R,4R,5R)-3,4-bis(pivaloyloxy)-5-((pivaloyloxy)methyl)tetrahydrofuran-2-yl)-3-carbamoylpyridin-1-ium trifluoromethanesulfonate. To a suspension of 4.60 g (37.7 mmol) of nicotinamide in 150 mL of $CH_3CN$ was added 12.5 mL (69.1 mmol) of trimethylsilyl trifluoromethanesulfonate. The mixture was stirred at ambient temperature until all of the nicotinamide had dissolved, then a solution of 6.11 g (12.6 mmol) of α/β-D-Ribofuranose-1,2,3,5-tetra-O-trimethylacetate in 40 mL of $CH_3CN$ was added. The last traces of the ribose ester were rinsed in with 10 mL of $CH_3CN$, then the reaction was stirred at ambient temperature for 72 h. Next, 1.0 mL of 1.2 M $NaHCO_{3(aq.)}$ was added, followed by 7.2 g (85.7 mmol) of $NaHCO_3$. The suspension was stirred at ambient temperature for 20 min, then the solvent was removed in vacuo. The residue was stirred with 50 mL of $CH_2Cl_2$, then the white precipitate was filtered and washed with an additional 10 mL of $CH_2Cl_2$. The combined filtrate and washings solution was concentrated in vacuo to a yellow residue. The product was purified via silica gel chromatography (220 g column), eluting with 220 mL of $CH_2Cl_2$, then a gradient of 660 mL 0 to 10% methanol in $CH_2Cl_2$, and 10% methanol in $CH_2Cl_2$. The product eluted at approximately 10% $CH_2Cl_2$. The product containing fractions were pooled, then concentrated in vacuo to give 6.34 g (77%) of a colorless foam. MS (ESI) calcd for $C_{26}H_{39}N_2O_8$: 507.3; found: 507.3 (M)+.

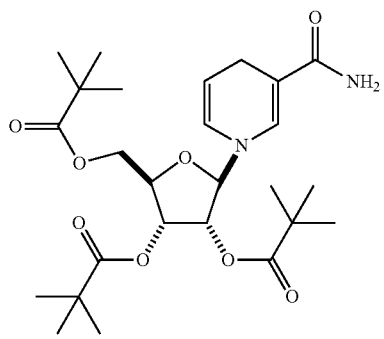

(2R,3R,4R,5R)-2-(3-carbamoylpyridin-1 (4H)-yl)-5-((pivaloyloxy)methyl)tetrahydrofuran-3,4-diyl bis(2,2-dimethylpropanoate) (NRH tris(trimethyl)acetate; NRH tripivalate). To a solution of 6.34 g (9.66 mmol) of the product from step 2 in 90 mL of $CH_2Cl_2$ was added 180 mL of 1.2 M $NaHCO_{3(aq.)}$, then 3.04 g (17.5 mmol) of sodium dithionite. The reaction was stirred at ambient temperature under $N_2$ for 18 h, then the layers were separated, and the aqueous layer was extracted with $CH_2Cl_2$ (1×90 mL). The combined organic layers were back extracted with 1.2 M $NaHCO_{3(aq.)}$ (1×90 mL), dried over $Na_2SO_4$, filtered, and concentrated in vacuo to an oil. This was purified via silica gel chromatography (220 g column), eluting with 220 mL of pentane, then 660 mL of a gradient of 0 to 100% ethyl acetate, and finally 2200 mL of ethyl acetate. The product eluted in 100% ethyl acetate. The product containing fractions were pooled, then concentrated in vacuo to an oily residue. Heptane was added, then removed in vacuo to give 2.87 g (45%) of a yellow foam. MS (ESI) calcd for $C_{26}H_{40}N_2O_8$: 508.3; found: 509.3 (M+H)+.

Example 8

Synthesis of NR-5'-O-n-butyrate

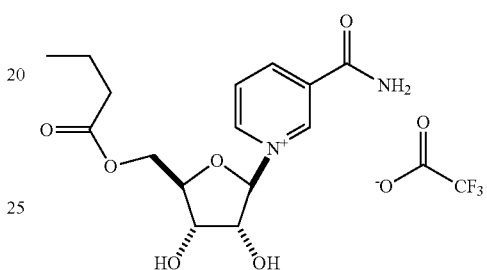

3-carbamoyl-1-((2R,3R,4S,5R)-3,4-dihydroxy-5-((propionyloxy)methyl)-tetrahydrofuran-2-yl)pyridin-1-ium 2,2,2-trifluoroacetate (NR-5-O-n-butyrate)

To a solution of 250 mg (0.82 mmol) of nicotinamide riboside in 5 mL of DMF was added 1.14 mL (12.0 mmol) of 2-chloropyridine, then 0.62 mL (6.00 mmol) of n-butyryl chloride. The reaction was stirred at ambient temperature for 30 min, then 2 mL of $CH_3OH$ was added to consume the excess acid chloride. The crude reaction was purified via reversed phase HPLC with the following elution sequence. Solvent A=0.1% TFA in $H_2O$, solvent B=$CH_3CN$; 100% A, 0% B for 1 min, 0 to 30% B over 7 min, 30 to 100% B over 7 min. The product eluted after approximately 7 min. The product containing fractions were concentrated in vacuo to give an oily residue. This was dissolved in water, frozen, and lyophilized to give 157 mg (42%) of a colorless semi-solid. MS (ESI) calcd for $C_{15}H_{21}N_2O_6$: 325.1; found: 325.2 (M)+.

Example 9

Synthesis of NR-5'-O-n-valerate

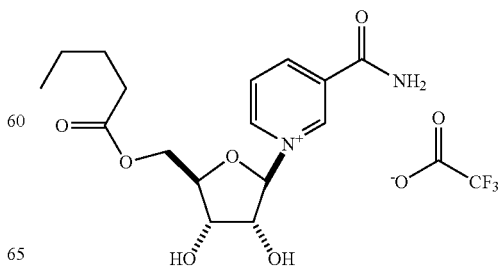

3-carbamoyl-1-((2R,3R,4S,5R)-3,4-dihydroxy-5-((pentanoyloxy)methyl)tetrahydrofuran-2-yl)pyridin-1-ium 2,2,2-trifluoroacetate. (NR-5-O-n-valerate)

To a solution of 250 mg (0.82 mmol) of nicotinamide riboside in 5 mL of DMF was added 1.14 mL (12.0 mmol) of 2-chloropyridine, then 0.71 mL (6.00 mmol) of n-pentanoyl chloride. The reaction was stirred at ambient temperature for 30 min, then 2 mL of $CH_3OH$ was added to consume the excess acid chloride. The crude reaction was purified via reversed phase HPLC with the following elution sequence. Solvent A=0.1% TFA in $H_2O$, solvent B=$CH_3CN$; 100% A, 0% B for 1 min, 0 to 30% B over 7 min, 30 to 100% B over 7 min. The product eluted after approximately 7 min. The product containing fractions were concentrated in vacuo to give an oily residue. This was dissolved in water, frozen, and lyophilized to give 173 mg (44%) of a colorless semi-solid. MS (ESI) calcd for $C_{16}H_{23}N_2O_6$: 339.2; found: 339.2 $(M)^+$.

Example 10

Synthesis of NR-5'-O-n-hexanoate

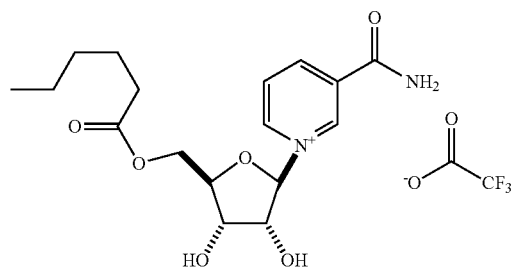

3-carbamoyl-1-((2R,3R,4S,5R)-5-((hexanoyloxy)methyl)-3,4-dihydroxytetrahydrofuran-2-yl)pyridin-1-ium 2,2,2-trifluoroacetate (NR-5-O-n-hexanoate)

To a solution of 250 mg (0.82 mmol) of nicotinamide riboside in 5 mL of DMF was added 1.14 mL (12.0 mmol) of 2-chloropyridine, then 0.84 mL (6.00 mmol) of n-hexanoyl chloride. The reaction was stirred at ambient temperature for 30 min, then 2 mL of $CH_3OH$ was added to consume the excess acid chloride. The reaction was stirred at ambient temperature for 15 min. The crude reaction was purified via reversed phase HPLC with the following elution sequence. Solvent A=0.1% TFA in $H_2O$, solvent B=$CH_3CN$; 100% A, 0% B for 1 min, 0 to 30% B over 7 min, 30 to 100% B over 7 min. The product eluted after approximately 7 min. The product containing fractions were concentrated in vacuo to give an oily residue containing some 2-chloropyridine. A second HPLC run over the same column, using a gradient of 100% A for 1 min, O to 30% B over 3 min, 30 to 100% B over 12 min. The pure product containing fractions were concentrated in vacuo to an oil. The impure product containing fractions were concentrated in vacuo, then the residue was repurified using the second HPLC elution sequence. The combined purified product was dissolved in water, frozen, and lyophilized to give 128 mg (44%) of a colorless semi-solid. MS (ESI) calcd for $C_{16}H_{23}N_2O_6$: 353.2; found: 353.2 $(M)^+$.

Example 11

Synthesis of NR-5'-O-n-decanoate

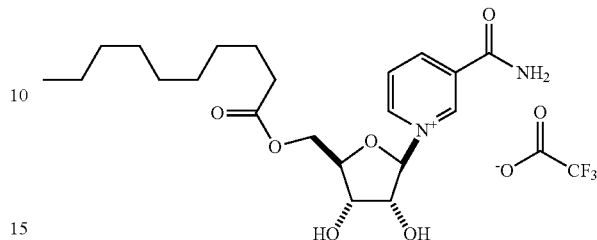

3-carbamoyl-1-((2R,3R,4S,5R)-5-((decanoyloxy)methyl)-3,4-dihydroxytetrahydrofuran-2-yl)pyridin-1-ium 2,2,2-trifluoroacetate (NR-5-O-n-decanoate)

To a solution of 250 mg (0.82 mmol) of nicotinamide riboside in 5 mL of DMF was added 1.14 mL (12.0 mmol) of 2-chloropyridine, then 1.25 mL (6.00 mmol) of n-decanoyl chloride. The reaction was stirred at ambient temperature for 30 min, then 2 mL of $CH_3OH$ was added to consume the excess acid chloride. The crude reaction was purified via reversed phase HPLC with the following elution sequence. Solvent A=0.1% TFA in $H_2O$, solvent B=$CH_3CN$; 100% A, 0% B for 1 min, 0 to 30% B over 3 min, 30 to 100% B over 5 min, 100% B for 5 min. The product containing fractions were concentrated in vacuo to give an oily residue. This was dissolved in water, frozen, and lyophilized to give 182 mg (41%) of a colorless waxy solid. MS (ESI) calcd for $C_{21}H_{33}N_2O_6$: 409.2; found: 409.2 $(M)^+$.

Example 12

Synthesis of NR-5'-O-myristoylate

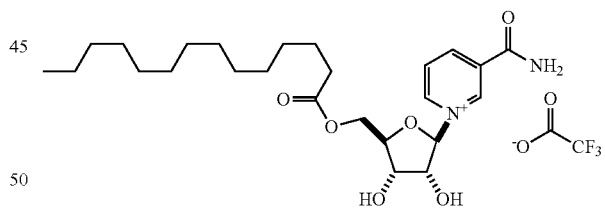

3-carbamoyl-1-((2R,3R,4S,5R)-3,4-dihydroxy-5-((tetradecanoyloxy)methyl)tetrahydrofuran-2-yl)pyridin-1-ium 2,2,2-trifluoroacetate (NR-5-O-myristoylate)

To a solution of 250 mg (0.82 mmol) of nicotinamide riboside in 5 mL of DMF was added 1.14 mL (12.0 mmol) of 2-chloropyridine, then 1.63 mL (6.00 mmol) of n-tetradecanoyl chloride. The reaction was stirred at ambient temperature for 30 min, then 2 mL of $CH_3OH$ was added to consume the excess acid chloride. The crude reaction was purified via reversed phase HPLC with the following elution sequence. Solvent A=0.1% TFA in $H_2O$, solvent B=0.1% TFA in $CH_3CN$; 100% A, 0% B for 1 min, 0 to 30% B over 2 min, 30 to 100% B over 7 min, 100% B for 5 min. The product eluted at approximately 9 min. The product containing fractions were concentrated in vacuo to give an oily residue. This was dissolved in water, frozen, and lyophilized to give 177 mg (36%) of a colorless waxy solid. MS (ESI) calcd for $C_{25}H_{41}N_2O_6$: 465.3; found: 465.3 (M)+.

Example 13

Synthesis of NR-5'-O-oleate

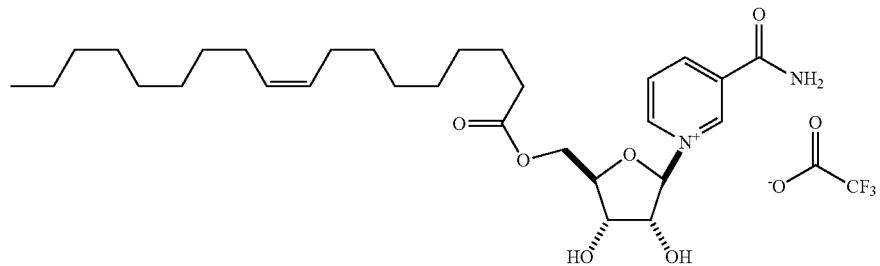

3-carbamoyl-1-((2R,3R,4S,5R)-3,4-dihydroxy-5-((oleoyloxy)methyl)tetrahydrofuran-2-yl)pyridin-1-ium 2,2,2-trifluoroacetate (NR-5-O-oleate)

To a solution of 250 mg (0.82 mmol) of nicotinamide riboside in 5 mL of DMF was added 1.14 mL (12.0 mmol) of 2-chloropyridine, then 1.98 mL (6.00 mmol) of oleoyl chloride. The reaction was stirred at ambient temperature for 30 min, then 2 mL of $CH_3OH$ was added to consume the excess acid chloride. The crude reaction was purified via reversed phase HPLC with the following elution sequence. Solvent A=0.1% TFA in $H_2O$, solvent B=0.1% TFA in $CH_3CN$; 100% A, 0% B for 1 min, 0 to 50% B over 3 min, 50 to 100% B over 5 min, 100% B for 6 min. The product eluted at about 7.5 min. The product containing fractions were concentrated in vacuo to give an oily residue. This was dissolved in water, frozen, and lyophilized to give 181 mg (33%) of a colorless waxy solid. MS (ESI) calcd for $C_{29}H_{47}N_2O_6$: 519.3; found: 519.4 (M)+.

Example 14

Synthesis of NRH-5'-O-myristoylate

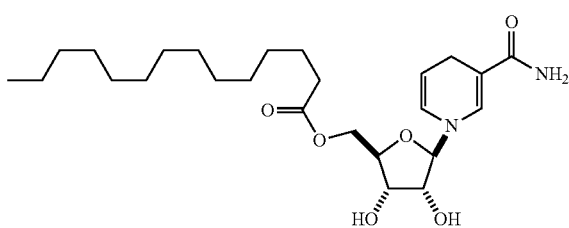

((2R,3S,4R,5R)-5-(3-carbamoylpyridin-1 (4H)-yl)-3,4-dihydroxytetrahydrofuran-2-yl)methyl tetradecanoate (NRH myristoylate)

To a solution of 177 mg (0.306 mmol) of 3-carbamoyl-1-((2R,3R,4S,5R)-3,4-dihydroxy-5-((tetradecanoyloxy) methyl)tetrahydrofuran-2-yl)pyridin-1-ium 2,2,2-trifluoroacetate (NR myristoylate trifluoroacetate) in 3 mL of $CH_2Cl_2$ and 3 mL of 1.2 M $NaHCO_3$ was added 160 mg of sodium dithionite. The reaction was stirred under $N_2$ for 18 h, then the reaction was diluted with 10 mL of $CH_2Cl_2$ and 10 mL of 1.2 M $NaHCO_3$. The layers were shaken and separated, then the aqueous layer was extracted with additional $CH_2Cl_2$ (1×10 mL). The combined organic layers were back extracted with brine, filtered to break an emulsion, dried over $MgSO_4$, filtered, and concentrated in vacuo. The residue was suspended in $H_2O$, then $CH_3CN$ was added to give a solution. The mixture was frozen and lyophilized to give 46 mg (32%) of the product as a light yellow solid. MS (ESI) calcd for $C_{25}H_{42}N_2O_6$: 466.3; found: 467.3 (M+H)+.

Example 15

Synthesis of NR-5'-O-propionate

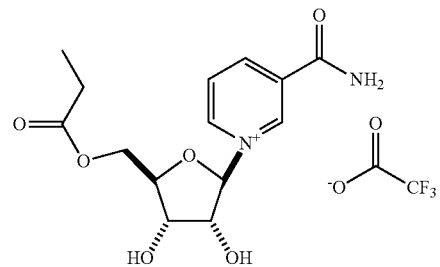

3-carbamoyl-1-((2R,3R,4S,5R)-3,4-dihydroxy-5-((propionyloxy)methyl)tetrahydrofuran-2-yl)pyridin-1-ium 2,2,2-trifluoroacetate. (NR-5-O-propionate)

To a solution of 250 mg (0.82 mmol) of nicotinamide riboside in 5 mL of DMF was added 1.14 mL (12.0 mmol) of 2-chloropyridine, then 0.52 mL (6.0 mmol) of propionyl chloride. The acid chloride was added dropwise. The mixture was stirred at ambient temperature for 30 min, then 2 mL of $CH_3OH$ was added, and the mixture was stored at −20° C. for 18 h. The crude reaction was purified via reversed phase HPLC with the following elution sequence. Solvent A=0.1% TFA in $H_2O$, solvent B=0.1% TFA in $CH_3CN$; 100% A, 0% B for 1 min, 0 to 30% B over 8 min, 30 to 100% B over 7 min. The product containing fractions were concentrated in vacuo to give an oily residue. This was dissolved in water, frozen, and lyophilized to give 58 mg (16%) of a colorless solid. MS (ESI) calcd for $C_{14}H_{19}N_2O_6$: 311.1; found: 311.1 (M)+.

Example 16

Synthesis of NR-5'-O-nonanoate

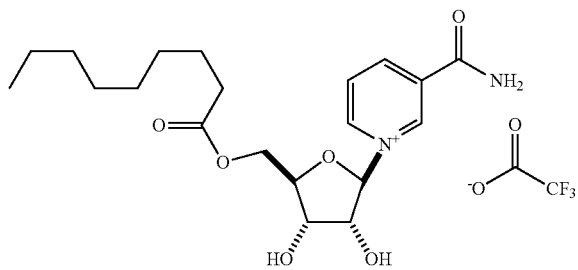

3-carbamoyl-1-((2R,3R,4S,5R)-3,4-dihydroxy-5-((nonanoyloxy)methyl)tetrahydrofuran-2-yl)pyridin-1-ium 2,2,2-trifluoroacetate (NR-5-O-nonanoate)

To a solution of 250 mg (0.82 mmol) of nicotinamide riboside in 5 mL of DMF was added 1.14 mL (12.0 mmol) of 2-chloropyridine, then 1.08 mL (6.0 mmol) of nonanoyl chloride. The mixture was stirred at ambient temperature for 30 min, then 2 mL of $CH_3OH$ was added to consume the remaining acid chloride. The crude reaction was purified via reversed phase HPLC with the following elution sequence. Solvent A=0.1% TFA in $H_2O$, solvent B=0.1% TFA in $CH_3CN$; 100% A, 0% B for 1 min, 0 to 50% B over 3 min, 50 to 100% B over 4 min, and 100% B for 8 min. The product containing fractions were concentrated in vacuo to give an oily residue. (Some fractions contained 2-chloropyridine, but this could be removed during the concentration in vacuo at 40° C. and <1 mm Hg). The residue was dissolved in water, frozen, and lyophilized to give 177 mg (40%) of a colorless solid. MS (ESI) calcd for $C_{20}H_{31}N_2O_6$: 395.2; found: 395.2 (M)$^+$.

Example 17

Synthesis of NR-tripentanoate

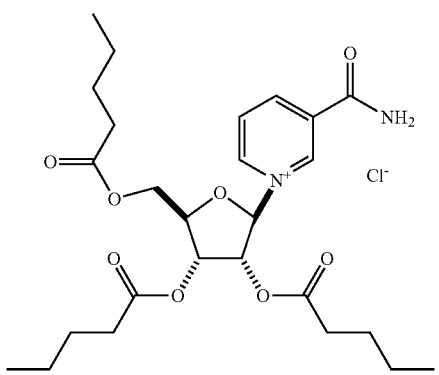

1-((2R,3R,4R,5R)-3,4-bis(pentanoyloxy)-5-((pentanoyloxy)methyl)tetrahydrofuran-2-yl)-3-carbamoylpyridin-1-ium chloride To a suspension of 500 mg (1.72 mmol) of nicotinamide riboside chloride in 30 mL of $CH_3CN$ was added 16 mg (0.14 mmol) of 4-(N,N-dimethylamino)pyridine, followed by 0.93 mL (4.72 mmol) of n-pentanoic anhydride. The reaction was stirred under $N_2$ for 18 h, then the solvent was removed in vacuo, leaving some anhydride in the product mixture. The residue was taken up in 30 mL of $H_2O$, and the suspension was extracted with heptanes (6×40 mL) to remove most of the remaining anhydride. The aqueous layer was concentrated in vacuo, then the residue was purified via silica gel chromatography, eluting with ethyl acetate. The product containing fractions were concentrated to 156 mg (17%) of a pale yellow foam. MS (ESI) calcd for $C_{26}H_{39}N_2O_8$: 507.3; found: 507.3 (M)$^+$. (RDC-529-49 on 3-28-2013 and 3-29-2013)

Example 18

Synthesis of NR-trihexanoate

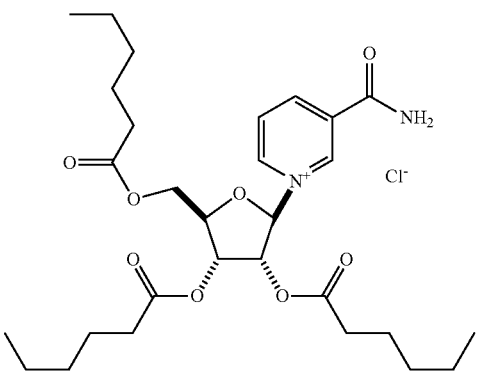

1-((2R,3R,4R,5R)-3,4-bis(pentanoyloxy)-5-((pentanoyloxy)methyl)tetrahydrofuran-2-yl)-3-carbamoylpyridin-1-ium chloride To a suspension of 400 mg (1.37 mmol) of nicotinamide riboside chloride in 30 mL of $CH_3CN$ was added 16 mg (0.14 mmol) of 4-(N,N-dimethylamino)pyridine, followed by 1.4 mL (6.19 mmol) of n-hexanoic anhydride. The reaction was stirred under $N_2$ for 18 h, then the solvent was removed in vacuo, leaving some anhydride in the product mixture. The residue was taken up in 30 mL of $H_2O$, and the suspension was extracted with heptanes (6×40 mL) to remove most of the remaining anhydride. The aqueous layer was concentrated in vacuo, then the residue was purified via silica gel chromatography, eluting with ethyl acetate. The product containing fractions were concentrated to 208 mg (26%) of a pale yellow foam. MS (ESI) calcd for $C_{29}H_{45}N_2O_8$: 549.3; found: 549.3 (M)$^+$.

Figure 3:
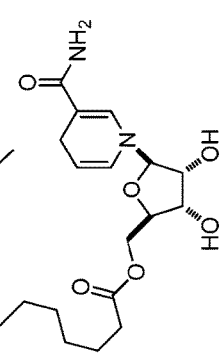
FIG. 3 summarizes exemplified compounds and their relative stability in plasma.
Figure 3:
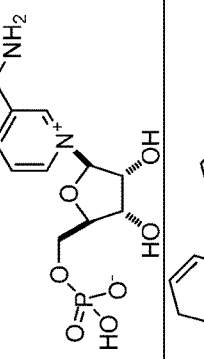
Figure 3:
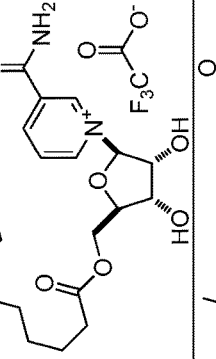
Figure 3:
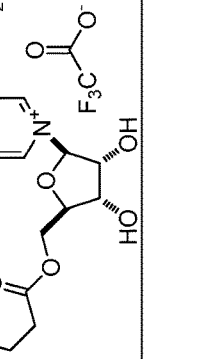
Figure 3:
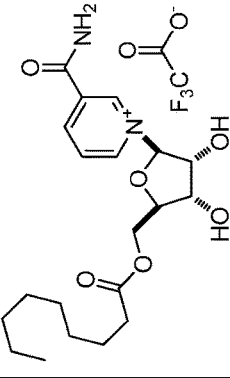
Figure 3:
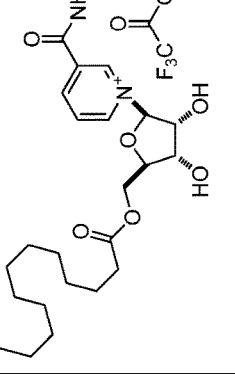
Figure 3:
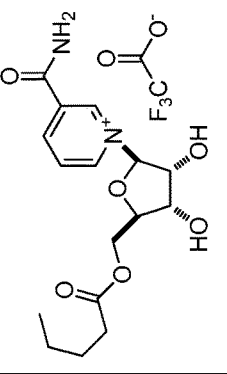
Figure 3:
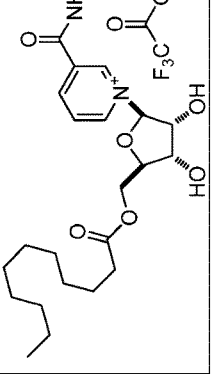

As shown in FIG. 3, the above exemplary compounds were analyzed by mass spectrometry to confirm the molecular mass of the corresponding molecular ion (i.e., [M+H]+/[M]+(column 4 of table shown in FIG. 3)).

Example 19

Plasma Hydrolysis of Nicotinamide Riboside Analogs to NR

This example shows that nicotinamide riboside esters and nicotinamide riboside hydride esters can be converted to nicotinamide riboside upon incubation with rat plasma.

Compounds were diluted with rat plasma to a concentration of 10 millimolar (mM). Samples were incubated for 30 min at 37° C., taking 50 microL aliquots for analysis at 0 and 30 min. The aliquots were loaded onto a deep 96 well plate, then 350 microL of 0.1% (v:v) formic acid in acetonitrile was added to each well. The plate was covered and sealed to prevent evaporation, then it was placed on an orbital plate shaker set to 800-900 rps for 5-10 minutes. Next, the plate was centrifuged at around 3000 rpm for 5 min to provide a clear supernatant. For LC/MS/MS analysis, 200 microL of supernatant from each well was transferred onto a clean plate, which was subsequently capped and placed into an autosampler.

LCMS Conditions. For each well, a 10 microL sample was injected via autosampler onto a Chromolithe Performance, RP-18e (100×4.6 mm) column, and eluted with a binary gradient. Solvent A=0.1% formic acid, 0.1% N,N-dibutyl-N-methylamine (DBME) in 2 mM aqueous ammonium acetate (1:1:1000 v:v:v). Solvent B=0.1% formic acid in acetonitrile (1:1000 v:v). The solvent gradient was as follows: 0-0.22 min, 95:5 A:B; 0.22-5.50 min, 95:5 A:B to 30:70 A:B (linear gradient); 5.05-6.05 min, 30:70 A:B; 6.05-6.60 min, 30:70 A:B to 95:5 A:B (linear gradient); 6.60-7.15 min, 95:5 A:B; stop elution at 7.15 min. Nicotinamide riboside eluted at approximately 1.7 min. A triple-quadrupole mass spectrometer was employed for peak identification. The identity of the analyte was confirmed by MS observation of a Q1 peak at m/z=255 (M)$^+$, and a Q3 peak at m/z=123.1 (M-C$_5$H$_8$O$_4$)$^+$.

The results are shown in FIG. 3, with the release of free nicotinamide riboside measured using by HPLC-MS at 0, 30, and 60 minute time points (columns 5, 6, and 7 of table shown in FIG. 3). For each of NR esters in Table 3, except nicotinamide riboside tribenzoate, nicotinamide riboside was detected at the 30 minute time point. Accordingly, the exemplary compounds of the invention including NRH triacetate, NRH tripropionate, NRH tributyrate, NRH triisobutyrate, NR+ (oxidized form of nicotinamide riboside) tripentanoate TFA (trifluoroacetic acid), NR+ trihexanoate TFA-(trifluoroacetate), NRH triethylcarbonate, NR+ monohexanoate, NRH monodecanoate, NRH monotetradecanoate, NR+ monooleate, NR+ monohexanoate, NR+ mononoonanoate, NR+ monododecanoate, NR+ monopentanoate, and NR+ monoundecanoate all were converted to free nicotinamide riboside to a significant degree. In contrast, NRH tribenzoate was not significantly converted to free nicotinamide riboside when incubated with rat plasma for 30 min at 37° C. Nic mononucleotide was also tested and showed some amount of conversion to free nicotinamide riboside under the same conditions.

Example 20

Nicotinamide Riboside Ester Predicted Oral Bioavailability

Figure 4:
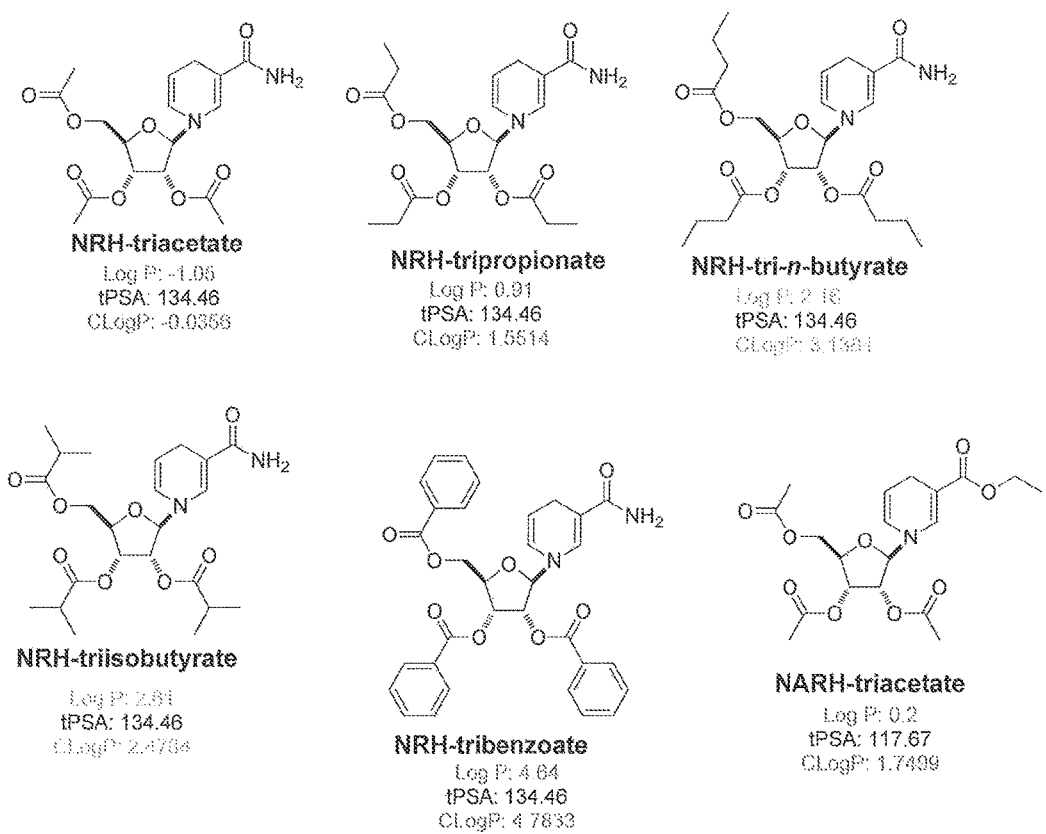
FIG. 4 shows the C Log P (calculated Log P) and tPSA (topolical polar surface area) values of several nicotinamide riboside ester compounds.

Solubility is an important physicochemical parameter for effective pharmaceutical agents. Computational methods can be used to predict solubility. For example C Log P is the "calculated" Log P. Log P is a partition-coefficient measure of the relative polarity vs. hydrophobicity of a compound. The Log P of a compound is critical because it affects the pharmacological, pharmacokinetic and pharmacodynamic properties of the compound in the body. An ideal C Log P range for oral bioavailability is between 2 and 4. As shown in FIG. 4, both NRH-tri-n-butyrate and NRH-triisobutyrate have C log P values within this range.

Accordingly, exemplary compounds of the invention have ideal physical properties for their use as pharmaceutical agents, and for use orally in particular.

Example 21

Nicotinamide Riboside Hydride Esters Raise Plasma NR Levels in Orally Dosed Mice Compounds were suspended in phospho-buffered saline (PBS) solution at 125 mg/mL. Eight mice were dosed via oral gavage with study compound at 500 mg/kg, (20 mg compound in 160 microL of PBS for a 40 g mouse). Four mice were euthanized via CO$_2$ asphyxiation at 2 h post-dose, then the remaining four were euthanized at 6 h post-dose, and blood was collected immediately following euthanasia via cardiac puncture, orbital bleed, or tail vein nick. Approximately 600 microL of blood was collected from each mouse. The blood samples were diluted with 5 volumes of 70% (1% sulfosalicylic acid/1 microM DTE/10 microM CD-38 inhibitor)/30% (37% 10 mM aqueous ammonium bicarbonate/63% acetonitrile). The mixture was vortexed, then centrifuged at 3000 rpm for 10 min at 4° C. to give a transparent supernatant. A 10 microL portion of the supernatant was analyzed by LCMS, using the conditions below.

LCMS Conditions. For each well, a 10 microL sample was injected onto a Chromolithe Performance, RP-18e (100×4.6 mm) column, and eluted with a binary gradient. Solvent A=0.1% formic acid, 0.1% N,N-dibutyl-N-methylamine (DBME) in 2 mM aqueous ammonium acetate (1:1:1000 v:v:v). Solvent B=0.1% formic acid in acetonitrile (1:1000 v:v). The solvent gradient was as follows: 0-0.22 min, 95:5 A:B; 0.22-5.50 min, 95:5 A:B to 30:70 A:B (linear gradient); 5.05-6.05 min, 30:70 A:B; 6.05-6.60 min, 30:70 A:B to 95:5 A:B (linear gradient); 6.60-7.15 min, 95:5 A:B; elution was stopped at 7.15 min. Nicotinamide riboside eluted at approximately 1.7 min. A triple-quadrupole mass spectrometer was employed for peak identification. The identity of the analyte was confirmed by MS observation of a Q1 peak at m/z=255 (M)+, and a Q3 peak at m/z=123.1 (M-C$_5$H$_8$O$_4$)$^+$.

Figure 5:
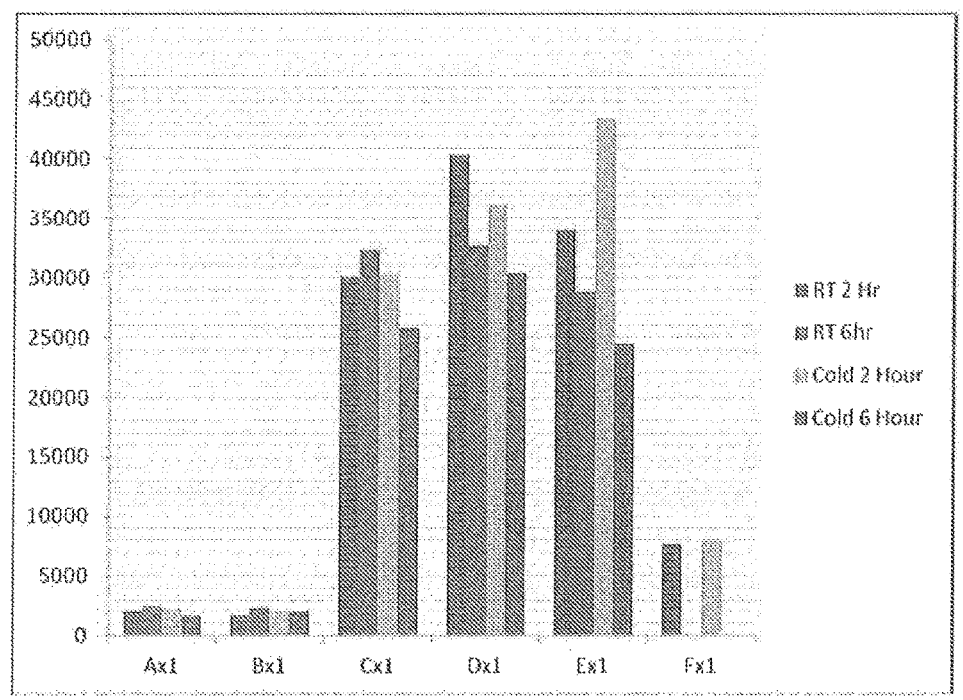
FIG. 5 is a bar graph showing blood levels of nicotinamide riboside in mice after orally dosing with NRH esters (A=blank control (PBS), B=nicotinic acid riboside hydride ethyl ester triacetate, C=Nicotinamide riboside hydride tri-isobutyrate, D=Nicotinamide riboside hydride tri-n-butyrate, E=Nicotinamide riboside hydride tripropionate, F=nicotinamide riboside hydride tribenzoate).

As shown in FIG. 5, nicotinamide riboside hydride tri-n-butyrate, nicotinamide riboside hydride triisobutyrate, and nicotinamide riboside tripropionate all raised plasma nicotinamide riboside levels substantially both 2 h and 6 h post-dose, while icotinamide riboside hydride tribenzoate showed only a very modest increase in nicotinamide riboside level 2 h post-dose. In the bar graph in FIG. 5, compounds are shown on the x-axis, and comparative LCMS signal is shown on the y-axis; with each compound dosed in mice at 500 mg study compound per 1000 g mouse as a solution or suspension in phospho-buffered saline solution (PBS) (A=blank control (PBS), B=nicotinic acid riboside hydride ethyl ester triacetate, C=Nicotinamide riboside hydride triisobutyrate, D=Nicotinamide riboside hydride tri-n-butyrate, E=Nicotinamide riboside hydride tripropionate, F=nicotinamide riboside hydride tribenzoate). As shown, samples were taken 2 hours and 6 hours post dose. Also as shown, samples were kept cold (4° C.) or at room temperature (approximately 23° C.) before analysis.

Example 22

Nicotinamide Riboside Triacetate Efficacy in DIO Mice

C57BL/6 DIO mice and lean controls were purchased from Taconic (Hudson, N.Y.). All mice were fed Purina 5001 chow ad libitum from weaning until 6 weeks of age, then DIO mice were fed a diet containing 60% fat, ad libitum. When the mice were 18 weeks old, dosing was begun. Mice were segregated into groups of 8, with group A receiving vehicle (1:1 (v:v) PEG400: water), group B receiving 100 mg/kg nicotinamide riboside hydride triacetate as a solution in vehicle, group C receiving 500 mg/kg nicotinamide riboside hydride triacetate as a solution in vehicle, and group D (chow-fed lean control mice) receiving vehicle. The mice were dosed once per day via oral gavage for six weeks. After three weeks of dosing, body weights, post-prandial blood glucose, and post-prandial blood insulin levels were measured using commercially available kits. After four weeks of dosing, fasted blood glucose and fasted blood insulin levels were measured. Nicotinamide riboside and NAD levels were measured after four weeks of dosing, using the same extraction and LCMS protocol as described in Example 21 with NAD giving an LC retention time=2.5 min, MS Q1 peak, m/z=664(M+H)+, Q3 peak, m/z=428 (M-$Cl_1H_{13}N_2O_4$). Statistical analysis was performed using one-way ANOVA, and Dunnett's post test.

Figure 6A:
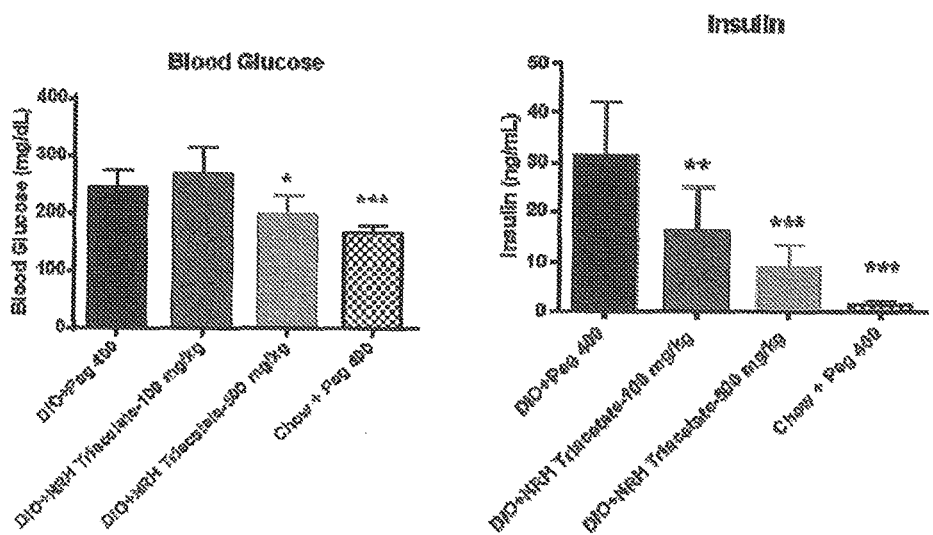
FIG. 6A depicts two bar graphs showing that both blood glucose and blood insulin levels were reduced by NRH-triacetate in DIO (Diet-Induced Obesity) mice.
Figure 6B:
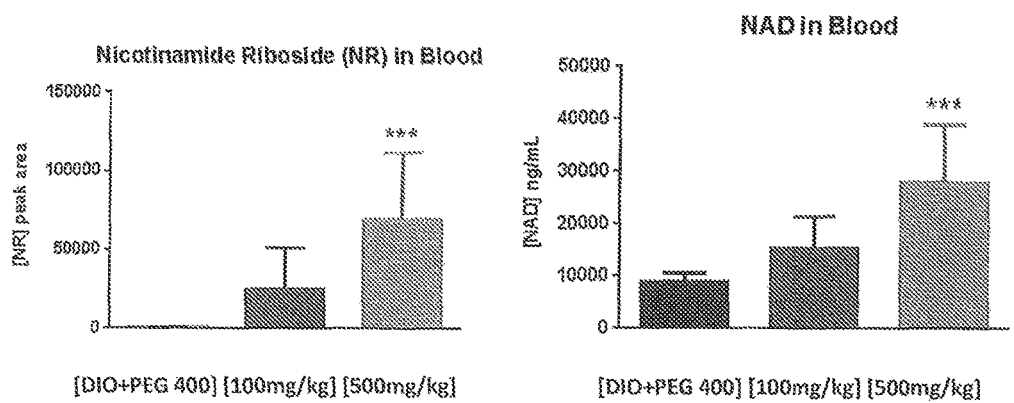
FIG. 6B depicts two bar graphs showing that both blood nicotinamide riboside and NAD levels rose in a dose-dependent manner by NRH-triacetate in DIO (Diet-Induced Obesity) mice.

FIG. 6A shows post-prandial glucose and insulin levels after three weeks of dosing high-fat fed DIO mice with vehicle or NRH-triacetate. Chow-fed mice were used as non-diabetic controls. FIG. 6B shows nicotinamide riboside and NAD levels in DIO mice after four weeks of dosing (first column (black)=vehicle control, second column (dark grey)=100 mg/kg NRH-triacetate, third column (light grey)=500 mg/kg NRH-triacetate; triple asterisk (***)=non-overlap of error bars between vehicle control and 500 mg/kg NRH-triacetate).

Accordingly, the results of these studies show that both blood glucose and blood insulin levels are reduced by NRH-triacetate (FIG. 6A), and that both blood nicotinamide riboside and NAD levels rise in a NRH-triacetate dose-dependent manner (FIG. 6B). Therefore this nicotinamide riboside hydride ester partially corrects two important parameters in an animal model of type 2 diabetes mellitus.

REFERENCES

Sauve, A. A.; Wolberger, C.; Schramm, V. L.; Boeke, J. D. *Annu. Rev. Biochem*, 2006, 75, 435-465
Alberts, B.; Bray, D.; Lewis, J.; Raff, M.; Roberts, K.; Watson, J. D. Molecular Biology of the Cell, 3rd ed., 1994, pg 670, Garland Publishing, New York
Cantó, C.; Houtkooper, R. H.; Prinnen, E.; Youn, D. Y.; Oosterveer, M. H.; Cen, Y.; Fernandez-Marcos, P. J.; Yamamoto, H.; Andreux, P. A.; Cettour-Rose, P.; Gademann, K.; Rinsch, C.; Schoonjans, K.; Sauve, A. A.; Auwerx, *J. Cell Metabolism*, 2012, 15, 838-847.
Yoshino, J.; Mills, K. F.; Yoon, M. J.; Imai, S.-I. *Cell Metabolism* 2012, 14, 528-536.
Tanimori, S.; Ohta, T.; Kirihata, M. Bioorg. *Med. Chem. Lett.*, 2002, 12, 1135-1137.
NR-Yang, T.; Chan, Y. K.; Sauve, A. A. *J. Med. Chem.*, 2007, 50, 6458-6461
Liao, S.; Dulaney, J. T.; Williams-Ashman, H. G. *J. Biol. Chem.*, 1962, 237, 2981-2987.

Example 23

NRH Increases NAD in Both HaCaT Cells (a Human Keratinocyte Cell Line) and Normal Human Primary Dermal Fibroblasts Nicotinamide adenine dinucleotide (NAD) is a substrate for many enzymes, including ADP-ribosyl transferases, poly (ADP-ribose) polymerases and sirtuins. These enzymes are involved in numerous fundamental cellular processes, including DNA repair, stress responses, signaling, transcription, apoptosis, metabolism, differentiation, chromatin structure, and life span. $NAD^+$ can be derived from tryptophan or aspartic acid (de novo synthesis) or derived from niacin, niacinamide, NRH (salvage pathway). It has been hypothesized that increasing NAD levels in skin cells could lead to many skin benefits including decreased DNA-damage in cells, longer cellular life span and delayed aging rate, however direct evidence is needed. To bridge the gap between existing knowledge regarding the biological effects of intracellular NAD levels and skin health benefits, the following examples provide biological evidence that skin cell biology is significantly improved by administration of the NR analogs of the invention.

HaCaT cells (AddexBio Technologies, San Diego, Calif., Passage 16-19) were grown in Medium DMEM/GlutMax (Life technologies, Grand Island, N.Y.) supplemented with 10% FBS (Life technologies) and Non-essential amino acids (NEAA, Life technologies) and then seeded in 12-well plates (Corning, Tewksbury, Mass.) with a density at $2 \times 10^5$ cells per well and 2 ml of culture medium in each well for overnight.

Human primary dermal fibroblasts derived from adult human skins (HDFa, Life technologies, Grand Island, N.Y., Passage 2-4) were grown in Medium 106 (Life Technologies) supplemented with Low Serum Growth Supplement (LSGS) (Life Technologies) and seeded in 12-well plates with density at $2 \times 10^5$ cells per well and 2 ml of culture medium in each well.

Figure 7:
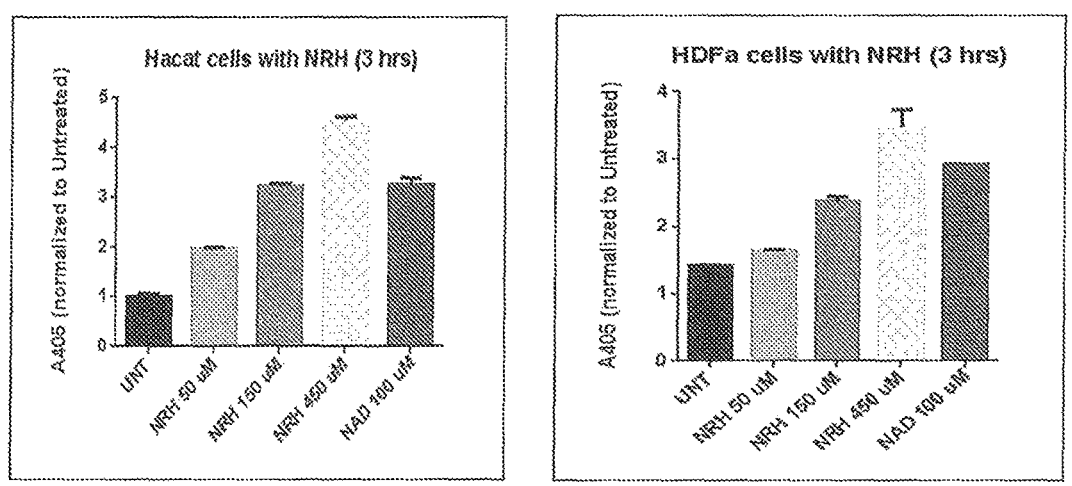
FIG. 7 depicts two bar graphs illustrating that NRH dose-dependently increases NAD in both keratinocytes and dermal fibroblasts, and NRH at 150 μM leads to a level similar to a NAD control at 100 μM.

Stock solution of dihydronicotinamide riboside (NRH, GSK3008320A, GSK, RTP, NC) was prepared in ethanol at 100 mM (25.6 mg/ml) and stored at −20° C. Cells were treated with different concentrations of NRH for 3 hrs, washed twice with PBS containing 5 mM EDTA, and then subject to Nicotinamide adenine dinucleotide (NAD) measurement. In brief, acetonitrile (ACN) lysis buffer (Ammonium Acetate (50 mM) and 90% acetonitrile) was added to each well (200 µl/well) to lyse the cells at RT for 5-10 mins by gently rotating on a culture plate shaker at a low speed. Enzyme master mix (300 µM of 5-Amino-(3,4'-bipyridin)-6(1H)-one (Inamrinone) (Sigma-Aldrich), a substrate for ADP ribosyl cyclase (ADPR cyclase)) and 30 nM ADPR Cyclase (Sigma, St. Louis, Mo.), 7.5 µM of N-(2-fluoro-4-(methylsulfonyl)phenyl)-2-methyl-6-(thiazol-5-yl)isonicotinamide (a CD38 inhibitor) in 75 mM HEPES pH7 buffer (Life Technologies)) was added to the lysed cells (400 µl of enzyme master mix/well). Enzymatic reaction was incubated at RT for ~30 min. At the end of incubation, the supernatant (200 µl) of the reaction solution from each well was transferred to each well of a 96-well plate and absorbance was read twice in the 96-well plate at 405 nm using a plate reader (Spectra Maxplus, Molecular Devices, Sunnyvale, Calif.). A mixture of enzyme master mix and ACN extraction solution at 2:1 ratio was used as a blank reference. NAD (Sigma) was used as a positive control. Study results are shown in FIG. 7, which demonstrates that NRH dose-dependently increases $NAD^+$ in both keratinocytes and dermal fibroblasts as measured by absorbance at 405 nm.

Example 24

Figure 8:
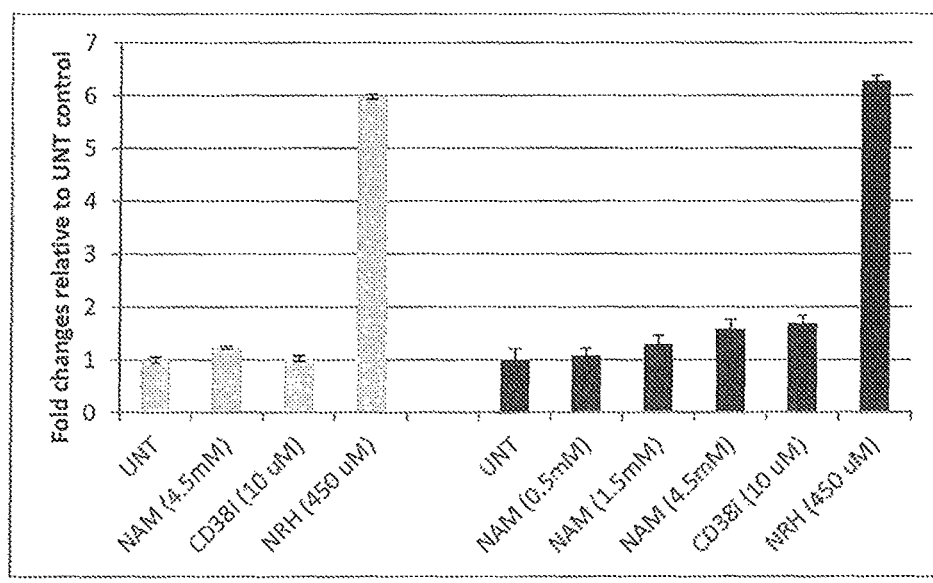
FIG. 8 is a bar graph illustrating the effects on intracellular NAD levels in HaCaT cells from treatment with NRH, a CD38 inhibitor, and niacinamide cultured in media with or without Vit B3.

NRH Strongly Induces $NAD^+$ Levels Relative to a CD 38 Inhibitor and Niacinamide HaCaT cells were grown as described in example 23 in the regular cell culture DMEM medium as described earlier or in the Epilife medium without nacinamide (Life Technologies). Cells were treated with different concentrations of NRH or niacinamide (NIA, DSM nutritional products) for 3 hrs, washed twice with PBS containing 5 mM EDTA, and then subject to Nicotinamide adenine dinucleotide (NAD) measurement as described in example 23. A mixture of enzyme master mix and ACN extraction solution at 2:1 ratio for a blank reference. NAD (Sigma) was used as a positive control. Study results are shown in FIG. 8, which illustrates that NRH at 450 µM treatment elevated NAD levels ~6 fold, while Niacinamide and N-(2-fluoro-4-(methylsulfonyl)phenyl)-2-methyl-6-(thiazol-5-yl)isonicotinamide, a CD38 inhibitor, at highest tested doses did not lead to NAD elevation in the HaCaT cells cultured in DMEM medium with Vit B3 (acid form of niacinamide) (see open bars). Both the CD38 inhibitor and Niacinamide increased NAD in the HaCaT cells cultured in the Vit B3 depleted culture medium, and the induction of NAD by niacinamide was dose-dependent (solid bars). However, the induction of NAD by niacinamide (highest at ~1.5 fold) was low compared to those by NRH. Therefore, NRH is a stronger NAD inducer compared to a CD38 inhibitor or Niacinamide.

Example 25

Differential Effect of NRH and NRH Esters on NAD Levels in HaCaT Cells

Figure 9A:
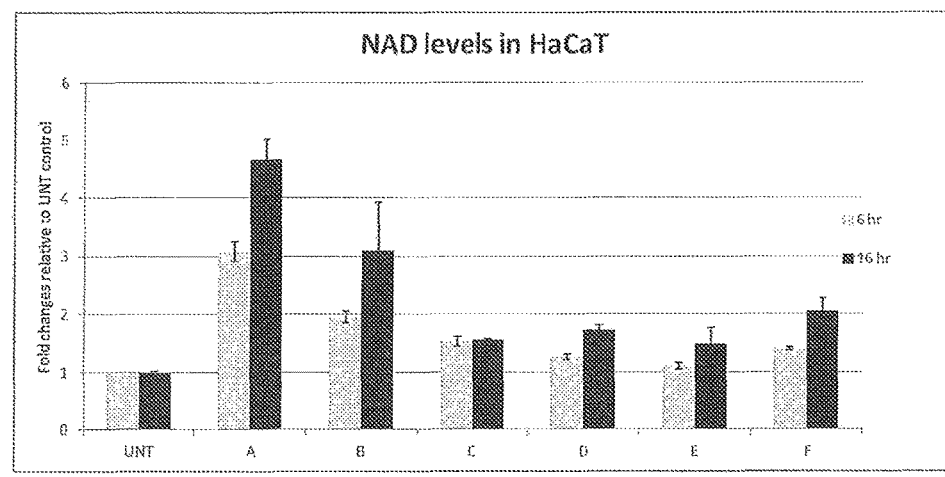
FIG. 9A is a bar graph illustrating that NRH monoC16 showed a higher NAD boosting activity compared to all the other tested NR esters at 150 μM.

HaCaT cells were grown in regular culture media as described in example 1 and seeded in 12-well plates with density at $2 \times 10^5$ cells per well and 1 ml of culture medium in each well. NRH stock solution was prepared in ethanol at 100 mM (25.6 mg/ml) and stored at −20° C. Stock solutions of NRH esters were made at 50 mM in DMSO (see FIG. 9B for compound info). Cells were treated with NRH esters and NRH at 150 µM for 6 and 16 hrs, washed twice with PB S containing 5 mM EDTA, and then subject to Nicotinamide adenine dinucleotide (NAD) measurement as described in example 23. Study results are shown in FIG. 9A, which illustrates that NRH monoC16 showed a higher NAD boosting activity compared to all the other tested NR esters at 150 µM. However, noticeable precipitations occurred when the stock solution of NRH monoC16 was added to the media, suggesting a solubility issue that may have limited availability of the compound to the cells. Cells treated with NR monooleate TFA monoC16 at 150 µM appeared unhealthy, indicating potential cytotoxicity triggered by the compound. As a positive control, NRH (150 µM) consistently showed strong activity on NAD elevation.

Example 26

NRH monoC16, a NRH C16 Ester, Dose-dependently Increases NAD in HaCaT Cells

Figure 10:
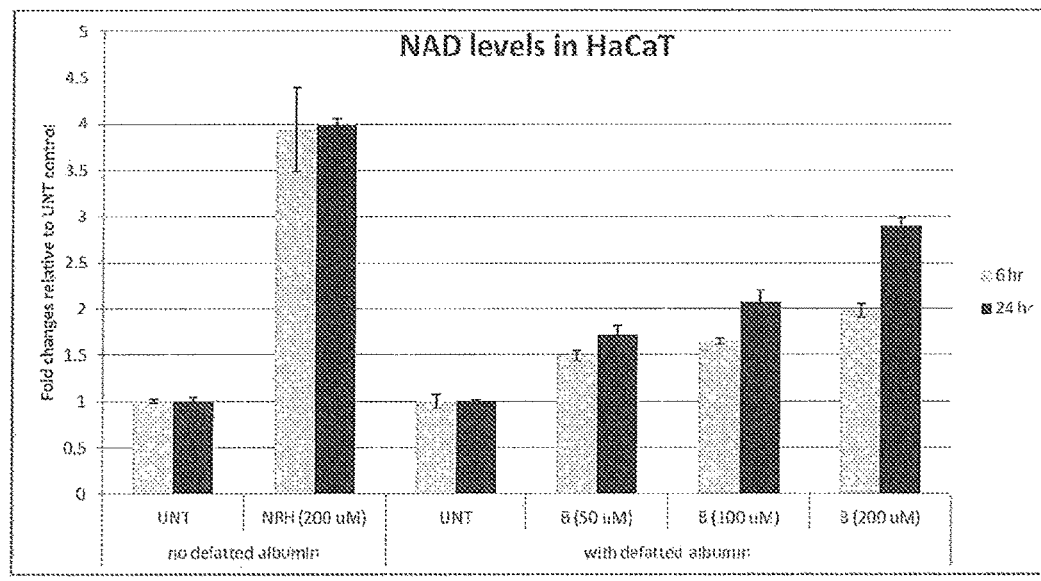
FIG. 10 is a bar graph illustrating that NRH monoC16 increases NAD levels in a dose dependent manner.
Figure 10:
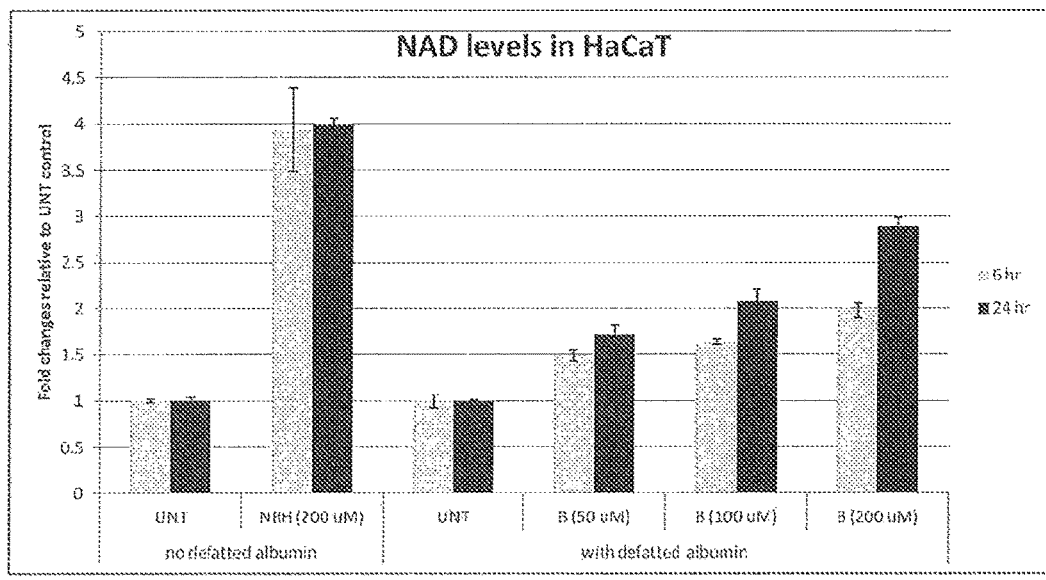

HaCaT cells were grown in regular culture media as described above and seeded in 12-well plates with density at $2 \times 10^5$ cells per well and 1 ml of culture medium in each well. NRH stock solution was prepared in ethanol at 100 mM (25.6 mg/ml) and stored at −20° C. NRH (200 µM) was used as a positive control. Because of the possible solubility issue related to NRH monoC16, fatty acid-free bovine serum albumin (defatted BSA, Sigma) was used as a carrier for the compound. NRH monoC16 stock solution (100×) was complexed with defatted BSA (1 M) prior to the treatment, resulting in a NRH monoC16 stock solution (10 ×). NRH monoC16 was then added to the culture media giving a final BSA concentration of 100 µM. With this method, no precipitation was observed. Defatted BSA was also added to the control samples at a final concentration of 100 µM. Cells were treated with NRH at 200 M and different concentrations of NRH monoC16 for 6 and 24 hrs, washed twice with PBS containing 5 mM EDTA, and then subject to Nicotinamide adenine dinucleotide (NAD) measurement as described in example 1. Study results are shown in FIG. 10, which illustrates that NRH monoC16 increased NAD levels in a dose dependent manner. However, their NAD boosting activities is slightly lower than that of NRH at the same concentrations. Compared with 6 hr treatment, a higher activity was observed after incubating the compound with cells for 24 hr, suggesting longer incubation may be necessary for the NRH ester compound to be biologically active.

Example 27

NRH Reduces H2O2-induce Reactive Oxidative Species (ROS)

Figure 11:
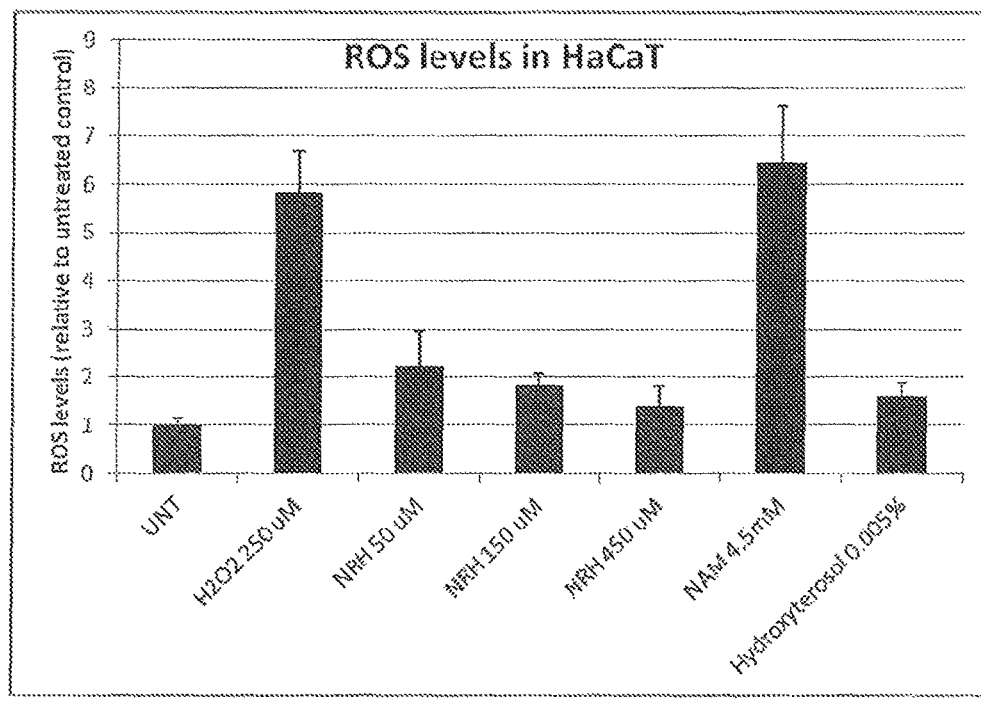
FIG. 11 is a bar graph illustrating reactive oxygen species (ROS) levels in HaCaT cells treated with $H_2O_2$, NRH, niacinamide, and hydroxyterosol.

HaCaT cells were grown as described in example 23 and were seeded in 96-well plates (Nunc™ black with optical bottom, Thermo Fisher Scientific, Inc., Waltham, Mass.) with a density at $2 \times 10^4$ cells per well and 100 µl medium in each well, and grown overnight before treatments. Stock solutions of NRH and other test compounds were prepared and diluted to 2× of final treatment concentrations in DMEM medium in 96-well storage plate as indicated in the FIG. 11. HaCaT Cells were treated in triplicates by adding 100 µl of diluted solutions of test compounds (2×) to each well containing 100 µl medium already. Cells were incubated in the presence of test compounds for 3 hrs. At the end of 3 hr incubation, cells were washed once with 200 µl DPBS with $Ca^{++}$ and $Mg^{++}$ (Life Technologies) and then fed with 100 µl DMEM medium each well containing $H_2O_2$ at 250 µM (as a ROS (reactive oxygen species) inducer, Sigma). After 30 min incubation, cells were washed once with 200 µl DPBS with $Ca^{++}$ and $Mg^{++}$ and CellROX deep red reagent (2.5 mM stock solution, Life Technologies) was added to the medium to a final concentration of 5 µM. After 1 hr incubation at 37° C., 5% $CO_2$, Cells were washed for 3 times with DPBS, fluorescence signal was read at Ex. 640 nm and Em. 665 nm in Biotek Synergy $H_4$ microplate reader (BioTek, Winooski, Vt.). Untreated cells were served as controls (normalized to 1). All the treated samples were normalized to the untreated control. ROS levels of tested compounds are shown in FIG. 11. FIG. 11 illustrates that HaCaT cells treated with 250 µM $H_2O_2$ exhibited a ~6-fold increased level of ROS. Hydroxyterosol at 0.005%, a positive control of antioxidant, reduced $H_2O_2$-induced ROS. NRH showed dose-dependent inhibitory activities against $H_2O_2$-induced ROS, while niacinamide at 4.5 mM did not inhibit $H_2O_2$-induced ROS.

Example 28

NRH Reduces TNFα-induced COX-2 Gene Expression in Dermal Fibroblasts

Figure 12A:
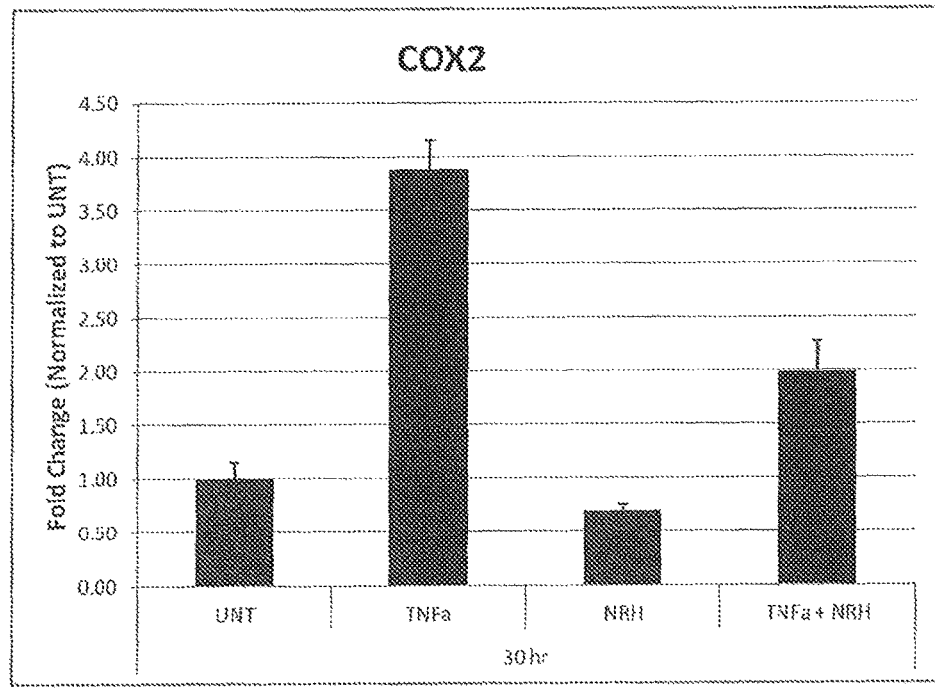
FIG. 12A is a bar graph illustrating the effects of NRH on TNF-α induced COX2 gene expression.
Figure 12B:
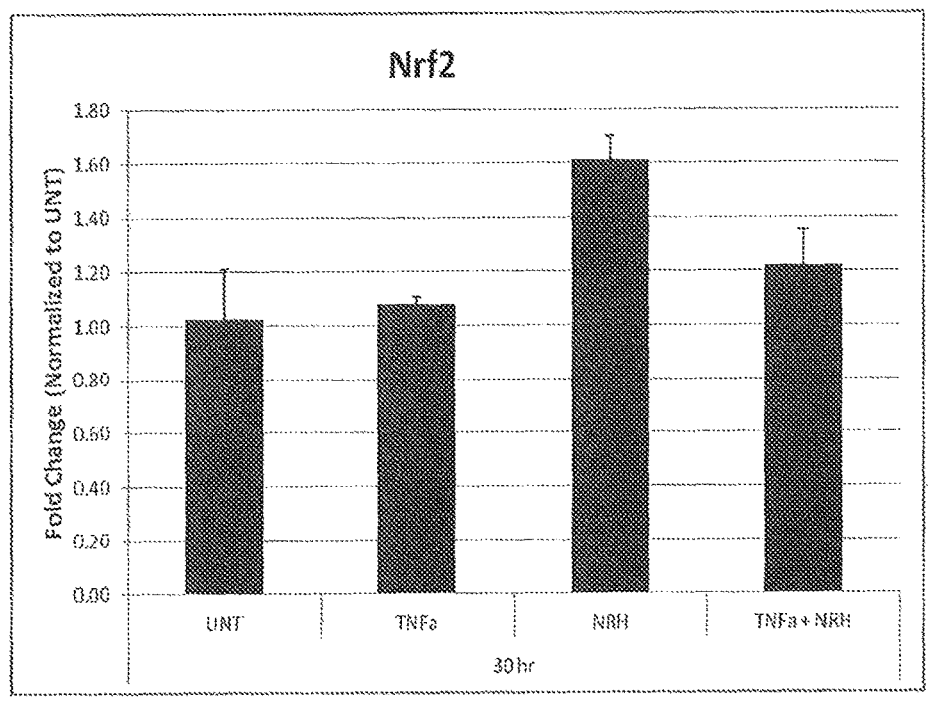
FIG. 12B is a bar graph illustrating the effects of NRH on TNF-α induced NRF2 gene expression.

Human dermal fibroblasts were grown in regular culture media as described in example 23 above and seeded in 12-well plates at $2 \times 10^5$ cells per well for overnight. Cells were then replenished with fresh medium and treated with TNFα (10 ng/ml) with and without NRH (200 µM) for 30 hr. At the end of the incubation, cells were washed once with HBSS with $Ca^{2+}$ and $Mg^{2+}$ (Life Technologies), and subject to RNA isolation and QPCR analyses. QPCR result of COX-2 gene is shown in FIG. 12A, which illustrates that TNF-α induced COX-2 gene expression, while NRH treatment reduced basal and TNF-α-induced COX-2 gene expression in dermal fibroblasts. In addition, NRH also slightly increased the expression level of NRF2.

Example 29

Figure 13A:
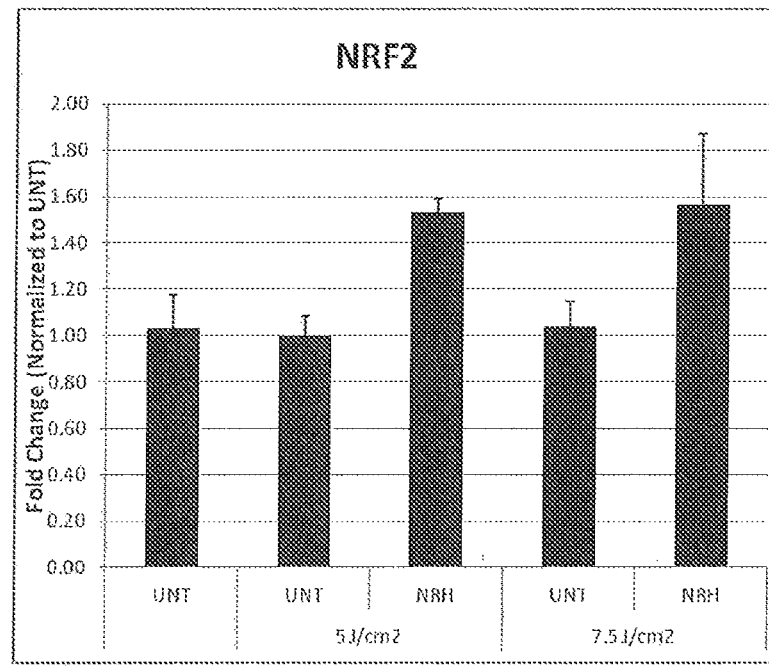
FIG. 13A is a bar graph illustrating that NRH treatment increases NRF2 expression compared to untreated control following UVA irradiation.
Figure 13B:
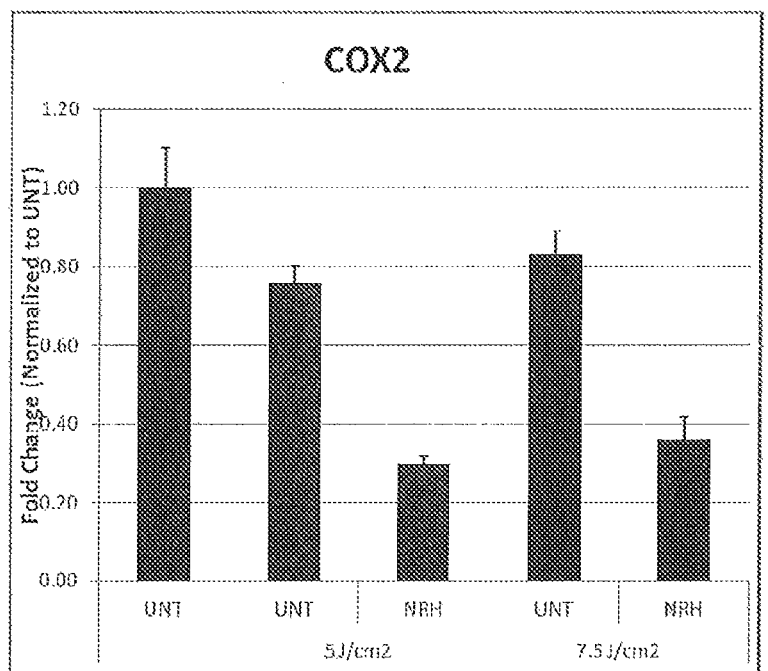
FIG. 13B is a bar graph illustrating that NRH treatment decreases COX2 expression compared to untreated control following UVA irradiation.
Figure 13C:
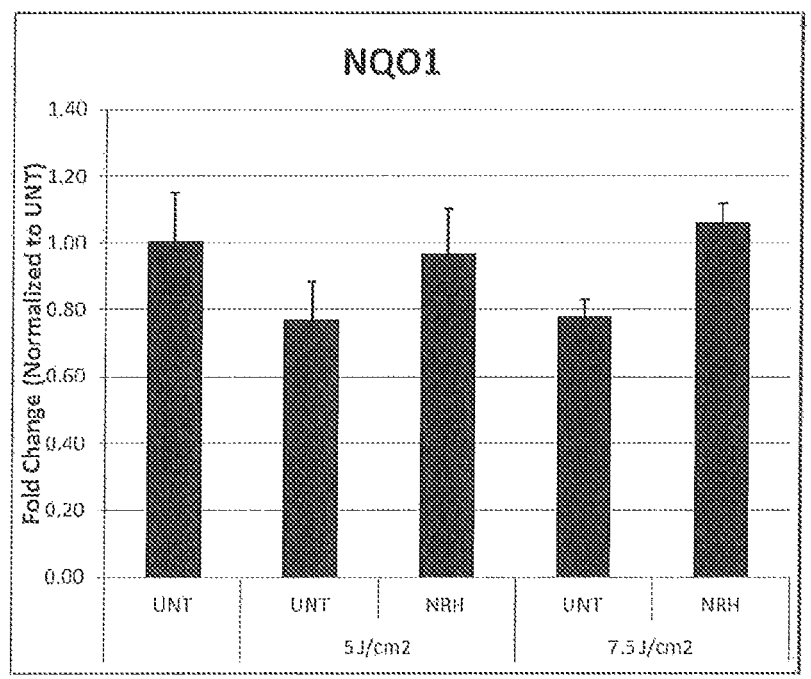
FIG. 13C is a bar graph illustrating that NRH treatment increases NQO1 expression compared to untreated control following UVA irradiation.

NRH Reduces UVA-induced COX-2 and Increases NRF2 Expression and NQO-1 by QPCR in Dermal Fibroblasts Human dermal fibroblasts were grown in regular culture media as described in example 1 and seeded in 12-well plates at $2 \times 10^5$ cells per well for overnight. Before UVA exposure, culture media were removed and PBS (500 µl) was added to each well. Cells were treated with NRH at 200 µM in culture media for 5 days, and only exposed to UVA at 5 $J/cm^2$ or 7.5 $J/cm^2$ every other day on day 0 and day 3. The Newport DS-101103 UV Solar Simulator with UV-A-F filter (Sol-UV-A-F) (Newport Corporate) was used as the UVA emitter. Measurement of the irradiation was taken using an ILT-1400-A radiometer/photometer with a UVA probe (SSL001A, international light technologies, Inc.). After UVA exposure, PBS was removed from each well and media with NRH were added to cells. Cells were harvested for RNA isolation after 5 days treatment. QPCR results are shown in FIGS. 13A, 13B and 13C, which illustrate that NRH treatment reduced COX-2 and increased NRF-2 and NQO-1 compared to UVA alone, suggesting that NRH can reduce inflammation and increase endogenous antioxidant enzyme systems.

Example 30

NRH Reduces UVB-induced Inflammation Mediators (TNF-α and IL-8) in Reconstructed Epidermal Equivalents Solar Ultraviolet (UV) light exposure on skin causes photoaging, sunburn, DNA damages and carcinogenesis. UV radiation (UVR) also results in inflammation, which can be measured in vitro by pro-inflammatory mediators, e.g., TNF-α, IL-8. The in vitro reconstructed human epidermis (RHE) model is used to evaluate the anti-inflammatory effect of NRH.

Figure 14A:
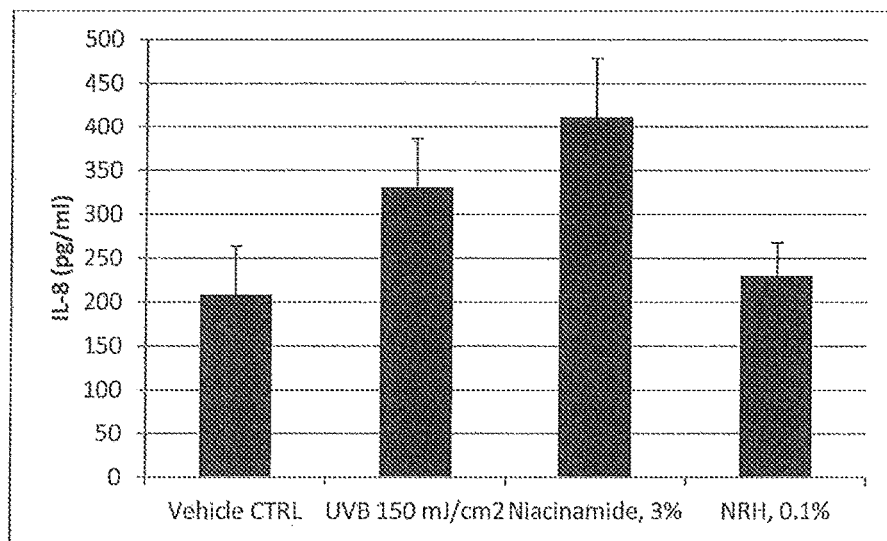
FIG. 14A is a bar graph illustrating that NRH, but not Niacinamide, reduces UVB-induced IL-8.
Figure 14B:
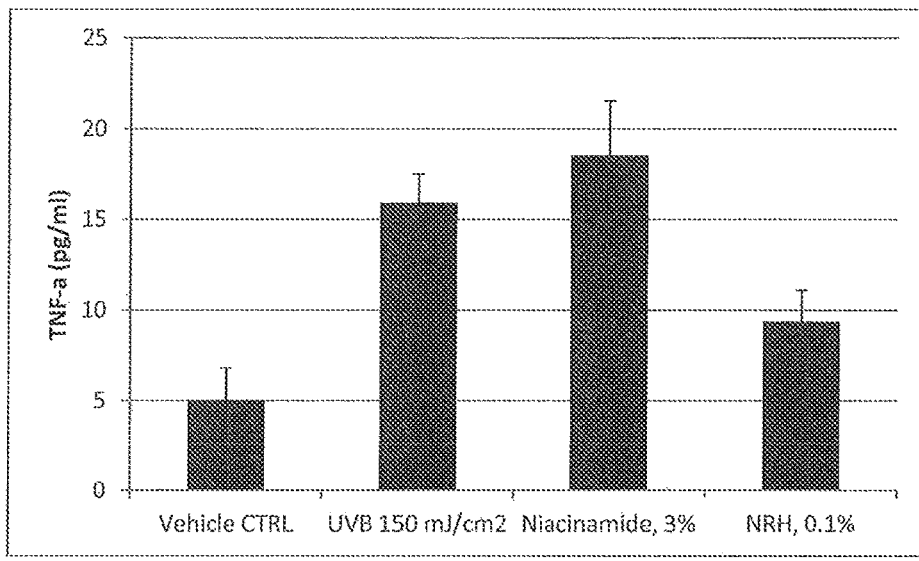
FIG. 14B is a bar graph illustrating that NRH, but not Niacinamide, reduces UVB-induced TNF-α.

Reconstructed human epidermis (EpiDerm, EPI-200, made of normal human epidermal keratinocytes, MatTek, Ashland, Mass.), were placed into media (EPI-100-ASY, 1.0 ml/well of 6-well plates) and incubated overnight at 37° C./5% $CO_2$. The media was replenished with fresh culture media prior to study. NRH at 0.1% and niacinamide at 3% in vehicle (50% $H_2O$/35% ethanol/15% propylene glycol, v/v/v) were applied topically at 6 µl and then gently spread onto the skin equivalents (~20 rotations) using the rubber side of a plunger of 1 ml syringe. Vehicle was served as an untreated control. After 1 hr pre-treatment with NRH, niacinamide, or vehicle control, the EpiDerm tissues were transferred to a sterile 6-well plate containing 1 ml of DPBS per well and then exposed to UVB at 150 $mJ/cm^2$. The Newport Solar Simulator System (Power unit 69920, and Lamp 91192-1000, Newport Corporate, Irvine, Calif.) was used as the UVB emitter to achieve a UVB irradiation of 150 $mJ/cm^2$. Measurement of the irradiation was taken using an ILT-1400 Handheld, Portable Radiometer/Photometer (International Light Technologies, Inc., Peabody, Mass.) with a UVB detector (SEL240/T2ACT5, 235-307 nm, International Light Technologies, Inc.). After UVB irradiation, EpiDerm tissues were transferred back to the 6-well plate containing media and incubated at 37° C./5% CO2 for 6 hours. At the end of the incubation (6 hr post UVB irradiation), culture media were collected for the measurement of IL-8, and TNF-α concentration by MagPix (Millipore, HCYTOMAG-60K). The study results are shown in FIGS. 14A and 14B, which illustrate that UVB exposure (150 $mJ/cm^2$) resulted in markedly increases in the pro-inflammatory mediators such as TNF-α and IL-8. Pre-treatment of NRH inhibited UVB-induced TNF-α and IL-8, while niacinamide did not inhibit UVB-induced cytokine release.

Example 31

Further Physical Properties and Analyses of NRH and Esters Thereof

X-Ray Diffraction (XRD): Samples were analyzed using a PANalytical X'Pert Pro MPD-XRD (PW3040) X-ray powder diffractometer equipped with a copper X-ray tube as the source and an X'celerator 1-D silicon strip detector with a nickel filter to remove $K_\beta$ radiation. Data were collected from 2 to 50 degrees 2θ. Samples were applied as thin layers to silicon zero background disks.

Gravimetric Vapor Sorption (GVS): Samples were analyzed using a VTI corporation (now part of TA Instruments) SGA-100 with Cahn microbalance equipped with quartz sample and reference pans. Samples were dried in the SGA-100 under dry nitrogen for 5 hours at 25° C. followed by a moisture absorption step ramp from 5% relative humidity (RH) to 95% or 90% RH followed by a desorption step ramp back to 5% or 10% RH (all steps at 25° C.). The samples were held at each % RH step for 4 hours.

Optical Microscopy: Selected samples were imaged with an Olympus BX51 polarizing light microscope.

Differential Scanning Calorimetry (DSC): Selected samples were scanned using hermetically sealed TA Instruments Tzero aluminum pans with a TA Instruments Q100 differential scanning calorimeter at a linear heating rate of 5° C./min from 20 to 200° C.

Thermogravimetric Analysis (TGA): Selected samples were analyzed by TGA using a TA Instruments Q5000 with a 100 µL Pt sample pan. Samples were heated from ambient to 300° C. at 10° C./min under the "Hi-Res" mode with 3.0. The TGA slows the heating rate as weight changes are detected.

Results

Figure 15:
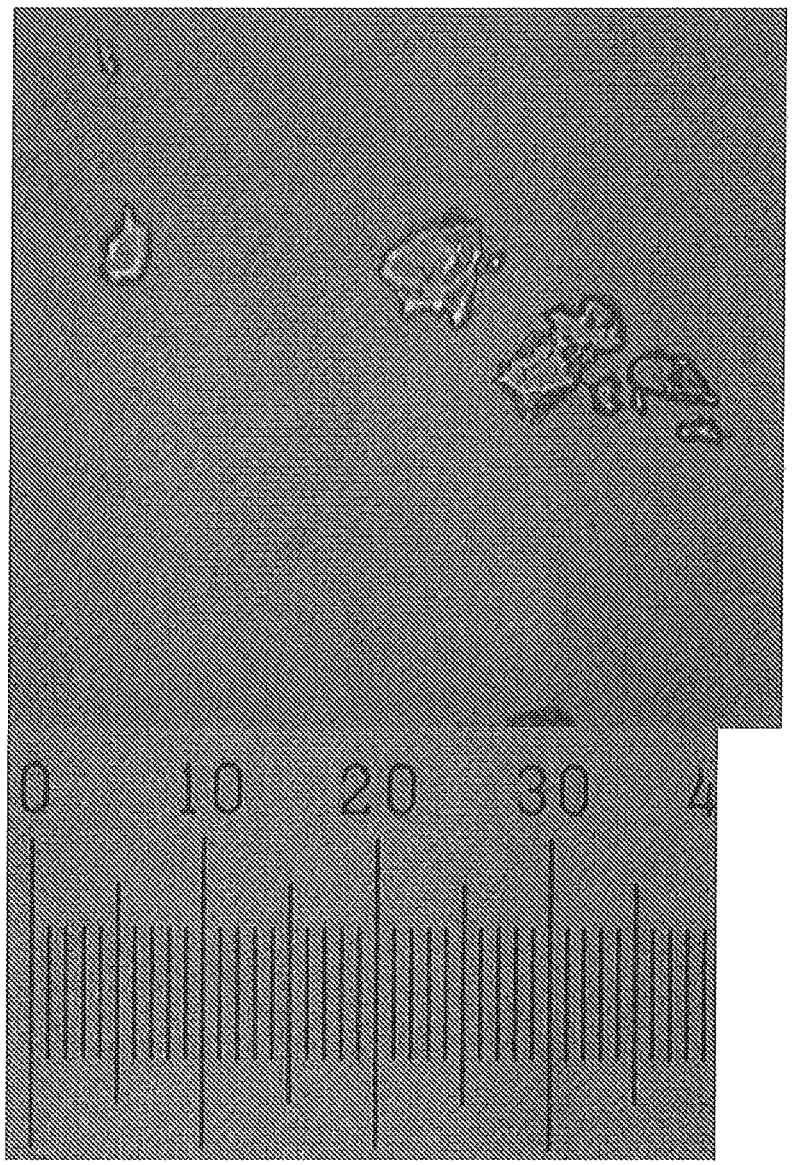
FIG. 15 is a photograph showing NRH particles imaged by optical microscopy (Scale bar: 1 division=10 microns FIG. 16 is an XRD plot of the NRH preparation.

NRH particles were yellow, glassy, and transparent in appearance by optical microscopy. When viewed under cross polars, the particles were not birefringent. See FIG. 15, which shows NRH particles imaged by optical microscopy (Scale bar: 1 division=10 microns)

Figure 16:
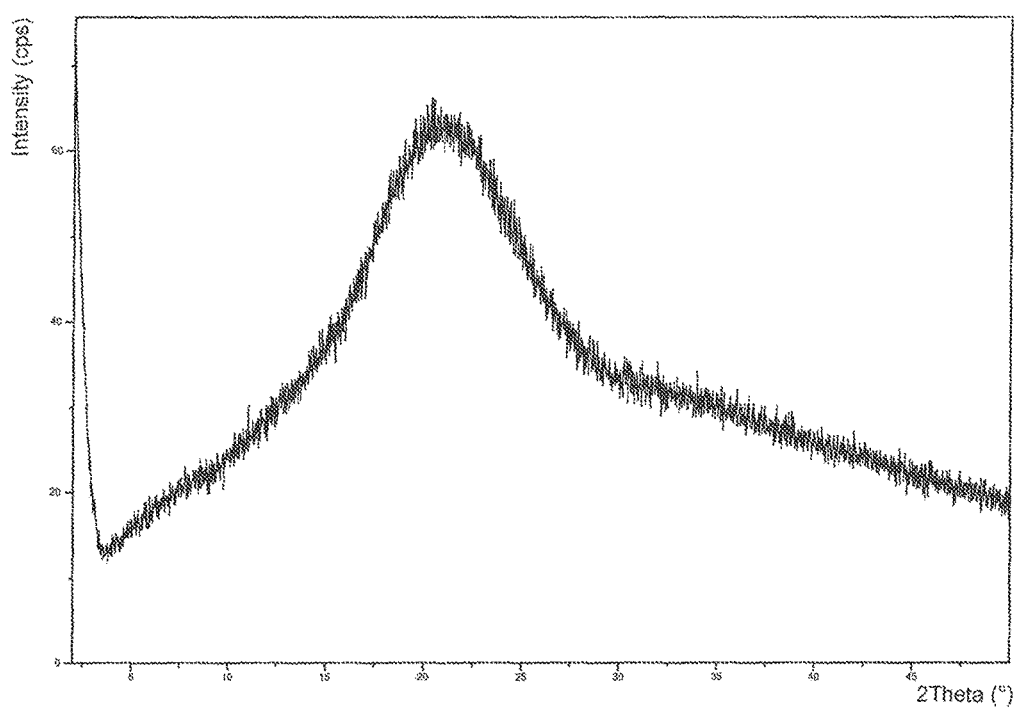

XRD indicated the sample was amorphous (FIG. 16). A sample of NRH was stored in a 93% RH (relative humidity) salt chamber (at approximately 22° C.) for approximately 2¼ hours. The sample had deliquesced and there was no evidence of crystallization based on XRD analysis.

DSC showed no thermal behavior other than due to thermal decomposition. TGA analysis indicate the sample contained approximately 2.3% w/w volatiles content based on weight loss from ambient to approximately 100° C. Further weight loss above 100° C. was attributed to thermal decomposition.

Figure 17:
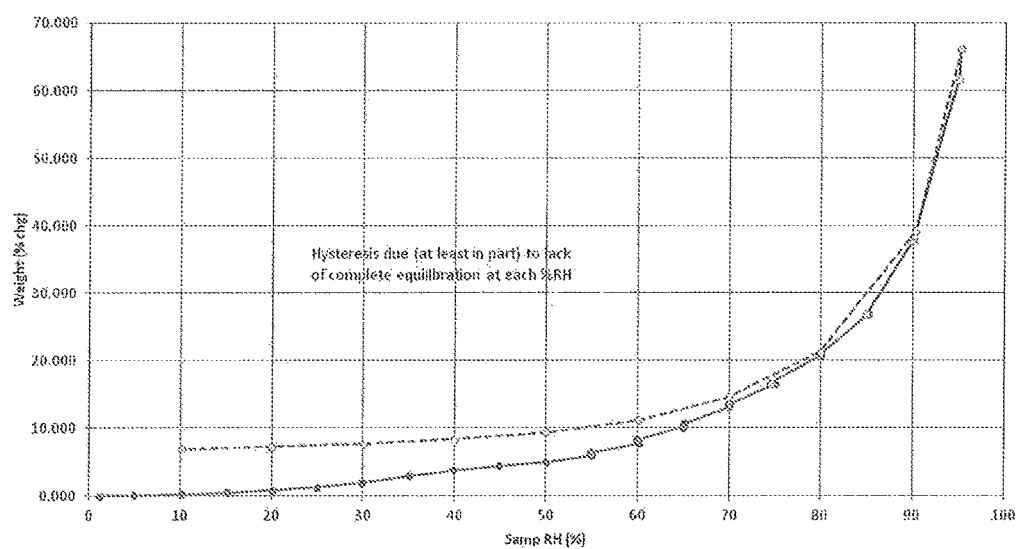
FIG. 17 is a GVS Isotherm (25° C.) of the NRH preparation (the solid line is the absorption phase and the dashed line is the desorption phase).
Figure 18:
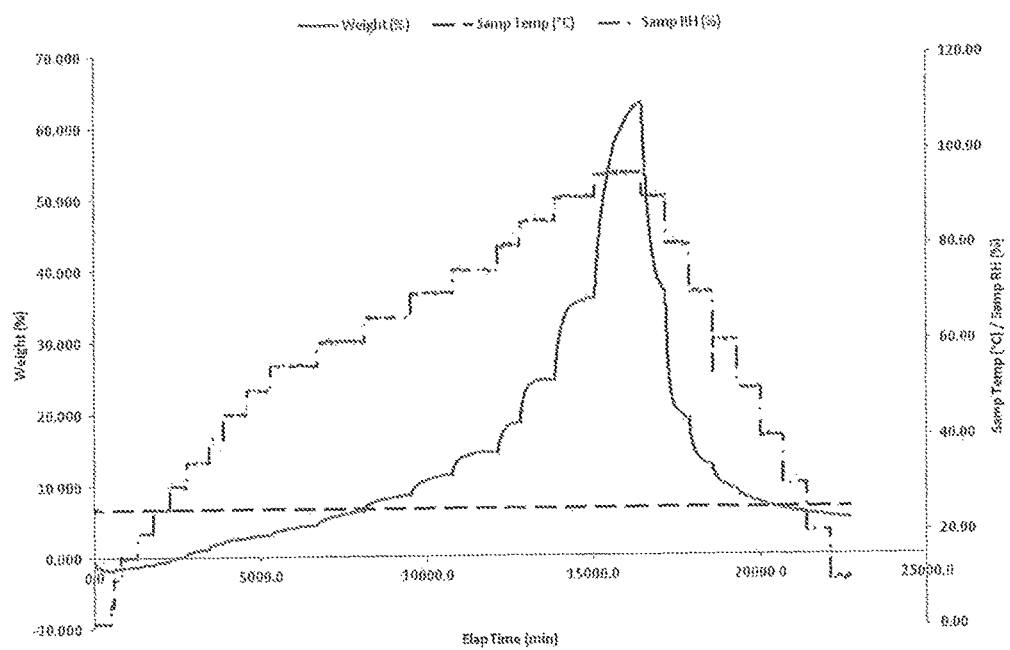
FIG. 18 is GVS weight versus time profile, of the NRH preparation (% RH (25° C.) steps are shown along with the sample % w/w change from the initial dried state).

During the drying stage (under dry nitrogen at 25° C.), the sample lost a similar weight percentage as observed by TGA. After drying, the sample gained weight with increasing % RH (25° C.). At 90% RH, the sample gained greater than 60% w/w. The GVS Isotherm and corresponding weight versus time plot are shown in FIGS. 17 and 18 respectively. The results in FIG. 18 indicate the sample weight has not reach equilibrium during the 4-hr period at each 80 and 90% RH steps, so the % weight gain presented in FIG. 3 at 80 and 90% RH are likely to be slightly lower than the true equilibrium values.

GVS (Gravimetric Vapor Sorption) indicates the sample is hygroscopic, as shown in FIG. 17 (GVS Isotherm (25° C.), NRH, the solid line is the absorption phase and the dashed line is the desorption phase).

Figure 19:
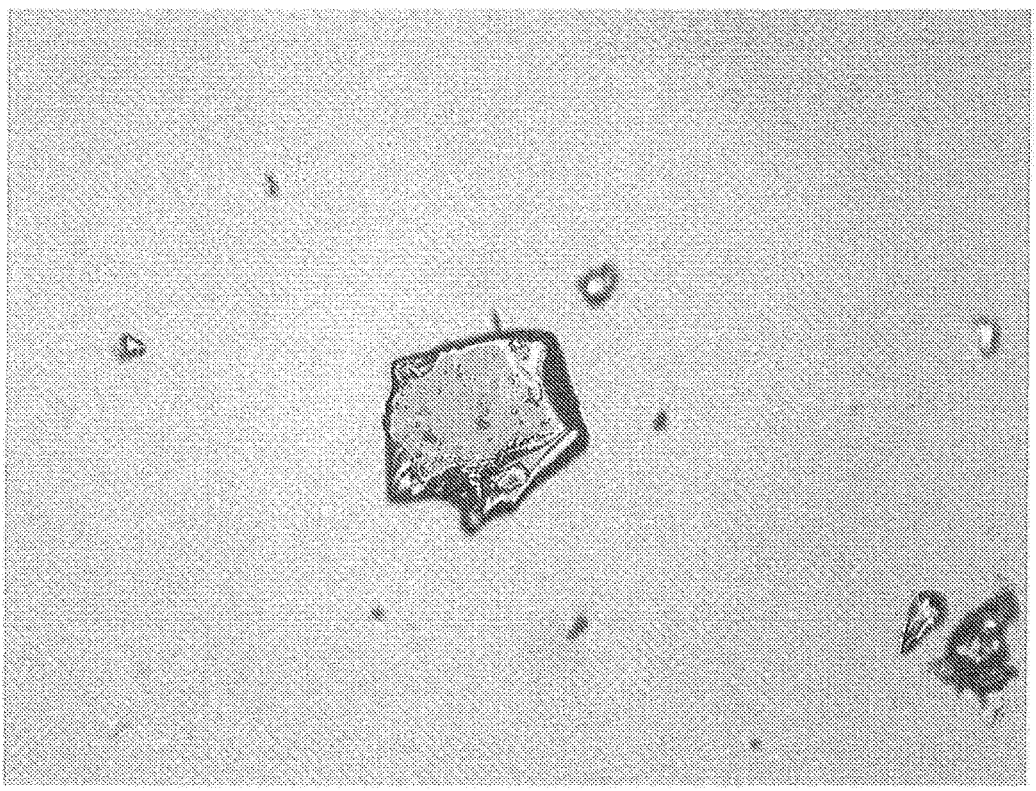
FIG. 19 is a photograph showing NRH particles imaged by optical microscopy (Scale: Each division=10 microns).
Figure 19:
Figure 20:
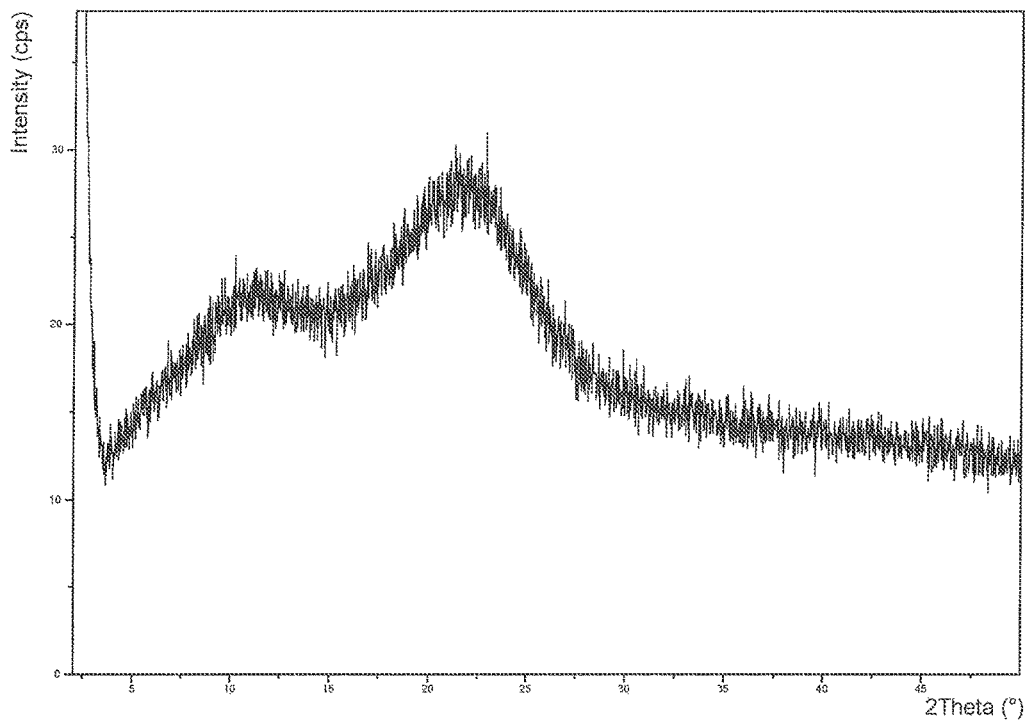
FIG. 20 is an XRD plot of the NRH triacetate derivative.
Figure 21:
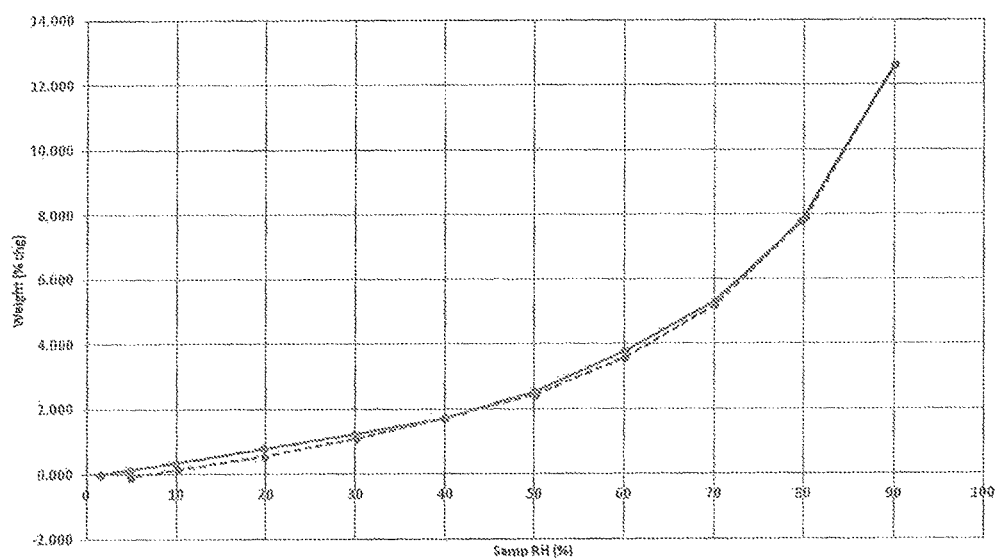
FIG. 21 is a GVS Isotherm (25° C.) of the NRH triacetate derivative.
Figure 22:
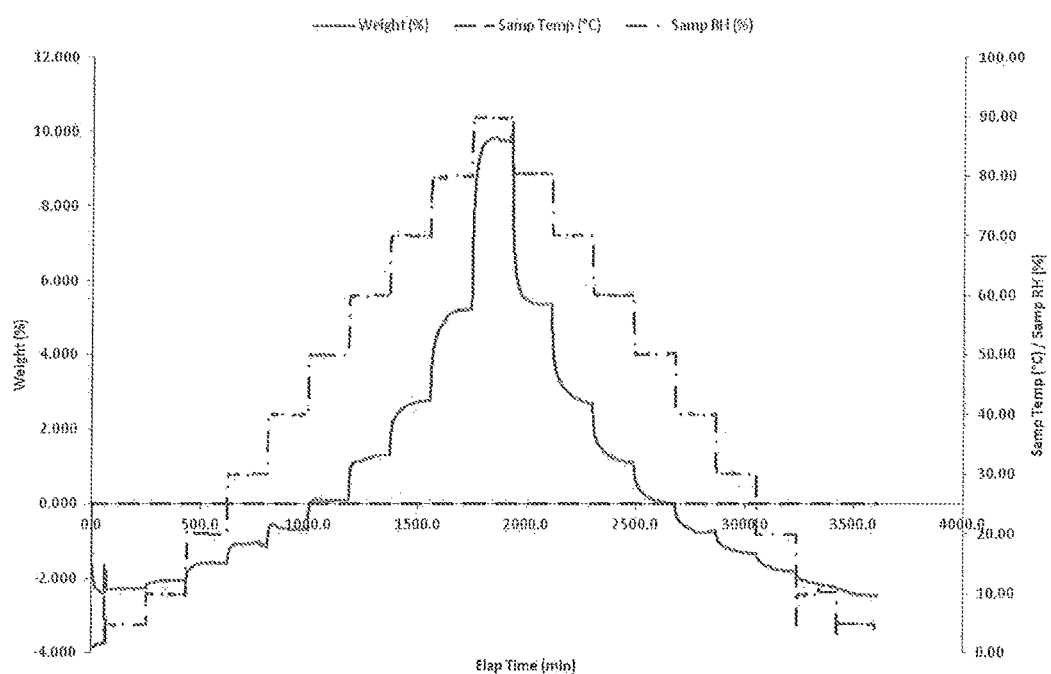
FIG. 22 is a GVS weight versus time profile of the NRH triacetate derivative.

Particles of the triacetate ester of NRH particles were irregular in shape and glassy and non-birefringent based on optical microscopy (See FIG. 19). XRD indicated that the NRH triacetate derivative was amorphous (See FIG. 20). DSC (Differential Scanning Calorimetry) showed no thermal behavior other than that due to thermal decomposition. GVS (see FIGS. 21 and 22) indicated the sample gained greater than 12% in weight from the dried state at 90% RH.

Figure 23:
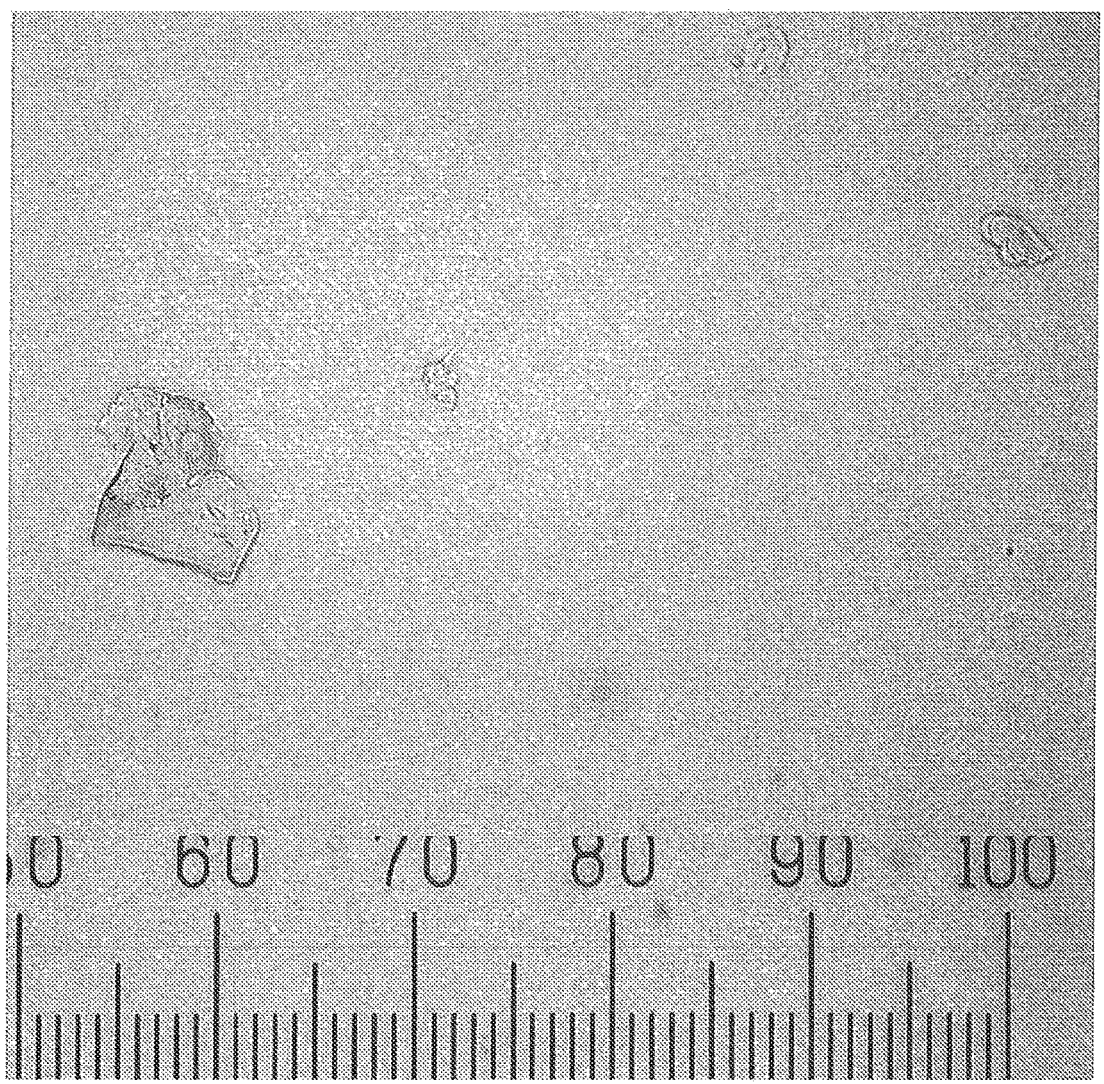
FIG. 23 is a photograph showing the NRH mono palmitate ester particles imaged by optical microscopy (Scale: Each division=10 microns).
Figure 24:
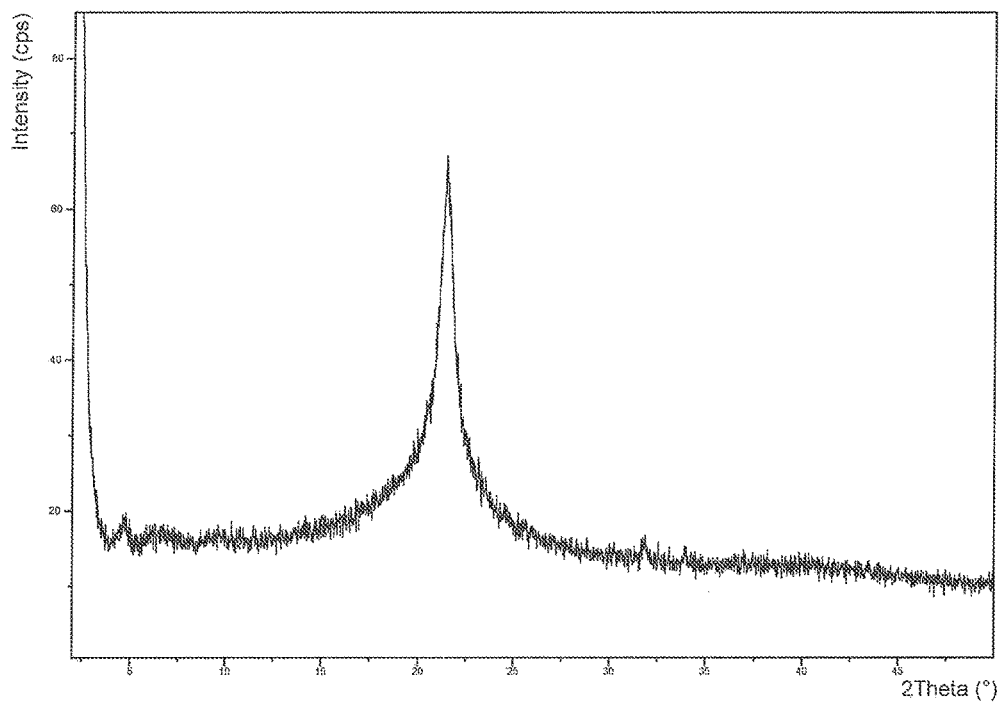
FIG. 24 is an XRD of the NRH mono palmitate ester.
Figure 25:
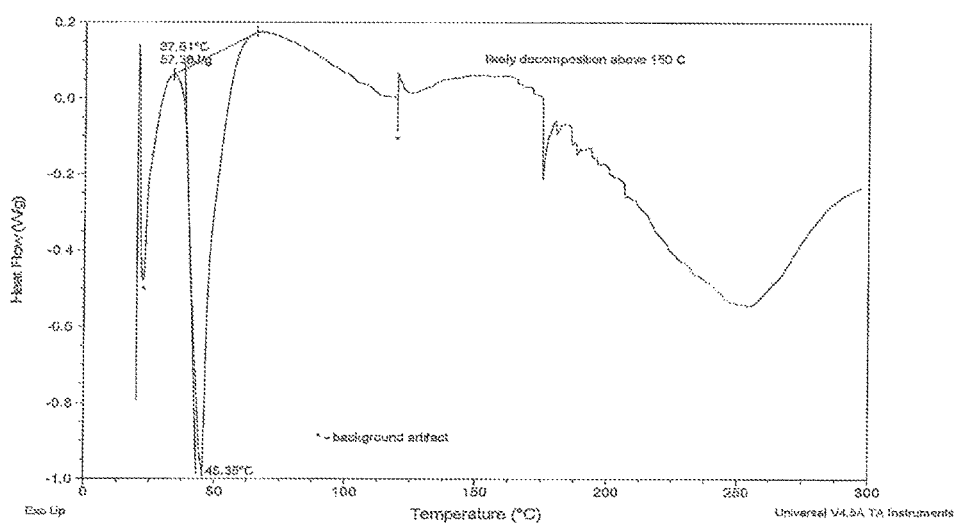
FIG. 25 is a DSC plot of the NRH mono palmitate ester.
Figure 26:
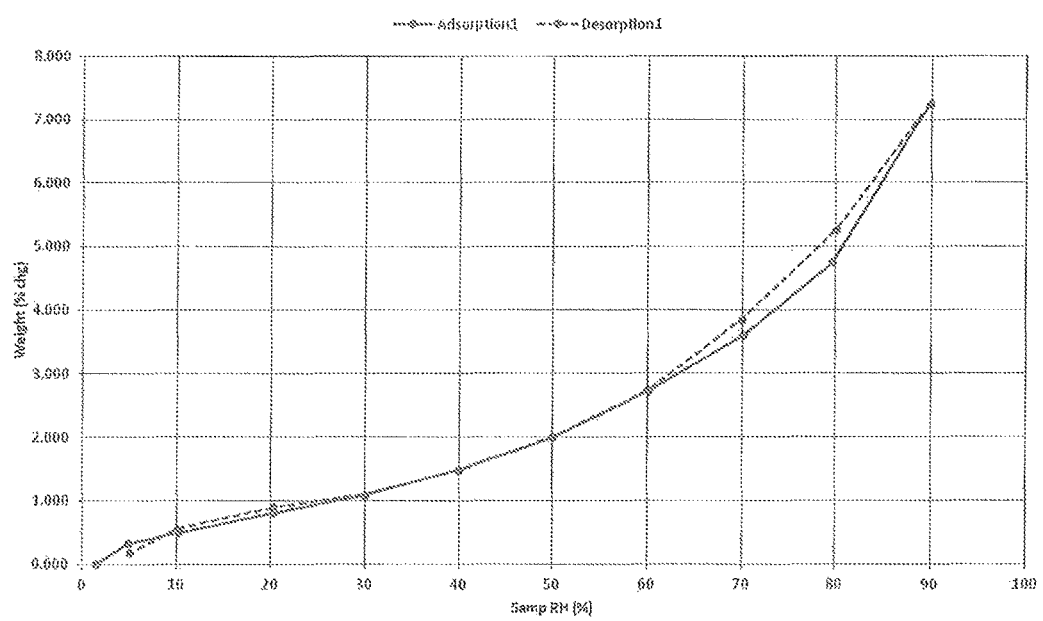
FIG. 26 is a GVS Isotherm (25° C.) of the NRH mono palmitate ester.
Figure 27:
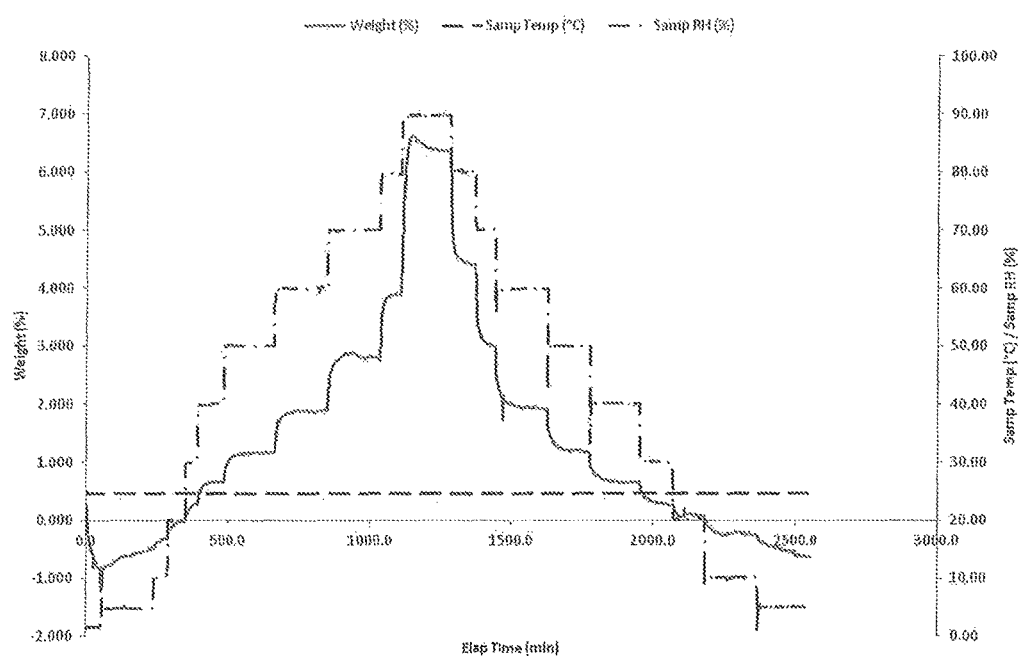
FIG. 27 is a GVS weight versus time profile of the NRH mono palmitate ester.

Optical microscopy of the NRH mono palmitate ester indicated the sample particles were irregular to flat in shape with weak birefringence. FIG. 23 shows the NRH mono palmitate ester particles imaged by optical microscopy. XRD of the NRH mono palmitate ester indicated the sample exhibited a simple order with a dominant peak at a d-spacing of 4.1 nm consistent with the hexagonally ordered lateral packing of the palmitic side chains. The sample lacks a full three-dimensionally crystalline structure. DSC of the NRH mono palmitate ester exhibited an endothermic transition with an onset at approximately 38° C. which is attributed to the melting of the hexagonally packed palmitic side chains. Upon further heating, additional features are attributed to thermal decomposition (See FIG. 25). GVS of NRH mono palmitate ester (see FIGS. 26 and 27) indicated the sample gained approximately 7% by weight from the dried state at 90% RH (25° C.). The GVS profile at 90% RH showed an initial rise and then fall in weight but there was no evidence of crystallization of the sample post-GVS.

Figure 28:
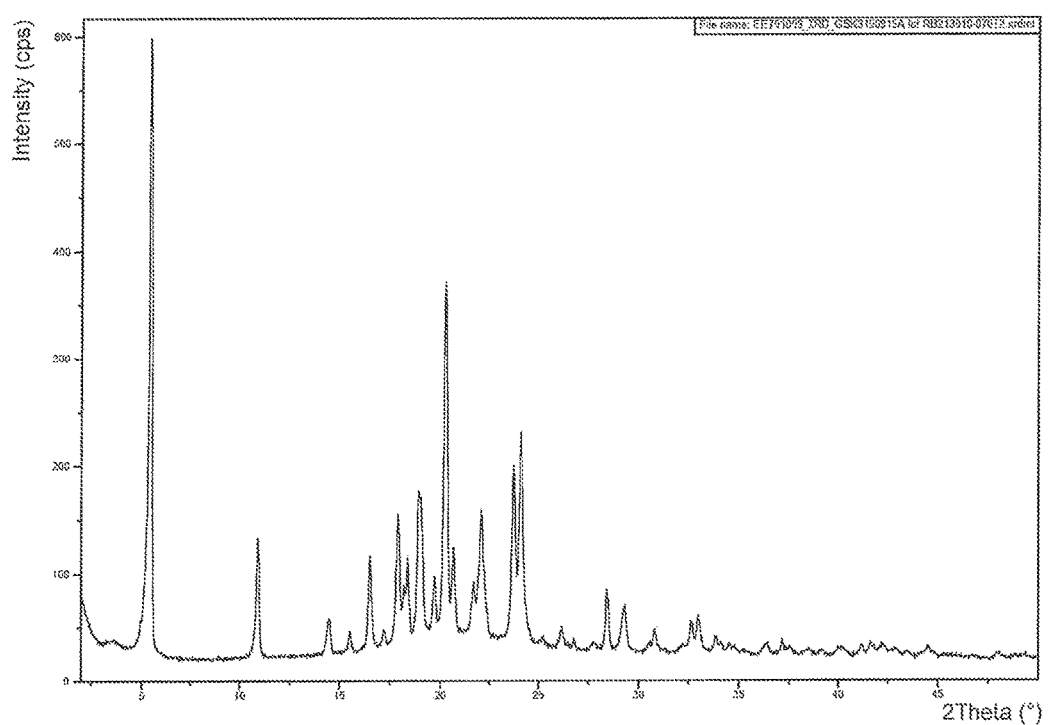
FIG. 28 is a XRD of the mono C6-NRH preparation.
Figure 29:
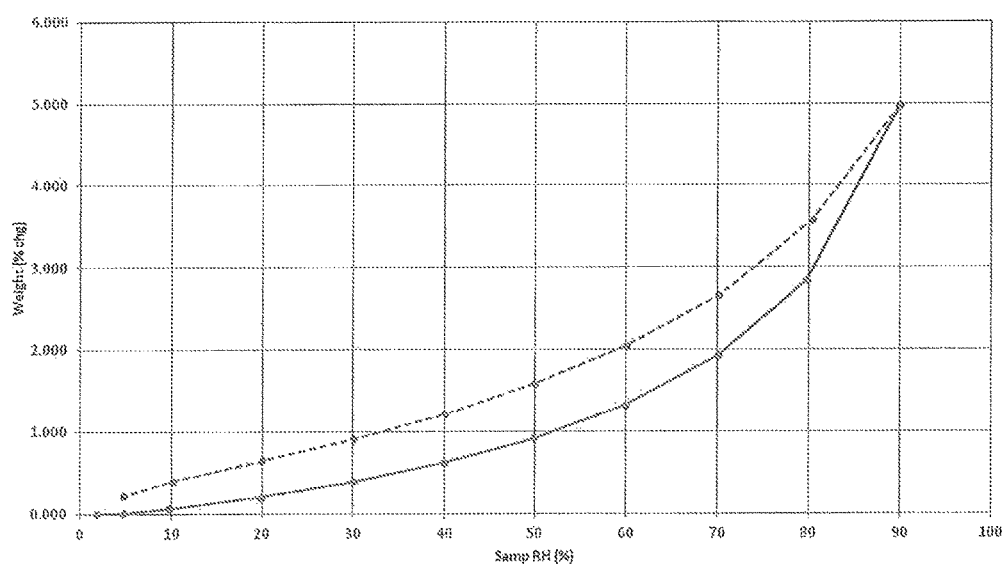
FIG. 29 is a GVS weight versus time profile of the mono C6-NRH preparation.
Figure 30:
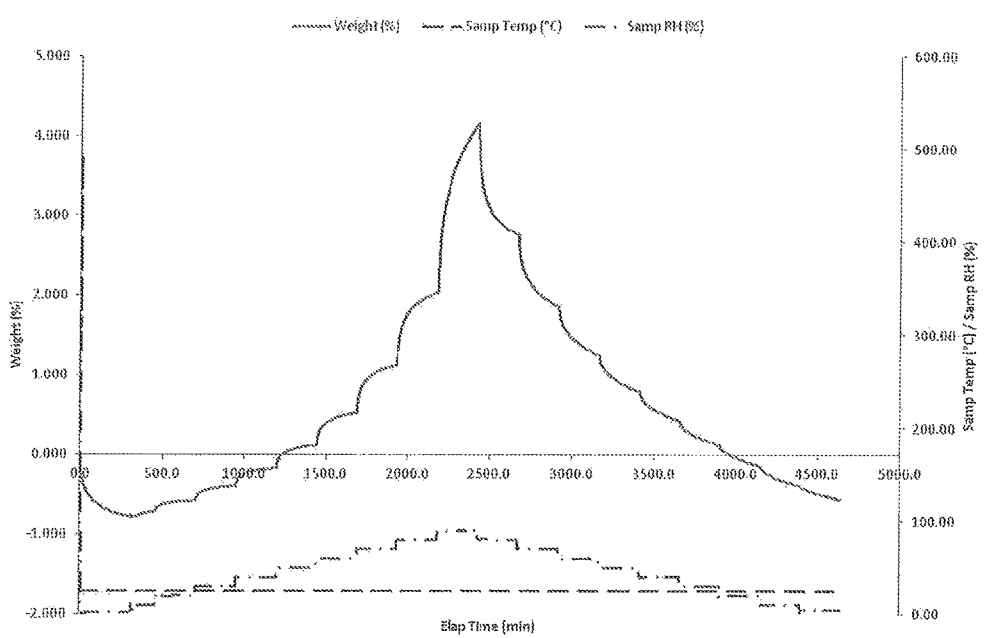
FIG. 30 is a GVS weight versus time profile of the mono C6-NRH preparation.

XRD of the mono C6-NRH (see FIG. 28) indicated the material was primarily crystalline. A small hump in the XRD baseline indicated the sample contained some disordered material. When the amorphous hump and crystalline peak responses were deconvoluted from each other, the crystalline (based on area percent) component was estimated to be approximately 80%. GVS (see FIGS. 29 and 30) indicated the mono C6-NRH derivative gained approximately 5% in weight from the dried state. The solid line is the absorption phase and the dashed line is the desorption phase in FIG. 29. The hysteresis between the absorption and desorption traces is likely due to lack of complete weight equilibration at each % RH step. FIG. 30 indicates that the sample weight had not reach full equilibrium at the higher % RH steps (60% RH and higher) so the 5% weight gain at 90% RH shown in FIG. 29 is likely slightly lower than the true equilibrium value. XRD indicated there was no further crystallization following the GVS treatment of the sample.

EQUIVALENTS

The present invention provides among other things nicotinamide riboside NAD precursor compounds, and salts and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

Also incorporated by reference are the following PCT Publications: WO 2000/032194; WO 2000/32179; WO 2001/078727; WO 2004/016726; WO 2005/002672; WO 2006/116322; WO 2005/077091; WO 2006/001982; WO 2006/105440; WO 2006/116322; WO 2007/005453; WO 2007/061798; WO2008/089439; WO 2008/091710; WO 2010/11111; WO 2011/081942; WO 2012/094343; WO 2012/114204; WO 2014/014/014828; and WO98/16186; WO2002/004478; WO2012/125900; U.S. Pat. No. 2,798,076; and US20130078217.

We claim:
1. A compound represented by Structural Formula (I) or (II):

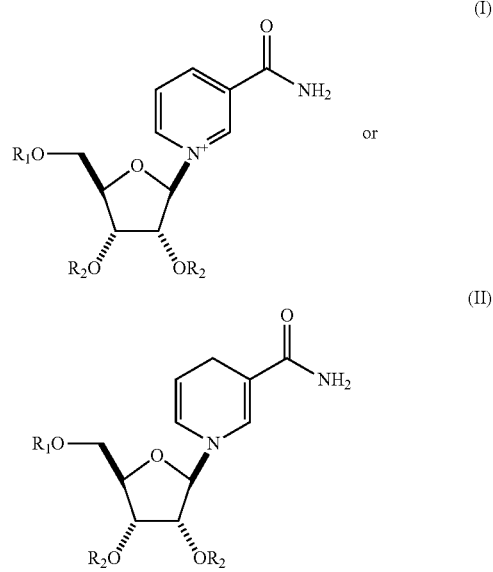

or a pharmaceutically acceptable salt thereof, wherein:
$R_1$ is C(=O)—X—$C_4$-$C_{18}$ straight chain or branched alkyl or —C(=O)—X—$C_2$-$C_{18}$ straight chain or branched alkenyl;
each $R_2$ is independently selected from hydrogen, and a —C(O)—X—$C_1$-$C_{18}$ straight chain or branched alkyl or a —C(O)—X—$C_2$-$C_{18}$ straight chain or branched alkenyl; and
X is a covalent bond or O.

2. The compound of claim 1, which is a sterioisomerically pure compound represented by Strucutral Formula (I) or (II), or a pharmaceutically acceptable salt thereof.

3. The compound of claim 1, wherein the compound is represented by Structural Formula (I).

4. The compound of claim 1, wherein the compound is represented by Structural Formula (II).

5. The stereoisomerically pure compound of claim 1, wherein each $R_2$ is hydrogen.

6. The compound of claim 5, wherein the compound is selected from the group consisting of:

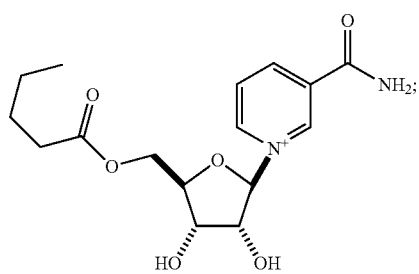
(nicotinamide riboside 5′-monopentanoate)

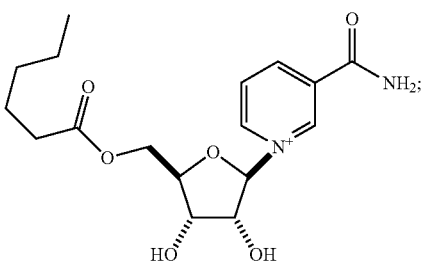
(nicotinamide riboside 5′-monohexanoate)

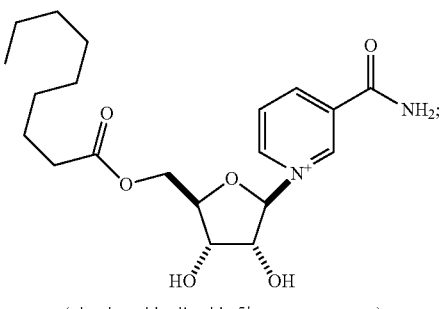
(nicotinamide riboside 5′-monononanoate)

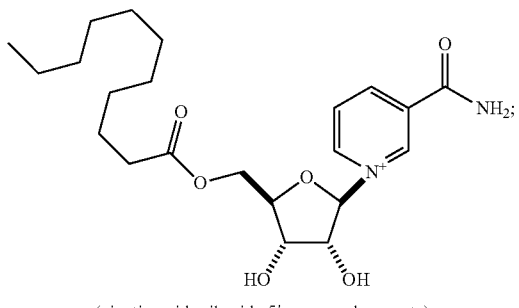
(nicotinamide riboside 5′-monoundecanoate)

-continued

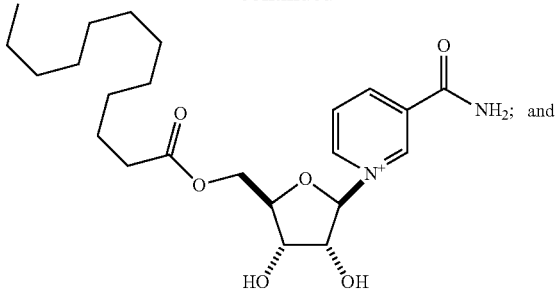
(nicotinamide riboside 5′-monododecanoate)

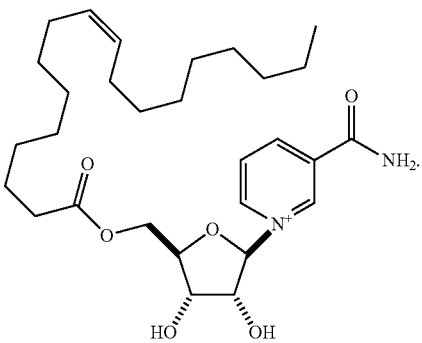
(nicotinamide riboside 5′-monooleate)

or a pharmaceutically acceptable salt thereof.

7. The compound of claim 1, wherein $R_1$ is —C(=O)—X—$C_4$-$C_{10}$ straight chain or branched alkyl.

8. The compound of claim 1, wherein $R_1$ is—C(=O)—X—$C_{11}$-$C_{18}$ straight chain or branched alkyl.

9. A pharmaceutically acceptable salt of a compound of claim 1 which comprises an anion selected from the group consisting of chloride, bromide, iodide, nitrate, sulfate, sulfite, phosphate, carbonate, bicarbonate, methanesulfonate (mesylate), ethanesulfonate, propanesulfonate, benzenesulfonate (bezylate), para-toluenesulfonate (tosylate), thiocyanate, and trifluoromethanesulfonate.

10. A pharmaceutically acceptable salt of a compound of claim 1, which comprises an anion selected from the group consisting of trifluoroacetate, formate, acetate, propionate, butyrate, isobutyrate, pentanoate (valerate), isopentanoate, hexanoate (caproate), isohexanoate, heptanoate (enanthate), isoheptanoate, octanoate (caprylate), isooctanoate, nonanoate (pelargonate), isononanoate, decanoate (caprate),laurate, oleate, palmitate, stearate, undecylenate, benzoate, nicotinate, lactate, glucuronate, tartrate, malate, succinate, fumarate, malonate, tartarate, hydroxysuccinate, 2-oxosuccinate, 2-oxoglutarate, acetonedicarboxylate, phthalate, oxalate, adipate, glutarate, sebacate, maleate, citrate, ethylenediamine tetraacetate, aspartate, and glutamate.

11. The compound of claim 5, which is stereoisomerically pure, and wherein the compound is selected from the group consisting of:

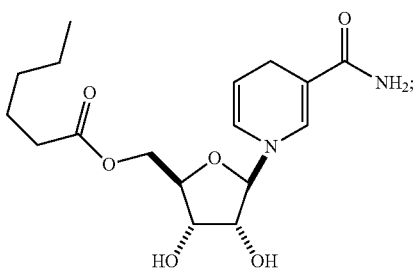
(nicotinamide riboside hydride 5′-monohexanoate)

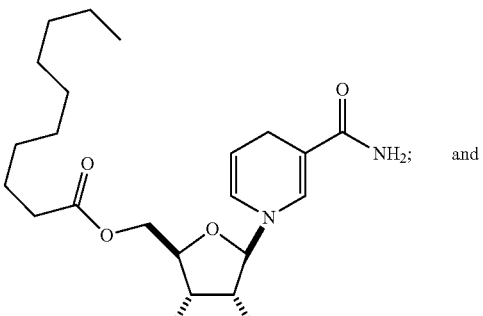
(nicotinamide riboside hydride 5′-monodecanoate) and

-continued

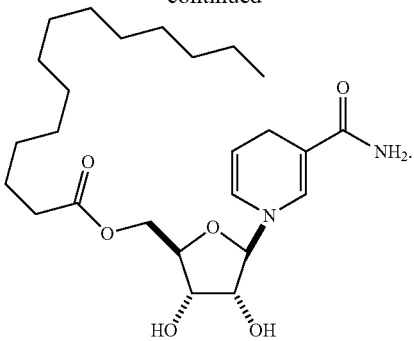
(nicotinamide riboside hydride 5′-monotetradecanoate)

12. A composition comprising the stereoisomerically pure β-anomeric compound of claim 1, wherein the composition comprises less than 5% of the α-anomer.

13. A pharmaceutical or cosmetic composition comprising a compound of claim 1 and a pharmaceutically or cosmetically acceptable carrier.

14. The pharmaceutical or cosmetic composition of claim 13, wherein the pharmaceutically or cosmetically acceptable carrier is formulated for topical administration.

15. The pharmaceutical or cosmetic composition for topical administration of claim 14, wherein the composition is in a form selected from an ointment, a lotion, a cream, a microemulsion, a gel, an oil, and a solution.

16. The pharmaceutical or cosmetic composition for topical administration of claim 14, further comprising an additional active agent selected from an anti-inflammatory agent, an analgesic agent, an antimicrobial agent, an antifungal agent, an antibiotic agent, a vitamin, an antioxidant agent, and a sunblock agent.

17. A method of treating a skin disorder or disease associated with or caused by inflammation, sun damage, oxidative stress or natural aging comprising administering the pharmaceutical or cosmetic composition for topical administration of claim 14 to the skin or mucosal tissue of a subject in need thereof.

18. The composition of claim 1, comprising a diastereomeric mixture of the compound of formula (I) or (II), or pharmaceutically acceptable salt thereof.

* * * * *